United States Patent [19]
Nakai et al.

[11] Patent Number: 5,432,178
[45] Date of Patent: Jul. 11, 1995

[54] AMIDINOPHENOL DERIVATIVES

[75] Inventors: Hisao Nakai; Masanori Kawamura, both of Mishima; Tsumoru Miyamoto, Shiga, all of Japan

[73] Assignee: Ono Pharmaceutical Co., Ltd., Osaka, Japan

[21] Appl. No.: 121,499

[22] Filed: Sep. 16, 1993

[30] Foreign Application Priority Data

Sep. 18, 1992 [JP] Japan .................................. 4-274992
Mar. 31, 1993 [JP] Japan .................................. 5-096758

[51] Int. Cl.$^6$ ................ A61K 31/495; A61K 31/445; C07D 241/04; C07D 295/182
[52] U.S. Cl. ............................. 514/255; 514/247; 514/331; 544/224; 544/386; 544/387; 544/388; 544/389; 544/391; 544/392; 548/491; 548/566; 546/231; 560/16; 560/24; 560/37; 560/39; 560/41
[58] Field of Search .................. 514/255, 247, 331; 544/386, 387, 389, 391, 392, 224, 388; 546/231

[56] References Cited

U.S. PATENT DOCUMENTS

| | | | |
|---|---|---|---|
| 4,514,416 | 4/1985 | Fujii et al. | 549/442 |
| 4,570,006 | 2/1986 | Fujii et al. | 549/442 |
| 4,639,365 | 1/1987 | Sherry | 424/9 |
| 4,642,303 | 2/1987 | Renken | 502/365 |
| 4,888,447 | 12/1989 | Smith | 564/480 |
| 4,976,950 | 12/1990 | Simon et al. | 424/1.1 |

FOREIGN PATENT DOCUMENTS

| | | | |
|---|---|---|---|
| 1260068 | 11/1986 | Japan | 544/386 |
| 1260074 | 11/1986 | Japan | 544/386 |

OTHER PUBLICATIONS

Japan J. Pharmacol., 52, 23–34, 1990, Oda et al., "Pharmacological Studies on 6-Amidino-2-Naphthyl[4-(4-,5-dihydro-1H-imidazol-2-yl)amino]Benzoate Dimethane Sulfonate (FUT-187). I: Inhibitory Activities on Various Kinds of Enzymes in Vitro and Anticomplement Activity In Vivo".

Journal of American Chemical Society, 96, 2268–2270 (1974) J. E. Richman et al.
Organic Synthesis, VI(Collective Volume), 58, 86–97 (1978) T. J. Atkins et al.
Chemical Abstract, 100(13): 102774f (Romanian Patent, RO 79987 B, 30 Sep. 1982), 1981.
Chemical Abstract, :2456a(Belgian Patent 613,063, 15 Feb. 1962 to Armour & Co.), 1962.
Coor. Chemical Review, 110, 17 (1991)A. Bianchi et al.
Journal of Organic Chemistry, 56 452–454 (1991) A. Galan et al.
Journal of Organic Chemistry, 26, 131 (1961).
Tet. Letters, 52, 5149 (1978).
Journal of American Chemical Society, 110, 6266–6267 (1988).

Primary Examiner—Yogendra N. Gupta
Attorney, Agent, or Firm—Stevens, Davis, Miller & Mosher

[57] ABSTRACT

Amidinophenol derivatives of the formula (I):

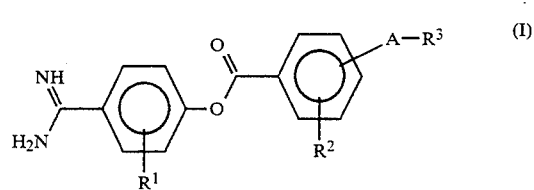

wherein $R^1$ and $R^2$ are (i) H, (ii) C1–4 alkyl, (iii) C1–4 alkoxy, (iv) C2–5 acyl, (v) halogen, (vi) NO$_2$, (vii) benzoyl, (viii) COOR$^4$ (in which R$^4$ is C1–3 alkyl); A is bond, C1–4 alkylene, —C(R$^5$)=C(R$^6$)— (in which R$^5$ and R$^6$ are H or C1–4 alkyl; R$^3$ is (i) CON(R$^7$)(R$^8$), (ii) CON(R$^9$)—CH(R$^7$)(R$^8$) or (iii)

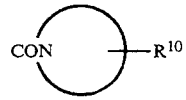

in which (Abstract continued on next page.)

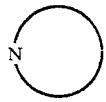
is 4–7 membered, mono-cyclic hetero ring containing 1 or 2 N atom; $R^{10}$ is H, C7–10 phenylalkyl or $COOR^{13}$ (in which $R^{13}$ is H, C1–4 alkyl or C7–10 phenylalkyl)); with the proviso that (i) both $R^7$ and $R^8$ do not represent hydrogen at the same time, and (ii) when at least one group in $R^7$, $R^8$ and $R^9$ represents the group containing t-butyl ester, the other groups do not represent the group containing carboxy; or an acid-addition salt thereof, have inhibitory activities on $PLA_2$ and on various proteases such as trypsin, plasmin, thrombin, kallikrein, especially trypsin, and are useful for the prevention and/or the treatment of various inflammatory diseases, allergic diseases, disseminated intravascular coagulation, pancreatitis, severity in pancreatitis and multiple organ failure.

8 Claims, No Drawings

AMIDINOPHENOL DERIVATIVES

FIELD OF THE INVENTION

The present invention relates to amidinophenol derivatives.

More particularly, it relates to:
(i) amidinophenol derivatives of the formula (I):

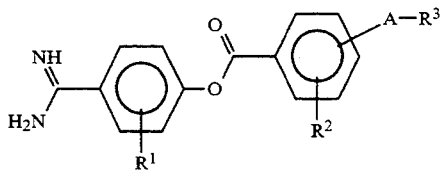

(wherein the various symbols are the same meaning hereafter described) and acid addition salts thereof, having an inhibitory activity on phospholipase ($PLA_2$) and on various proteases such as trypsin, plasmin, thrombin, kallikrein, especially trypsin,
(ii) processes for the preparation thereof, and
(iii) pharmaceutical agents containing them.

1. Background of the Invention

Phospholipase $A_2$ ($PLA_2$) is an enzyme which acts on phospholipids existing in cell membrane and hydrolyzes an ester bond at the second position of the phospholipids. There are known two kinds of $PLA_2$, i.e., membrane-associated $PLA_2$ and pancreatic $PLA_2$.

Membrane-associated $PLA_2$ acts on phospholipids to release archidonic acid (AA) to form the phospholipids. The AA is converted into prostaglandins, thromboxanes and leukotrienes, which are physiologically active substances inducing various inflammatory diseases and allergic diseases.

On the other hand, pancreatic $PLA_2$ degrades phospholipids and destructs cell membrane, thereby to produce lysolecithin having strong cytotoxicity. Recently, much importance has been attached to pancreatitis, severity in pancreatitis and multiple organ failure induced by such destructive activity on cell membrane, and it has been more remarkable. Further, it is reported that membrane-associated $PLA_2$ is also concerned with these diseases.

Accordingly, the inhibition on $PLA_2$ leads to the suppression of the release of AA, a precursor of various physiologically active substances, and therefore, it is considered to be useful for the prevention and/or the treatment of various inflammatory and allergic diseases. Furthermore, it is considered to be useful for the prevention and/or the treatment of pancreatitis, severity in pancreatitis and multiple organ failure due to the inhibition of destructive activity on cell membrane.

2. Related Arts

Many compounds having an inhibitory activity on $PLA_2$ are known. For example, there are known guanidinobenzoic acid derivatives such as camoslat mesylate (code No. FOY-305) of the formula (X):

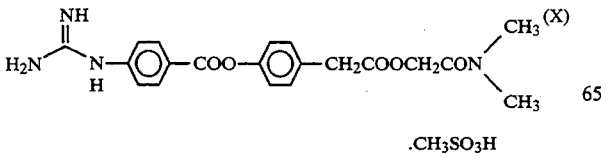

and nafamostat mesilate (code No. FUT-175) of the formula (Y):

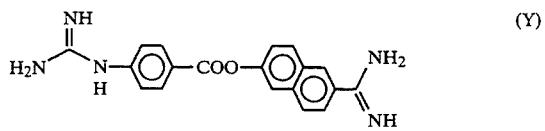

(see Japan. J. Pharmacol., 52, 23–34, 1990).

Further, there is known as a compound having a chemical structure partially similar to ones of the present invention, compounds of the formula (Z):

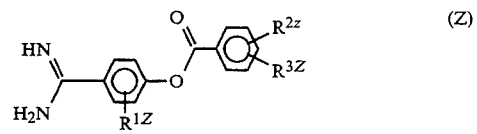

where in
$R^{1z}$ is:
(i) C1–4 alkyl,
(ii) C1–4 alkoxy,
(iii) carboxy,
(iv) $COOR^{4z}$ (in which $R^{4z}$ is C1–4 alkyl),
(v) halogen,
(vi) nitro,
(vii) sulfo,
(viii) benzoyl or

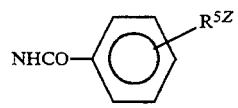

(in which $R^{5z}$ is hydrogen or guanidino);
$R^{2z}$ and $R^{3z}$ each, independently, is:
(i) $NHCO-R^{6z}$ (in which $R^{6z}$ is C1–4 alkyl) or

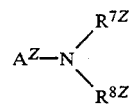

(in which $A^z$ is bond, methylene or ethylene,
$R^{7z}$ and $R^{8z}$ each, independently, is
(1) hydrogen,
(2) C1–4 alkyl or
(3) amino-protecting group (it refers to
(a) $COOR^{9z}$ in which $R^{9z}$ is t-butyl or benzyl,
(b) acetyl,
(c) benzoyl,
(d) tosyl or
(e) nitro); (definitions not related are omitted) (see the specification of the U.S. Pat. Nos. 4,514,416, and 4,570,006). It is disclosed that the compounds have an inhibitory activity on protease such as trypsin, plasmin and anti-complement effect, but it is not entirely known that the compounds have an inhibitory activity on $PLA_2$.

PURPOSE OF THE INVENTION

As the result of energetic investigations in order to find novel amidinophenol derivatives possessing an inhibitory activity on $PLA_2$, we have found that the purpose is accomplished by the amidinophenol derivatives of the formula (I).

Furthermore, we have found that the compounds of the present invention possess additionally a strong inhibitory activity on various proteases such as trypsin, plasmin, thrombin, kallikrein, especially trypsin.

Comparison with the Related Arts

The amidinophenol derivatives of the present invention have never been known before, and, therefore, are quite novel.

To summarize, $R^{2z}$ and $R^{3z}$ in the formula (Z) hereinbefore depicted can represent $NHCO-R^{6z}$, but the nitrogen atom in the said group is attached directly to a benzene ring, and further $R^{6z}$ represents only an alkyl group. On the other hand, $R^3$ in the compounds of the present invention represents $CON(R^7)(R^8)$, $CON(R^9)$-$CH(R^7)(R^8)$ or a group of the formula:

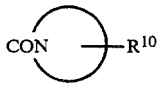

and in any case, the carbon atom in the said group is attached to a benzene ring via a group of A.

From the above viewpoint, it can be said that the compounds of the present invention have the chemical structure quite different from the compounds of the formula (Z).

Furthermore, it has never been known that amidinophenol derivatives (compounds of the formula (Z) hereinabove depicted) have an inhibitory activity on $PLA_2$ though some guanidinobenzoic acid derivatives (compounds of the formulae (X) and (Y) hereinbefore depicted) have already been known to have the activity.

Accordingly, it is quite unexpected from the related arts, that the amidinophenol derivatives of the present invention have an inhibitory activity on $PLA_2$.

DISCLOSURE OF THE INVENTION

The present invention relates to:
(1) compounds of the formula (I):

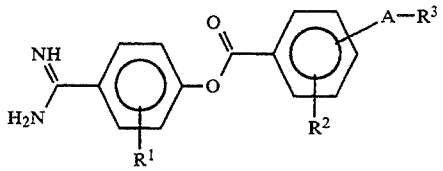

wherein
$R^1$ and $R^2$ each, independently, is:
 (i) hydrogen,
 (ii) C1–4 alkyl,
 (iii) C1–4 alkoxy,
 (iv) C2–5 acyl,
 (v) halogen,
 (vi) nitro,
 (vii) benzoyl or
 (viii) $COOR^4$ (in which $R^4$ is C1–3 alkyl);

A is bond, C1–4 alkylene or

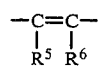

(in which $R^5$ and $R^6$ each independently, is hydrogen or C1–4 alkyl);
$R^3$ is

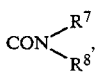 (i)

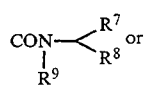 or (ii)

 (iii)

in which $R^7$ and $R^8$ each, independently, is
 (1) hydrogen,
 (2) phenyl,
 (3) C7–10 phenylalkyl,
 (4) phenyl or C7–10 phenylalkyl each of which is substituted by one or two substituents optionally selected from C1–4 alkyl, halogen and
$R^{11}$—$COOR^{12}$ (in which $R^{11}$ is
 (a) bond,
 (b) C 1–8 alkylene,
 (c) C2–8 alkenylene or
 (d) C2–8 alkynylene, and
$R^{12}$ is
 (a) hydrogen,
 (b) C 1–4 alkyl,
 (c) C7–10 phenylalkyl,
 (d) phenyl,
 (e) allyl (i.e., —$CH_2CH=CH_2$) or
 (f) propargyl (i.e.,—$CH_2C\equiv CH$),
 (5) C1–10 alkyl,
 (6) C2–10 alkenyl having one to three double bonds,
 (7) C2–10 alkynyl having one or two triple bonds,
 (8) $R^{11a}$—$COXR^{12}$ (in which $R^{11a}$ is
 (a) bond,
 (b) C1–8 alkylene,
 (c) C2-alkylene in which one or two carbon atoms in the main chain are replaced by sulfur, or sulfur and phenylene,
 (d) C2–8 alkenylene,
 (e) C4–8 alkenylene in which one or two carbon atoms in the main chain are replaced by sulfur, or sulfur and phenylene,
 (f) C2–8 alkynylene, or
 (g) C4–8 alkynylene in which one or two carbon atoms in the main chain are replaced by sulfur, or sulfur and phenylene,
X is oxygen or —NH—, and $R^{12}$ is the same meaning as hereinbefore defined),
 (9) C1-alkyl which is substituted by a 7–14 membered, bi- or tri-cyclic hetero ring containing one nitrogen, or
 (10) C3–7 cycloalkyl);
$R^9$ is
 (1) hydrogen, (2) C1-8 alkyl,
(3) C7-10 phenylalkyl,
(4) C2-10 alkenyl having one to three double bonds,
(5) C2-10 alkynyl having one or two triple bonds,
(6) $R^{11}$—$COOR^{12}$ (in which $R^{11}$ and $R^{12}$ are the same meaning as hereinbefore defined), or
(7) C3-7 cycloalkyl;

is a 4-7 membered, mono-cyclic hetero ring containing one or two nitrogen;
$R^{10}$ is
(1) hydrogen,
(2) C7-10 phenylalkyl or
(3) $COOR^{13}$ (in which $R^{13}$ is hydrogen, C1-4 alkyl or C7-10 phenylalkyl);
with the proviso that
(i) both $R^7$ and $R^8$ do not represent hydrogen at the same time, and
(ii) when at least one group in $R^7$, $R^8$ and $R^9$ represents the group containing t-butyl ester, the other groups do not represent the group containing carboxy;
or an acid-addition salt thereof;
(2) processes for the preparation thereof; and
(3) pharmaceutical agents containing them as active ingredient.

Throughout the specification including claims, it may be easily understood by those skilled in the art, that all isomers are included in the present invention. For example, the alkyl, alkoxy, alkylene, alkenylene and alkynylene groups include straight-chain and also branched-chained ones, and the double bonds in the alkenylene group include E, Z and EZ mixture. Accordingly, all isomers produced by the existence of asymmetric carbon atoms are included in the present invention when branched-chain alkyl, alkoxy, alkylene, alkenylene, alkynylene etc. exist.

In the formula (I), the C1-4 alkyl group represented by $R^1$, $R^2$, $R^5$, $R^6$, $R^{12}$ and $R^{13}$, and that in $R^7$ and $R^8$, means methyl, ethyl, propyl, butyl and the isomers thereof.

In the formula (I), the C1-4 alkoxy group represented by $R^1$ and $R^2$, means methoxy, ethoxy, propoxy, butoxy and the isomers thereof.

In the formula (I), the C1-3 alkyl group represented by $R^4$, means methyl, ethyl, propyl and the isomers thereof.

In the formula (I), the C2-5 acyl group represented by $R^1$ and $R^2$, means acetyl, propionyl, butyryl, valeryl and the isomers thereof.

In the formula (I), the C1-10 alkyl group represented by $R^7$ and $R^8$, means methyl, ethyl, propyl, butyl, pentyl, hexyl, heptyl, octyl, nonyl, decyl and the isomers thereof.

In the formula (I), the C1-8 alkyl group represented by $R^9$, means methyl, ethyl, propyl, butyl, pentyl, hexyl, heptyl, octyl and the isomers thereof.

In the formula (I), the C7-10 phenylalkyl group represented by $R^7$, $R^8$, $R^9$, $R^{10}$, $R^{12}$ and $R^{13}$, means methyl, ethyl, propyl, butyl and the isomers thereof, which are substituted by a phenyl group.

In the formula (I), the halogen atom represented by $R^1$ and $R^2$, and that in $R^7$ and $R^8$, mean fluorine, chlorine, bromine and iodine atoms.

In the formula (I), the C1-4 alkylene group represented by A, means methylene, ethylene, trimethylene, tetramethylene and the isomers thereof.

In the formula (I), the C1-8 alkylene group represented by $R^{11}$ and $R^{11a}$, means methylene, ethylene, trimethylene, tetramethylene, pentamethylene, hexamethylene, heptamethylene, octamethylene and the isomers thereof. The C2-8 alkenylene group means vinylene propenylene, butenylene, pentenylene, hexenylene, heptenylene, octenylene and the isomers thereof. The C2-8 alkynylene group means ethynylene, propynylene, butynylene, pentynylene, hexynylene, heptynylene, octynylene and the isomers thereof.

In the formula (I), the C2-8 alkylene in which one or two carbon atoms in the main chain are replaced by sulfur, or sulfur and phenylene, represented by $R^{11a}$, means thiaethylene (i.e., —$CH_2$—S— and —S—$CH_2$—), thiatrimethylene (i.e., —$CH_2$—$CH_2$—S—, $CH_2$—S—$CH_2$— and —S—$CH_2$—$CH_2$—), thiatetramethylene, thiapentamethylene, thiahexamethylene, thiaheptamethylene, thiaoctamethylene and the isomers thereof, or the group in which one of any methylene group in the said thiaalkylene group, is replaced by a phenylene group (e.g., —$CH_2$—S—$CH_2$—$C_6H_4$—).

The C4-8 alkenylene in which one or two carbon atoms in the main chain are replaced by sulfur, or sulfur and phenylene, means thiabutenylene (i.e., —S—$CH_2$—CH=CH— and —CH=CH—$CH_2$—S—), thiapentenylene (i.e., —S—$CH_2$—$CH_2$—CH=CH—, —S—$CH_2$—CH=CH—$CH_2$— and —$CH_2$—S—$CH_2$CH=CH—), thiahexenylene, thiaheptenylene, thiaoctenylene and the isomers thereof, or the group in which one of any methylene groups in the said thiaalkenylene group, is replaced by a phenylene group (e.g., —S—$CH_2$—CH=CH—$C_6H_4$—).

The C4-8 alkynylene in which one or two carbon atoms in the main chain are replaced by sulfur, or sulfur and phenylene, means thiabutynylene (i.e., —S—$CH_2$—C≡C— and —C≡C—$CH_2$—S—), thiapentynylene (i.e., —S—$CH_2$—$CH_2$—C≡C—, —C≡C—$CH_2$—$CH_2$—S—, —S—$CH_2$—C≡C—$CH_2$—, —$CH_2$—C≡C—$CH_2$—S—, $CH_2$—S—$CH_2$—C≡C— and —C≡C—$CH_2$—S—$CH_2$—), thiahexynylene, thiaheptynylene, thiaoctynylene and the isomers thereof, or the group in which one of any methylene groups in the said thiaalkynylene group, is replaced by a phenylene group (e.g., —S—$CH_2$—C≡C—$C_6H_4$—).

In the formula (I), examples of the 7-14 membered, bi- or tri-cyclic hetero ring containing one nitrogen, represented by $R^7$ and $R^8$, are indole, indoline, quinoline, 1,2,3,4-tetrahydroquinoline, carbazole, etc.

In the formula (I), examples of the 4-7 membered, mono-cyclic hetero ring containing one or two nitrogen atoms, represented by:

are pyrrole, pyrrolidine, imidazole, imidazolidine, pyridine, piperidine, pyrazine, piperazine, pyrimidine, etc.

In the formula (I), the C2-10 alkenyl having one to three double bonds, represented by $R^7$ and $R^8$, means ethenyl, propenyl, butenyl, pentenyl, hexenyl, heptenyl, octenyl, nonenyl, decenyl, butadienyl, pentadienyl, hexadienyl, heptadienyl, octadienyl, nonadienyl, decadienyl, hexatrienyl, heptatrienyl, octatrienyl, nonatrienyl, decatrienyl and the isomers thereof.

The C2–10 alkynyl having one or two triple bonds, means ethynyl, propynyl, butynyl, pentynyl, hexynyl, heptynyl, octynyl, nonynyl, decynyl, butadiynyl, pentadiynyl, hexadiynyl, heptadiynyl, octadiynyl, nonadiynyl, decadiynyl and the isomers thereof.

In the formula (I), the cycloalkyl group represented by $R^7$, $R^8$ and $R^9$, means cyclopropyl, cyclobutyl, cyclopentyl, cyclohexyl and cycloheptyl, Examples of representative compounds of the present invention are listed as follows:

(1) p-(p-Amidinophenoxycarbonyl)-α-methylcinnamic acid N-(o, m, p)-ethoxycarbonylphenyl-N-ethoxycarbonylmethylamide, (2) p-(p-Amidinophenoxycarbonyl)-α-methylcinnamic acid N-(o, m, p)-ethoxycarbonylphenyl-N-benzyloxycarbonylmethylamide, (3) p-(p-Amidinophenoxycarbonyl)-α-methylcinnamic acid N-(o, m, p)-ethoxycarbonylphenyl-N-allyloxycarbonylmethylamide, (4) p-(p-Amidinophenoxycarbonyl)-α-methylcinnamic acid N-(o, m, p)-ethoxycarbonylphenyl-N-propargyloxycarbonylmethylamide, (5) p-(p-Amidinophenoxycarbonyl)-α-methylcinnamic acid N-(o, m, p)-ethoxycarbonylmethyl)phenyl-N-ethoxycarbonylmethylamide, (6) p-(p-Amidinophenoxycarbonyl)-α-methylcinnamic acid N-(o, m, p)-(ethoxycarbonylmethyl)phenyl-N-benzyloxycarbonylmethylamide, (7) p-(p-Amidinophenoxycarbonyl)-α-methylcinnamic acid N-(o, m, p)-(ethoxycarbonylmethyl)phenyl-N-allyloxycarbonylmethylamide, (8) p-(p-Amidinophenoxycarbonyl)-α-methylcinnamic acid N-(o, m, p)-(ethoxycarbonylmethyl)phenyl-N-propargyloxycarbonylmethylamide, (9) p-(p-Amidinophenoxycarbonyl)-α-methylcinnamic acid N-(o, m, p)-(ethoxycarbonylphenyl)methyl-N-ethoxycarbonylmethylamide,

(10) p-(p-Amidinophenoxycarbonyl)-α-methylcinnamic acid N-(o, m, p)-(ethoxycarbonylphenyl)methyl-N-benzyloxycarbonylmethylamide,

(11) p-(p-Amidinophenoxycarbonyl)-α-methylcinnamic acid N-(o, m, p)-(ethoxycarbonylphenyl)methyl-N-allyloxycarbonylmethylamide,

(12) p-(p-Amidinophenoxycarbonyl)-α-methylcinnamic acid N-(o, m, p)-(ethoxycarbonylphenyl)methyl-N-propargyloxycarbonylmethylamide,

(13) p-(p-Amidinophenoxycarbonyl)-α-methylcinnamic acid N-[(o, m, p)-(ethoxycarbonylmethyl)phenyl]-methyl-N-ethoxycarbonylmethylamide,

(14) p-(p-Amidinophenoxycarbonyl)-α-methylcinnamic acid N-[(o, m, p)-(ethoxycarbonylmethyl)phenyl]-methyl-N-benzyloxycarbonylmethylamide,

(15) p-(p-Amidinophenoxycarbonyl)-α-methylcinnamic acid N-[(o, m, p)-(ethoxycarbonylmethyl)phenyl]-methyl-N-allyloxycarbonylmethylamide,

(16) p-(p-Amidinophenoxycarbonyl)-α-methylcinnamic acid N-[(o, m, p)-(ethoxycarbonylmethyl)phenyl]-methyl-N-propargyloxycarbonylmethylamide,

(17) p-(p-Amidinophenoxycarbonyl)-α-methylcinnamic acid N-2-ethoxycarbonylethenyl-N-ethoxycarbonylmethylamide,

(18) p-(p-Amidinophenoxycarbonyl)-α-methylcinnamic acid N-2-ethoxycarbonylethenyl-N-benzyloxycarbonylmethylamide,

(19) p-(p-Amidinophenoxycarbonyl)-α-methylcinnamic acid N-2-ethoxycarbonylethenyl-N-allyloxycarbonylmethylamide,

(20) p-(p-Amidinophenoxycarbonyl)-α-methylcinnamic acid N-2-ethoxycarbonylethenyl-N-propargyloxycarbonylmethylamide,

(21) p-(p-Amidinophenoxycarbonyl)-α-methylcinnamic acid N-1-methyl-2-ethoxycarbonylethenyl-N-ethoxycarbonylmethylamide,

(22) p-(p-Amidinophenoxycarbonyl)-α-methylcinnamic acid N-1-methyl-2-ethoxycarbonylethenyl-N-benzyloxycarbonylmethylamide,

(23) p-(p-Amidinophenoxycarbonyl)-α-methylcinnamic acid N-1-methyl-2-ethoxycarbonylethenyl-N-allyloxycarbonylmethylamide,

(24) p-(p-Amidinophenoxycarbonyl)-α-methylcinnamic acid N-1-methyl-2-ethoxycarbonylethenyl-N-propargyloxycarbonylmethylamide,

(25) p-(p-Amidinophenoxycarbonyl)-α-methylcinnamic acid N-2-ethoxycarbonyl-1-propenyl-N-ethoxycarbonylmethylamide,

(26) p-(p-Amidinophenoxycarbonyl)-α-methylcinnamic acid N-2-ethoxycarbonyl-1-propenyl-N-benzyloxycarbonylmethylamide,

(27) p-(p-Amidinophenoxycarbonyl)-α-methylcinnamic acid N-2-ethoxycarbonyl-1-propenyl-N-allyloxycarbonylmethylamide,

(28) p-(p-Amidinophenoxycarbonyl)-α-methylcinnamic acid N-2-ethoxycarbonyl-1-propenyl-N-propargyloxycarbonylmethylamide,

(29) p-(p-Amidinophenoxycarbonyl)-α-methylcinnamic acid N-2-ethoxycarbonylethynyl-N-ethoxycarbonylmethylamide,

(30) p-(p-Amidinophenoxycarbonyl)-α-methylcinnamic acid N-2-ethoxycarbonylethylny-N-benzyloxycarbonylmethylamide,

(31) p-(p-Amidinophenoxycarbonyl)-α-methylcinnamic acid N-2-ethoxycarbonylethynyl-N-allyloxycarbonylmethylamide,

(32) p-(p-Amidinophenoxycarbonyl)-α-methylcinnamic acid N-2-ethoxycarbonylethynyl-N-propargyloxycarbonylmethylamide,

(33) p-(p-Amidinophenoxycarbonyl)-α-methylcinnamic acid N-(1-ethoxycarbonyl-1-phenylmethyl)methyl-N-ethoxycarbonylmethylamide,

(34) p-(p-Amidinophenoxycarbonyl)-α-methylcinnamic acid N-(1-benzyloxycarbonyl-1-phenyl methyl)methyl-N-ethoxycarbonylmethylamide,

(35) p-(p-Amidinophenoxycarbonyl)-α-methylcinnamic acid N-(1-ethoxycarbonyl-1-phenylmethyl)methyl-N-benzyloxycarbonylmethylamide,

(36) p-(p-Amidinophenoxycarbonyl)-α-methylcinnamic acid N-[1-(o, m, p)-ethoxycarbonylphenyl-1-ethoxycarbonyl]methylamide,

(37) p-(p-Amidinophenoxycarbonyl)-α-methylcinnamic acid N-[1-(o, m, p)-ethoxycarbonylphenyl-1-benzyloxycarbonyl]methylamide,

(38) p-(p-Amidinophenoxycarbonyl)-α-methylcinnamic acid N-[1-(o, m, p)-ethoxycarbonylphenyl-1-allyloxycarbonyl]methylamide,

(39) p-(p-Amidinophenoxycarbonyl)-α-methylcinnamic acid N-[1-(o, m, p)-ethoxycarbonylphenyl-1-propargyloxycarbonyl]methylamide,

(40) p-(p-Amidinophenoxycarbonyl)-α-methylcinnamic acid N-[1-(o, m, p)-(ethoxycarbonylmethyl)-1-ethoxycarbonyl]methylamide,

(41) p-(p-Amidinophenoxycarbonyl)-α-methylcinnamic acid N-[1-(o, m, p)-(ethoxycarbonylmethyl)-phenyl-1-benzyloxycarbonyl]methylamide,

(42) p-(p-Amidinophenoxycarbonyl)-α-methylcinnamic acid N-[1-(o, m, p)-(ethoxycarbonylmethyl)phenyl-allyloxycarbonyl]methylamide,

(43) p-(p-Amidinophenoxycarbonyl)-α-methylcinnamic acid N-[1-(o, m, p)-(ethoxycarbonylmethyl)phenyl-1-propargyloxycarbonyl]methylamide,

(44) p-(p-Amidinophenoxycarbonyl)-α-methylcinnamic acid N-[2, 3-bis(ethoxycarbonyl)]phenylamide, (45) p-(p-Amidinophenoxycarbonyl)-α-methylcinnamic acid N-[2, 4-bis(ethoxycarbonyl)]phenylamide,

(46) p-(p-Amidinophenoxycarbonyl)-α-methylcinnamic acid N-[2, 5-bis(ethoxycarbonyl)]phenylamide,

(47) p-(p-Amidinophenoxycarbonyl)-α-methylcinnamic acid N-[2, 6-bis(ethoxycarbonyl)]phenylamide,

(48) p-(p-Amidinophenoxycarbonyl)-α-methylcinnamic acid N-[3, 4-bis(ethoxycarbonyl)]phenylamide,

(49) p-(p-Amidinophenoxycarbonyl)-α-methylcinnamic acid N-[3, 5-bis(ethoxycarbonyl)]phenylamide,

(50) p-(p-Amidinophenoxycarbonyl)-α-methylcinnamic acid N-(1-ethoxycarbonyl-3-benzyloxycarbonyl)-propylamide,

(51) p-(p-Amidinophenoxycarbonyl)-α-methylcinnamic acid N-(1-benzyloxycarbonyl-3-ethoxycarbonyl)propylamide,

(52) p-(p-Amidinophenoxycarbonyl)-α-methylcinnamic acid N-[1, 2-bis(ethoxycarbonyl)]ethylamide,

(53) p-(p-Amidinophenoxycarbonyl)-α-methylcinnamic acid N-(1-ethoxycarbonyl-2-benzyloxycarbonyl)ethylamide,

(54) p-(p-Amidinophenoxycarbonyl)-α-methylcinnamic acid N-(1-benzyloxycarbonyl-2-ethoxycarbonyl)ethylamide,

(55) p-(p-Amidinophenoxycarbonyl)-α-methylcinnamic acid N-[bis(ethoxycarbonyl)]methylamide,

(56) p-(p-Amidinophenoxycarbonyl)-α-methylcinnamic acid N-(1-ethoxycarbonyl-1-benzyloxycarbonyl)methylamide,

(57) p-(p-Amidinophenoxycarbonyl)-α-methylcinnamic acid N-[bis(ethoxycarbonylmethyl)]methylamide.

(58) p-(p-Amidinophenoxycarbonyl)-α-methylcinnamic acid N-(1-ethoxycarbonylmethyl-2-benzyloxycarbonyl)ethylamide,

(59) p-(p-Amidinophenoxycarbonyl)-α-methylcinnamic acid N-bis(1, 3-ethoxycarbonyl)-2-propenylamide,

(60) p-(p-Amidinophenoxycarbonyl)-α-methylcinnamic acid N-(1-ethoxycarbonyl-3-benzyloxycarbonyl)-2-propenylamide,

(61) p-(p-Amidinophenoxycarbonyl)-α-methylcinnamic acid N-(1-benzyloxycarbonyl-3-ethoxycarbonyl)-2-propenylamide,

(62) p-(p-Amidinophenoxycarbonyl)-α-methylcinnamic acid N-bis(1, 3-ethoxycarbonyl)-2-butenylamide,

(63) p-(p-Amidinophenoxycarbonyl)-α-methylcinnamic acid N-(1-ethoxycarbonyl-3-benzyloxycarbonyl)-2-butenylamide,

(64) p-(p-Amidinophenoxycarbonyl)-α-methylcinnamic acid N-(1-benzyloxycarbonyl-3-ethoxycarbonyl)-2-butenylamide,

(65) p-(p-Amidinophenoxycarbonyl)-α-methylcinnamic acid N-[bis(1,3-ethoxycarbonyl)-2-methyl]propenylamide,

(66) p-(p-Amidinophenoxycarbonyl)-α-methylcinnamic acid N-(1-ethoxycarbonyl-2-methyl-3-benzyloxycarbonyl)propenylamide,

(67) p-(p-Amidinophenoxycarbonyl)-α-methylcinnamic acid N-(1-benzyloxycarbonyl-2-methyl-3-ethoxycarbonyl)propenylamide,

(68) p-(p-Amidinophenoxycarbonyl)-α-methylcinnamic acid N-[ethoxycarbonyl-1-(3-quinolylmethyl)]methylamide,

(69) p-(p-Amidinophenoxycarbonyl)-α-methylcinnamic acid N-[1-ethoxycarbonyl-1-(3-carbazoylmethyl)]methylamide,

(70) p-(p-Amidinophenoxycarbonyl)-α-methylcinnamic acid N-carboxymethyl-N-phenylamide,

(71) p-(p-Amidinophenoxycarbonyl)-α-methylcinnamic acid N-carboxymethyl-N-phenylmethylamide,

(72) p-(p-Amidinophenoxycarbonyl)-α-methylcinnamic acid N-carboxymethyl-N-propargylamide,

(73) p-(p-Amidinophenoxycarbonyl)-α-methylcinnamic acid N-carboxymethyl-N-(4-ethoxycarbonylphenyl)-methylamide,

(74) p-(p-Amidinophenoxycarbonyl)-α-methylcinnamic acid N-ethoxycarbonyl-N-(4-carboxyphenyl)methylamide,

(75) p-(p-Amidinophenoxycarbonyl)-α-methylcinnamic acid N-carboxymethyl-N-(4-carboxyphenyl)methylamide,

(76) p-(p-Amidinophenoxycarbonyl)-α-methylcinnamic acid N-3-carboxy-2-propynyl-N-allylamide,

(77) p-(p-Amidinophenoxycarbonyl)-α-methylcinnamic acid N-3-methyl-2-butynyl-N-carboxymethylamide,

(78) p-(p-Amidinophenoxycarbonyl)-α-methylcinnamic acid N-3-ethoxycarbonyl-2-propynyl-N-carboxymethylamide,

(79) p-(p-Amidinophenoxycarbonyl)-α-methylcinnamic acid N-3-carboxy-2-propynyl-N-ethoxycarbonylmethylamide,

(80) p-(p-Amidinophenoxycarbonyl)-α-methylcinnamic acid N-3-carboxy-2-propynyl-N-carboxymethylamide,

(81) p-(p-Amidinophenoxycarbonyl)-α-methylcinnamic acid N-3-ethoxycarbonylpropyl-N-(1-carboxy-1-ethoxycarbonyl)methylamide,

(82) p-(p-Amidinophenoxycarbonyl)-α-methylcinnamic acid N-3-ethoxycarbonylpropyl-N-bis(carboxy)methylamide,

(83) P-(p-Amidinophenoxycarbonyl)-α-methylcinnamic acid N-3-carboxypropyl-N-bis(ethoxycarbonyl)methylamide,

(84) p-(p-Amidinophenoxycarbonyl)-α-methylcinnamic acid N-3-carboxypropyl-N-(1-ethoxycarbonyl-1-carboxy)methylamide,

(85) p-(p-Amidinophenoxycarbonyl)-α-methylcinnamic acid N-3-carboxypropyl-N-bis(carboxy)methylamide,

(86) p-(p-Amidinophenoxycarbonyl)-α-methylcinnamic acid N-3-carboxypropyl-N-allylamide,

(87) p-(p-Amidinophenoxycarbonyl)-α-methylcinnamic acid N-carboxymethyl-N-2,4-hexadienylamide,

(88) p-(p-Amidinophenoxycarbonyl)-α-methylcinnamic acid N-2-carboxyethyl-N-2-ethoxycarbonylethylamide,

(89) p-(p-Amidinophenoxycarbonyl)-α-methylcinnamic acid N,N-bis(2-carboxyethyl)amide,

(90) p-(p-Amidinophenoxycarbonyl)-α-methylcinnamic acid N-carboxymethyl-N-propylamide,

(91) p-(p-Amidinophenoxycarbonyl)-α-methylcinnamic acid N-(1-(S)-ethoxycarbonyl-2-carboxy)ethyl-N-2-ethoxycarbonylethylamide,
(92) p-(p-Amidinophenoxycarbonyl)-α-methylcinnamic acid N-(1-(S)-carboxy-2-ethoxycarbonyl)ethyl-N-2-ethoxycarbonylethylamide,
(93) p-(p-Amidinophenoxycarbonyl)-α-methylcinnamic acid N-(1-(S),2-bis(carboxy)ethyl)-N-2-ethoxycarbonylethylamide,
(94) p-(p-Amidinophenoxycarbonyl)-α-methylcinnamic acid N-(1-(S),2-bis(ethoxycarbonyl)ethyl)-N-2-carboxyethylamide,
(95) p-(p-Amidinophenoxycarbonyl)-α-methylcinnamic acid N-(1-(S)-ethoxycarbonyl-2-carboxy)ethyl-N-2-carboxyethylamide,
(96) p-(p-Amidinophenoxycarbonyl)-α-methylcinnamic acid N-(1-(S)-carboxy-2-ethoxycarbonyl)ethyl-N-2-carboxyethylamide,
(97) p-(p-Amidinophenoxycarbonyl)-α-methylcinnamic acid N-1-(S),2-bis(carboxy)ethyl-N-2-carboxyethylamide,
(98) p-(p-Amidinophenoxycarbonyl)-α-methylcinnamic acid N-(1-(S)-carboxy-3-ethoxycarbonyl)propylamide,
(99) p-(p-Amidinophenoxycarbonyl)-α-methylcinnamic acid N-(1-(S)-ethoxycarbonyl-3-carboxy)propylamide,
(100) p-(p-Amidinophenoxycarbonyl)-α-methylcinnamic acid N-1-(S),3-bis(carboxy)propylamide,
(101) p-(p-Amidinophenoxycarbonyl)-α-methylcinnamic acid N-(1-(S)-carboxy-2-ethoxycarbonyl)ethylamide,
(102) p-(p-Amidinophenoxycarbonyl)-α-methylcinnamic acid N-(1-(S)-ethoxycarbonyl-2-carboxy)ethylamide,
(103) p-(p-Amidinophenoxycarbonyl)-α-methylcinnamic acid N-1-(S),2-bis(carboxy)ethylamide,
(104) p-(p-Amidinophenoxycarbonyl)-α-methylcinnamic acid N-(1-(R)-carboxy-3-ethoxycarbonyl)propylamide,
(105) p-(p-Amidinophenoxycarbonyl)-α-methylcinnamic acid N-(1-(R)-ethoxycarbonyl-3-carboxy)propylamide,
(106) p-(p-Amidinophenoxycarbonyl)-α-methylcinnamic acid N-1-(R),3-bis(carboxy)propylamide,
(107) p-(p-Amidinophenoxycarbonyl)-α-methylcinnamic acid N-(1-(S)-carboxy-2-(ethoxycarbonylmethylthio))ethylamide,
(108) p-(p-Amidinophenoxycarbonyl)-α-methylcinnamic acid N-(1-(S)-ethoxycarbonyl-2-(carboxymethylthio))ethylamide,
(109) p-(p-Amidinophenoxycarbonyl)-α-methylcinnamic acid N-(1-(S)carboxy-2-(carboxymethylthio))ethylamide,
(110) p-(p-Amidinophenoxycarbonyl)-α-methylcinnamic acid N-(1-(S)-carboxy-3-benzyloxycarbonyl)propylamide,
(111) p-(p-Amidinophenoxycarbonyl)-α-methylcinnamic acid N-(1-(S)-benzyloxycarbonyl-3-carboxy)propylamide,
(112) p-(p-Amidinophenoxycarbonyl)-α-methylcinnamic acid N-(1-(S)-benzyloxycarbonyl-2-carboxy)ethylamide,
(113) p-(p-Amidinophenoxycarbonyl)-α-methylcinnamic acid N-(1-(S)-carboxy-2-benzyloxycarbonyl)ethylamide,
(114) p-(p-Amidinophenoxycarbonyl)-α-methylcinnamic acid N-(1-carboxy-4-ethoxycarbonyl)butylamide.
(115) p-(p-Amidinophenoxycarbonyl)-α-methylcinnamic acid N-(1-ethoxycarbonyl-4-carboxy)butylamide,
(116) p-(p-Amidinophenoxycarbonyl)-α-methylcinnamic acid N-1,4-bis(carboxy)butylamide,
(117) p-(p-Amidinophenoxycarbonyl)-α-methylcinnamic acid N-(1-carboxy-5-ethoxycarbonyl)pentylamide,
(118) p-(p-Amidinophenoxycarbonyl)-α-methylcinnamic acid N-(1-ethoxycarbonyl-5-carboxy)pentylamide,
(119) p-(p-Amidinophenoxycarbonyl)-α-methylcinnamic acid N-1,5-bis(carboxy)pentylamide,
(120) p-(p-Amidinophenoxycarbonyl)-α-methylcinnamic acid N-carboxymethylamide,
(121) p-(p-Amidinophenoxycarbonyl)-α-methylcinnamic acid N-(1-carboxymethyl-1-ethoxycarbonylmethyl)methylamide,
(122) p-(p-Amidinophenoxycarbonyl)-α-methylcinnamic acid N-1,1-bis(carboxymethyl)methylamide,
(123) p-(p-Amidinophenoxycarbonyl)-α-methylcinnamic acid N-(1-(S)-carboxy-2-(2-ethoxycarbonylethylthio))ethylamide,
(124) p-(p-Amidinophenoxycarbonyl)-α-methylcinnamic acid N-(1-(S)-ethoxycarbonyl-2-(2-carboxyethylthio))ethylamide,
(125) p-(p-Amidinophenoxycarbonyl)-α-methylcinnamic acid N-(1-(S)-carboxy-2-(2-carboxyethylthio))ethylamide,
(126) p-(p-Amidinophenoxycarbonyl)-α-methylcinnamic acid N-(1-(S)-carboxy-2-(3-ethoxycarbonylpropylthio))ethylamide,
(127) p-(p-Amidinophenoxycarbonyl)-α-methylcinnamic acid N-(1-(S)ethoxycarbonyl-2-(3-carboxypropylthio))ethylamide,
(128) p-(p-Amidinophenoxycarbonyl)-α-methylcinnamic acid N-(1-(S)-carboxy-2-(3-carboxypropylthio))ethylamide,
(129) p-(p-Amidinophenoxycarbonyl)cinnamic acid N-(1-(S)-carboxy-3-ethoxycarbonyl)propylamide,
(130) p-(p-Amidinophenoxycarbonyl)cinnamic acid N-(1-(S)-ethoxycarbonyl-3-carboxy)propylamide,
(131) p-(p-Amidinophenoxycarbonyl)cinnamic acid N-(1-(S),3-bis(carboxy)propyl)amide,
(132) p-(p-Amidinophenoxycarbonyl)-β-methylcinnamic acid N-(1-(S)-carboxy-3-ethoxycarbonyl)propylamide,
(133) p-(p-Amidinophenoxycarbonyl)-β-methylcinnamic acid N-(1-(S)-ethoxycarbonyl-3-carboxy)propylamide,
(134) p-(p-Amidinophenoxycarbonyl)-β-methylcinnamic acid N-(1-(S),3-bis(carboxy)propyl)amide;
and N-benzyl, N-allyl and N-propargyl compounds corresponding to compounds (33) to (66) and (99) to (134) hereinbefore described; and
(135) p-(p-Amidinophenoxycarbonyl)-α-methylcinnamic acid N-(2-ethoxycarbonylperhydroazepinyl)amide,
(136) p-(p-Amidinophenoxycarbonyl)-α-methylcinnamic acid N-(2-ethoxycarbonylpiperidino)amide;
and further the compounds prepared in Examples hereinafter described.

Acid Addition Salts

The compounds of the formula (I), of the present invention may be converted into the corresponding acid addition salts by known method. Non toxic and water-soluble salts are preferable. Suitable acid addition salts include the salts with inorganic acids such as hydrochloric acid, hydrobromic acid, sulfuric acid, phosphonic acid and nitric acid, and the salts with organic acids such as acetic acid, trifluoroacetic acid, lactic acid, tartaric acid, oxalic acid, fumaric acid, maleic acid, citric acid, benzoic acid, methanesulfonic acid, ethanesulfonic acid, benzenesulfonic acid, toluenesulfonic acid, isethionic acid, glucuronic acid and gluconic acid.

Processes for the Preparation thereof

In the compounds of the formula (I), of the present invention, those in which all of $R^7$, $R^8$, $R^9$ and $R^{10}$, in $R^3$, represent groups not containing COOH and COOt-Bu, i.e., the compounds of the formula (Ia):

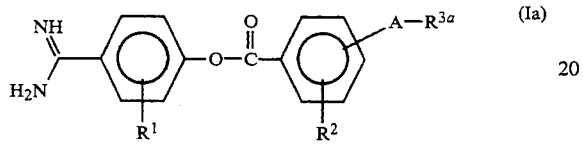

wherein $R^1$, $R^2$ and A are the same meanings as hereinbefore defined, and $R^{3a}$ is the same meaning as hereinbefore defined for $R^3$, provided that all of $R^7$, $R^8$ $R^9$ and $R^{10}$, in $R^3$, are groups not containing COOH and COOt-Bu, may be prepared by esterification of a compound of the formula (IIa):

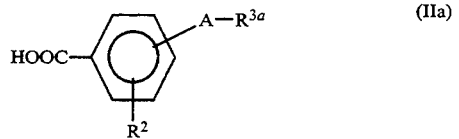

wherein $R_2$, $R_{3a}$ and A are the same meanings as hereinbefore defined, with a compound of the formula (III):

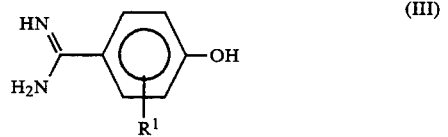

wherein $R_1$ is the same meaning as hereinbefore defined. The said esterification is known and can be carded out by methods for example:

(1) using an acid halide,
(2) using a mixed acid anhydride,
(3) using a condensing agent etc.

Each of these methods can be carried out, for example, as follows:

(1) the method using an acid halide may be carded out, for example, by reacting a carboxylic acid with an acid halide (e.g., oxalyl chloride, thionyl chloride etc.) in an inert organic solvent (e.g., chloroform, methylene chloride, diethyl ether, tetrahydrofuran etc.) or without a solvent at from −20° C. to the reflux temperature of the solvent, and then by reacting the acid halide obtained with a corresponding alcohol in the presence of a tertiary amine (e.g., pyridine, triethylamine, dimethylaniline, dimethylaminopyridine etc.) in an inert organic solvent (e.g., chloroform, methylene chloride, diethyl ether, tetrahydrofuran etc.), at a temperature of from 0° C. to 40° C., (2) the method using a mixed acid anhydride may be carried out, for example, by reacting a carboxylic acid and an acid halide (e.g., pivaloyl chloride, tosyl chloride, mesyl chloride etc.) or an acid derivative (e.g., ethyl chloroformate, isobutyl chloroformate etc.) in the presence of a tertiary amine (e.g., pyridine, triethylamine, dimethylaniline, dimethylaminopyridine etc.)in an inert organic solvent (e.g., chloroform, methylene chloride, diethyl ether, tetrahydrofuran etc. ) or without a solvent at a temperature of from 0° C. to 40° C., and then by reacting the mixed acid anhydride obtained with a corresponding alcohol in an inert organic solvent (e.g., chloroform, methylene chloride, diethyl ether, tetrahydrofuran etc.), at a temperature of from 0° C. to 40° C., and (3) the method using a condensing agent (e.g., 1,3-dicyclohexylcarbodiimide (DCC), 1-ethyl-3-[3-(dimethylamino)propyl]carbodiimide (EDC), 2-chloro-1-methylpyridinium iodide etc. ) may be carded out, for example, by reacting a carboxylic acid with a corresponding alcohol using a condensing agent in the presence or absence of a teritiary amine (e.g., pyridine, triethylamine, dimethylaniline, dimethylaminopyridine etc.) in an inert organic solvent (e.g., chloroform, methylene chloride, dimethyl formamide,diethyl ether etc.) or without a solvent at a temperature of from 0° C. to 40° C.

The reactions (1), (2) and (3) hereinbefore described may be preferably carried out in an atmosphere of inert gas (e.g., argon, nitrogen etc.) under anhydrous conditions.

In the compounds of the formula (I), those in which at least one group of $R^7$, $R^8$ and $R^9$, in $R^3$, represents a group containing COOt-Bu and the other groups represent ones not containing COOH, or $R^{10}$ represents COOt-Bu, i.e., the compounds of the formula (Ib):

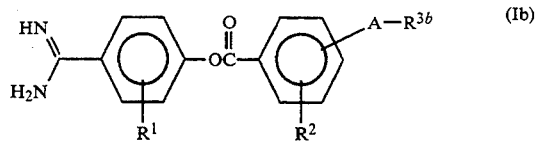

wherein $R^1$, $R^2$ and A are the same meanings as hereinbefore defined and $R^{3b}$ is the same meaning as hereinbefore defined for $R^3$, provided that at least one group of $R^7$, $R^8$ and $R^9$, in $R^3$, is a group containing COOt-Bu and the other groups are ones not containing COOH, or $R^{10}$ is COOt-Bu, may be prepared by amidation of a compound of the formula (IIb):

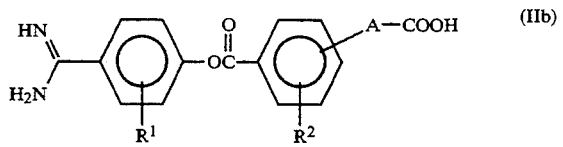

wherein the various symbols are the same meanings as hereinbefore defined, with a compound of the formula (IIIb):

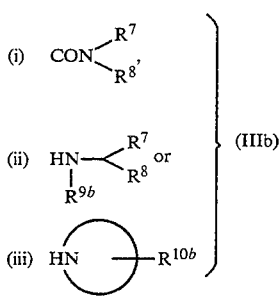

wherein $R^{7b}$, $R^{8b}$, $R^{9b}$ and $R^{10b}$ are the same meanings as hereinbefore defined for $R^7$, $R^8$ $R^9$ and $R^{10}$, respectively, provided that at least one group of $R^{7b}$, $R^{8b}$ and $R^{9b}$ is a group containing COOt-Bu and the other groups are ones not containing COOH, or $R^{10b}$ is COOt-Bu. The said amidation can be carried out by the same condition as hereinbefore described for the esterification using an amine of the formula (IIIb) instead of an alcohol of the formula (III).

In the compounds of the formula (I), those in which at least one group of $R^7$, $R^8$ and $R^9$, in $R^3$, represents a group containing COOH and the other groups represent ones not containing COOt-Bu, or $R^{10}$ represents COOH, i.e., the compounds of the formula (Ic):

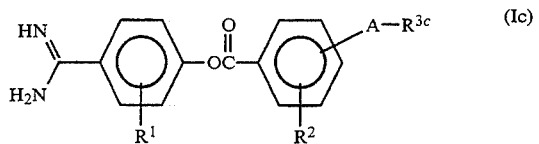

wherein $R^1$, $R^2$ and A are the same meanings as hereinbefore defined and $R^{3c}$ is the same meaning as hereinbefore defined for $R^3$, provided that at least one group of $R^7$, $R^8$ and $R^9$, in $R^3$, is a group containing COOH and the other groups are ones not containing COOt-Bu, or $R^{10}$ is COOH, may be prepared by the hydrolysis of t-butyl ester group, of a compound of the formula (Ib) in which the various symbols are the same meanings as hereinbefore defined. The hydrolysis of t-butyl ester group may be carried out, for example, by using an organic acid (e.g., trifluoroacetic acid etc.) or an inorganic acid (e.g., hydrochloric acid etc.), or the mixture thereof, in an inert organic solvent (e.g., methylene chloride, chloroform, methanol, dioxane, ethyl acetate, anisole etc.) at a temperature of from 0° C. to 90° C.

In the compounds of the formula (IIa), those in which all of $R^7$, $R^8$ and $R^9$, in $R^{3a}$, represent groups not containing benzyloxycarbonyl, allyloxycarbonyl and propargyloxycarbonyl, or $R^{10}$ in $R^{3a}$ represents a group other than benzyloxycarbonyl, i.e., the compounds of the formula (IIa-1):

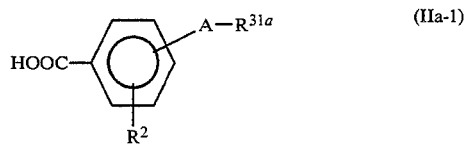

wherein $R^2$ and A are the same meanings as hereinbefore defined and $R^{31a}$ is the same meaning as hereinbefore defined for $R^{3a}$, provided that all of $R^7$, $R^8$ and $R^9$, in $R^{3a}$, are groups not containing benzyloxycarbonyl, allyloxycarbonyl and propargyloxycarbonyl, or $R^{10}$ in $R^{3a}$ is not benzyloxycarbonyl, may be prepared by methods known per se, for example, by a series of reactions depicted in the following Scheme A.

In the Scheme A, $R^2$, A and $R^{31a}$ are the same meanings as hereinbefore defined and $R^{71a}$, $R^{81a}$ and $R^{91a}$ are the same meanings as hereinbefore defined for $R^7$, $R^8$ and $R^9$, respectively, provided that all of $R^7$, $R^8$ and $R^9$ are groups not containing benzyloxycarbonyl, allyloxycarbonyl and propargyloxycarbonyl, or $R^{101a}$ is the same meaning as hereinbefore defined for $R^{10}$, provided that $R^{10}$ is not benzyloxycarbonyl.

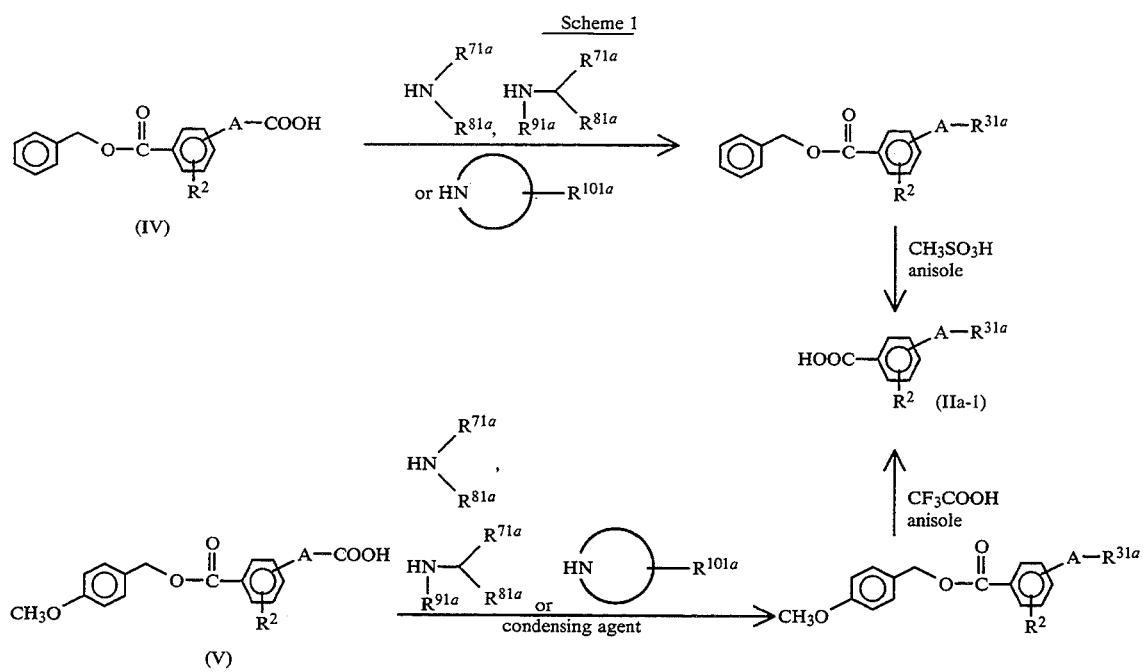

In the compounds of the formula (IIa), those in which at least one group of $R^7$, $R^8$ and $R^9$, in $R^{3a}$, represents a group containing benzyloxycarbonyl, allyloxycarbonyl or propargyloxycarbonyl, or those in which $R^{10}$ in $R^{3a}$ represents benzyloxycarbonyl, i.e., the compounds of the formula (IIa-2):

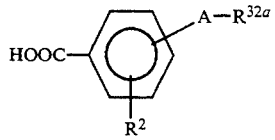
(IIa-2)

wherein $R^2$ and A are the same meanings as hereinbefore defined and $R^{32a}$ is the same meaning as hereinbefore defined for $R^{3a}$, provided that at least one group of $R^7$, $R^8$ and $R^9$, in $R^{3a}$, is a group containing benzyloxycarbonyl, allyloxycarbonyl or propargyloxycarbonyl, or $R^{10}$ in $R^{3a}$ is benzyloxycarbonyl, may be prepared by methods known per se, for example, by a series of reactions depicted in the following Scheme B.

In the Scheme B, $R^2$, A and $R^{32a}$ are the same meanings as hereinbefore defined and $R^{72a}$, $R^{82a}$ and $R^{92a}$ are the same meanings as hereinbefore defined for $R^7$, $R^8$ and $R^9$, respectively, provided that at least one group of $R^7$, $R^8$ and $R^9$ is a group containing benzyloxycarbonyl, allyloxycarbonyl or propargyloxycarbonyl, and $R^{102a}$ is benzyloxycarbonyl.

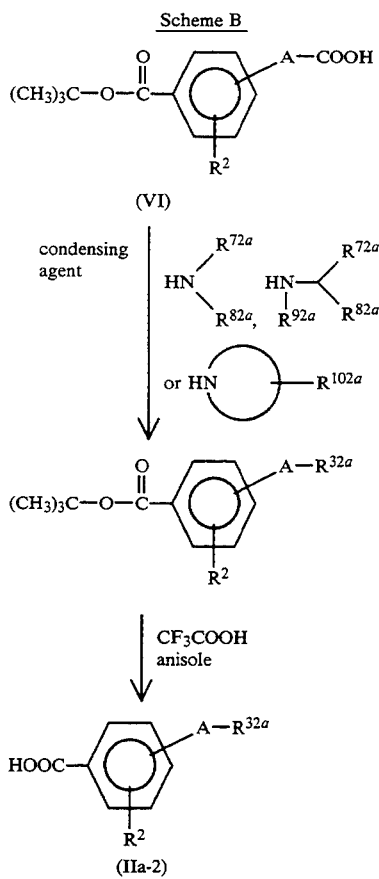

The compounds of the formula (IIb) may be prepared by methods known per se, for example, by a seried of reactions depicted in the following Scheme C.

In the Scheme C, A, $R^1$ and $R^2$ are the same meanings as hereinbefore defined.

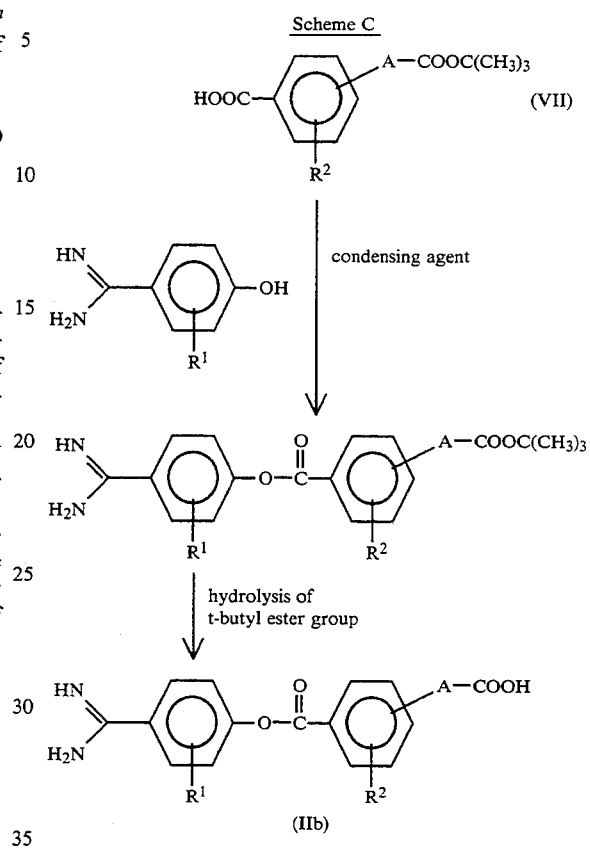

In the Scheme A, B and C,
$CH_3SO_3H$ is methanesulfonic acid,
$CF_3COOH$ is trifluoroacetic acid.

The reactions in schemes hereinbefore depicted may be carried out by methods known per se. The compounds of the formulae (IV), (V), (VI) and (VII) used as starting materials in the schemes hereinbefore depicted, are known per se or may be easily prepared by methods known per se.

In each reaction in the present specification, products may be purified by conventional manner. For example, it may be carried out by distillation of atmospheric or reduced pressure, high performance liquid chromatography, thin layer chromatography or column chromatography using silica gel or magnesium silicate, washing or recrystallization. Purification may be carried out after each reaction, or after a series of reactions.

Other starting materials and each reagents are known per se or may be prepared by known methods.

Pharmacological Activity

It has been confirmed that the compounds of the formula (I), of the present invention have inhibitory activities on $PLA_2$ and on various proteases such as trypsin, plasmin, thrombin, kallikrein, especially trypsin. For example, in laboratory tests the following results were obtained.

Method (1) Inhibitory activity on $PLA_2$

A reaction solution including 50 mM tris-HCl buffer (pH7.5, 874 μl; containing 100 mM sodium chloride, 1 mM EDTA), 1M calcium chloride (6 μl), 1% bovine serum albumin (10 μl) and 2.5 mM 10PY-PC (10 μl), was prepared. To the solution were added a test compound in various concentration or water (50 μl), and a solution of 10 mU/ml PLA$_2$ (derived from hog pancreas)(50 μl). The appearance of fluorescence was measured (Ex=345 nm, Em=396 nm), Percentage (%) of the strength of fluorescence in the presence of a test compound was calculated when the strength of that in the absence thereof was regarded as 100%, and therefrom IC$_{50}$ value was calculated. The results are shown in the following Table 1.

TABLE 1

| Inhibitory Activity on PLA$_2$ | |
|---|---|
| Compound (Example No.) | IC$_{50}$ (μM) |
| 1 | 4.8 |
| 1 (d) | 63 |
| 1 (g) | 5.3 |
| 1 (i) | 28 |
| 1 (k) | 3.1 |
| 1 (t) | 24 |
| 2 (a) | 15 |
| 2 (f) | 32 |

(2) Inhibitory activity on trypsin

To a mixture of a 0.2M HEPES.sodium hydroxide buffer solution (pH8.0, 100 μl) and distilled water (640 μl), were added a test compound in various concentration or water (10 μl), and a solution of 80 mU/ml trypsin (derived from bovine pancreas) (50 μl) and then the mixture was preincubated for one minute at 30° C. To the solution thus obtained was added 2.5 mM BAPNA (200 μl) and the mixture was incubated for 30 min. The absorbance at 405 nm was measured. Percentage (%) of the absorbance in the presence of a test compound was calculated when the absorbance in the absence thereof was regarded as 100%, and therefrom IC$_{50}$ value was calculated. The results are shown in the following Table 2.

TABLE 2

| Inhibitory Activity on trypsin | |
|---|---|
| Compound (Example No.) | IC$_{50}$ (μM) |
| 1 | 0.14 |
| 1 (d) | 0.13 |
| 1 (g) | 0.14 |
| 1 (i) | 0.13 |
| 1 (k) | 0.22 |
| 1 (p) | 0.15 |
| 1 (t) | 0.22 |
| 2 (a) | 0.14 |
| 2 (f) | 0.14 |
| 4 | 0.10 | in the methods hereinbefore described.

10PY-PC represents 3'-palmitoyl-2-(1-pyrenedecanoyl)-L-α-phosphatidylcholine,

HEPES represents 4-(2-hydroxyethyl)-1-piperazineethanesulfonic acid, and

BAPNA represents α-N-benzoyl-DL-arginine-p-nitroanilide hydrochloride.

The toxicity of the compounds of the present invention is very weak. Therefore, the compounds of the present invention may be considered to be sufficiently safe and suitable for pharmaceutical use.

Application for pharmaceuticals

The inhibition of PLA$_2$ and on various proteases such as trypsin, plasmin, thrombin, kallikrein, especially trypsin in mammals including human beings, especially human beings are useful for the prevention and/or the treatment of various inflammatory diseases, allergic diseases, disseminated intravascular coagulation, pancreatitis, severity in pancreatitis and multiple organ failure.

For the purpose hereinbefore described, the compounds of the formula (I), of the present invention, non-toxic acid addition salts thereof, or hydrates thereof may be normally administered systematically or partially, usually by oral or parenteral administration.

The doses to be administered are determined depending upon age, body weight, symptom, the desired therapeutic effect, the route of administration, and the duration of the treatment etc. In the human adult, the doses per person per dose are generally between 1 mg and 1000 mg by oral administration, up to several times per day, and between 1 mg and 100 rag, by parenteral administration (preferably, intravenously) up to several times per day, or continuous administration between 1 and 24 hrs. per day from vein.

As mentioned above, the doses to be used depend upon various conditions. Therefore, there are cases in which doses lower than or greater than the ranges specified above may be used.

When administering the compounds of the present invention, it is used in the form of solid compositions, liquid compositions or other compositions for oral administration, or as injections, liniments or suppositories etc. for parenteral administration.

Solid compositions for oral administration include compressed tablets, pills, capsules, dispersible powders, and granules. Capsules include hard capsules and soft capsules.

In such compositions, one or more of the active compound(s) is or are admixed with at least one inert diluent (such as lactose, mannitol, glucose, hydroxypropyl cellulose, microcrystalline cellulose, starch, polyvinylpyrrolidone, magnesium metasilicate aluminate, etc.). The compositions may also comprise, as in normal practice, additional substances other than inert diluents: e.g. lubricating agents (such as magnesium stearate etc.), disintegrating agents (such as cellulose calcium glycolate, etc.), stabilizing agents (such as lactose, etc.), and assisting agents for dissolving (such as glutamic acid, asparaginic acid etc.).

The tablets or pills may, if desired, be coated with a film of gastric or enteric material (such as sugar, gelatin, hydroxypropyl cellulose or hydroxypropylmethyl cellulose phtalate etc.), or be coated with more than two films. And further, coating may include containment within capsules of absorbable materials such as gelatin.

Liquid compositions for oral administration include pharmaceutically-acceptable emulsions, solutions, suspensions, syrups and elixirs. The compositions may also comprise inert diluents commonly used in the art (purified water, ethanol etc.). Besides inert diluents, such compositions may also comprise adjuvants (such as wetting agents, suspending agents, etc)., sweetening agents, flavoring agents, perfuming agents, and preserving agents.

Other compositions for oral administration include spray compositions which may be prepared by known methods and which comprise one or more of the active compound(s). Spray compositions may comprise additional substances other than inert diluents: e.g. stabilizing agents (sodium sulfate etc.), isotonic buffer (sodium chloride, sodium citrate, citric acid, etc.). For preparation of such spray compositions, for example, the method described in the U.S. Pat. No. 2,868,691 or 3,095,355 (herein incorporated in their entireties by reference) may be used.

Injections for parenteral administration include sterile aqueous or non-aqueous solutions, suspensions and emulsion. In such compositions, one more of active compound(s) is or are admixed with at least one of inert aqueous diluent(s) (distilled water for injection, physiological salt solution etc.) or inert non-aqueous diluent(s) (propylene glycol, polyethylene glycol, olive oil, ethanol, POLYSORBATE80 (registered trade mark) etc.).

Injections may comprise additional other than inert diluents: e.g. preserving agents, wetting agents, emulsifying agents, dispersing agents, stabilizing agent (lactose etc.), assisting agents such as assisting agents for dissolving (glutamic acid, asparaginic acid etc.).

They may be sterilized for example, by filtration through a bacteria-retaining filter, by incorporation of sterilizing agents in the compositions or by irradiation. They may also be manufactured in the form of sterile solid compositions, for example, by freeze-drying, and which may be dissolved in sterile water or some other sterile diluent(s) for injection immediately before use.

Other compositions for parenteral administration include endermic ones such as liquids for external use, ointment, and endermic liniments, and suppositories and pessaries for intrarectal administration which comprise one or more Of the active compound(s) and may be prepared by per se known methods.

EXAMPLES

The following reference examples and examples illustrate, but not limit, the present invention.

The solvents in parentheses show the developing or eluting solvents and the ratios of the solvents used are by volume in chromatographic separations.

Unless otherwise specified, "IR" was measured by KBr method, and "NMR" was measured in a solution of deuteromethanol.

Reference Example 1 p-Benzyloxycarbonyl-α-methylcinnamic acid t-butyl ester

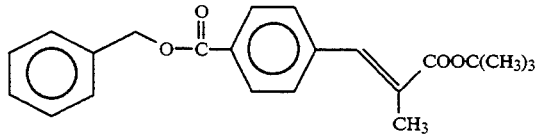

To a suspension of sodium hydride (0.8 g, containing 60% oil) in tetrahydrofuran (25 ml) was added slowly dropwise a solution of 2-(diethylphosphono) propionic acid t-butyl ester (4.8 g) in tetrahydrofuran (6 ml) under cooling with ice, and the mixture was stirred for 30 min. at room temperature. After the reaction mixture was cooled with ice, a solution of p-benzyloxycarbonylbenzaldehyde (4.0 g) in tetrahydrofuran (15 ml) was added slowly dropwise thereto. The mixture was stirred for 30 min. at room temperature, water was added thereto, and then the reaction mixture was extracted with ethyl acetate. The extract was washed with water, a saturated aqueous solution of sodium bicarbonate and a saturated aqueous solution of sodium chloride, successively, dried over anhydrous magnesium sulfate, and evaporated. The residue was purified by silica gel column chromatography (hexane:ethyl acetate=20:1→15:1) to give the title compound (5.2 g) having the following physical data:

TLC: Rf 0.34 (hexane:ethyl acetate=10:1 ).

Reference Example 2 p-Benzyloxycarbonyl-α-methylcinnamic acid

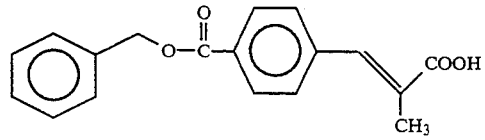

To a solution of the compound prepared in Reference Example 1 (56.0 g) in anisole (40 ml) was added trifluoroacetic acid (75 ml) under cooling with ice. After stirred for two hours at room temperature, the reaction mixture was concentrated under reduced pressure. Thus obtained white solid was washed with isopropyl ether, filtered, and dried under reduced pressure to give the title compound (39.57 g) as white crystal having the following physical data:

TLC: Rf 0.26 (hexane:ethyl acetate:acetic acid=12:4:1).

Reference Example 3 p-(Benzyloxycarbonyl)acetophenone

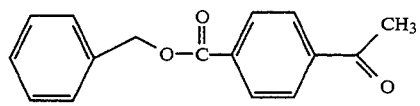

To a solution of p-acetylbenzoic acid (16.4 g) in dimethylformamide (100 ml) were added successively potassium carbonate (27.6 g) and benzyl bromide (13 ml). The mixture was stirred for 13 hours at room temperature. After quenched by addition of water, the reaction mixture was extracted with a mixture of hexane and ethyl acetate (3:1). The extract was washed with a saturated aqueous solution of sodium chloride, dried over anhydrous magnesium sulfate, and evaporated. The residue was purified by silica gel column chromatography (hexane:ethyl acetate=9:1-6:1) to give the title compound (16 g) having the following physical data:

TLC: Rf 0.63 (hexane:ethyl acetate:acetic acid=2:4:1).

Reference Example 4 p-(Benzyloxycarbonyl)-β-methylcinnamic acid

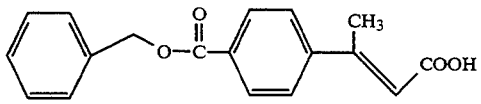

By the same procedure as a series of reactions of Reference Example 1→Reference Example 2, using the compound prepared in Reference Example 3 instead of p-benzyloxycarbonylbenzaldehyde, the title compound having the following physical data was given:

TLC: Rf 0.45 (hexane:ethyl acetate:acetic acid=12:4:1).

Reference Example 5 p-(t-Butoxycarbonyl)benzaldehyde

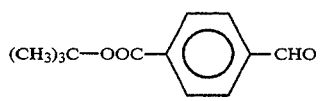

To a solution of p-(t-butoxycarbonyl)benzoic acid (13.32 g) in tetrahydrofuran (100 ml) and triethylamine (10 ml), was added slowly dropwise ethyl chloroformate (6.8 ml) under cooling with ice, under an atmosphere of argon. After the mixture was stirred for two hours at room temperature, triethylamine,hydrochloride precipitated was filtered off. To the filtrate thus obtained were added slowly sodium borohydride (4.54 g) and water (20 ml) under cooling with ice. After stirred for one hour at room temperature, the reaction mixture was quenched by addition with water. The reaction mixture was extracted with a mixture of hexane and ethyl acetate (1:1). The extract was washed with a saturated aqueous solution of sodium bicarbonate and a saturated aqueous solution of sodium chloride, successively, dried over anhydrous magnesium sulfate, and evaporated. The residue was purified by silica gel column chromatography (hexane:ethyl acetate=10:1→4:1).

To a solution of p-(t-butoxycarbonyl)benzyl alcohol (7.28 g) thus obtained in dimethyl sulfoxide (90 ml) and triethylamine (25 ml) was added a solution of sulfur trioxide-pyridine complex (19.75 g) in dimethyl sulfoxide (70 ml). After stirred for 30 min. at room temperature, the reaction mixture was quenched by addition of water. The reaction mixture was acidified by addition of 1N hydrochloric acid, and then extracted with a mixture of hexane and ethyl acetate (3:1). The extract was washed with a saturated aqueous solution of sodium bicarbonate and a saturated aqueous solution of sodium chloride, dried over anhydrous magnesium sulfate and evaporated to give the title compound (7.2 g) having the following physical data:

TLC: Rf 0.59 (hexane:ethyl acetate=2:1).

Reference Example 6 p-(t-Butoxycarbonyl)-α-methylcinnamic acid ethyl ester

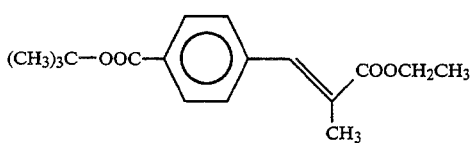

By the same procedure as Reference Example 1, using the compound prepared in Reference Example 5 instead of p-benzyloxycarbonylbenzaldehyde, the title compound having the following physical data was given:

TLC: Rf 0.58 (hexane: ethyl acetate=4:1).

Reference Example 7 p-(t-Butoxycarbonyl)-α-methylcinnamic acid

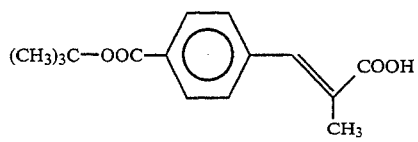

To a solution of the compound prepared in Reference Example 6 (8.1 g) in ethanol (60 ml) was added 5N aqueous solution of sodium hydroxide (6 ml) under cooling with ice. After stirred overnight at room temperature, the reaction mixture was quenched by addition of 2N hydrochloric acid (15 ml), and then evaporated till the volume of the solution became ½. An aqueous solution thus obtained was extracted with ethyl acetate. The extract was washed with a saturated aqueous solution of sodium chloride, dried over anhydrous magnesium sulfate and evaporated to give the title compound (7.3 g) having the following physical data:

TLC: Rf 0.41 (hexane:ethyl acetate:acetic acid=12:6:1).

Reference Example 8 p-(p-Methoxybenzyloxycarbonyl)cinnamic acid

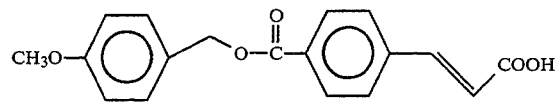

To a solution of (p-carboxy)benzaldehyde (15 g) in dimethylformamide (200 ml) were added successively potassium carbonate (27.6 g) and p-methoxybenzyl chloride (15 ml). After stirred for 17 hours at room temperature, the reaction mixture was quenched by addition of water and then extracted twice with a mixture of hexane and ethyl acetate (2:1). The extract was washed with a saturated aqueous solution of sodium chloride, dried over anhydrous magnesium sulfate, and evaporated. To a solution of the aldehyde compound thus obtained in pyridine (100 ml) were added successively malonic acid (20.8 g) and piperidine (5 ml). After stirred for one hour at 80° C., the reaction mixture was quenched by addition of ice-water, and then neutralized by addition of 1N hydrochloric acid. The crystals thus obtained were filtered, washed with water and ether, successively, and then dried to give the title compound (17.4 g) as white solid having the following physical data:

TLC: Rf 0.37 (chloroform: methanol=9:1).

Reference Example 9 p-Benzyloxycarbonyl-α-methylcinnamic acid N-ethoxycarbonylmethyl-N-phenylmethylamide

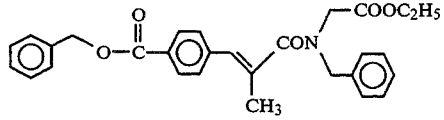

A suspension of the compound prepared in Reference Example 2 (4 g) in methylene chloride (15 ml) was added oxalyl chloride (5.8 ml) at room temperature. The mixture was stirred for one hour at room temperature and then evaporated. A solution of acid chloride thus obtained, in methylene chloride (20 ml) was added slowly dropwise to a solution of N-ethoxycarbonyl-methyl-N-phenylmethylamine (2.61 ml) in a mixture of methylene chloride (28 ml) and pyridine (2.2 ml) under cooling with ice. The reaction mixture was stirred for 30 min. at room temperature, water was added thereto and then the reaction mixture was extracted with ether. The extract was washed with 1N hydrochloric acid, 1N aqueous solution of sodium hydroxide and a saturated aqueous solution of sodium chloride, successively, dried over anhydrous magnesium sulfate, and evaporated. The residue was purified by silica gel column chromatography (hexane:ethyl acetate=9:1→3:1) to give the title compound (5.78 g) having the following physical data:

TLC: Rf 0.39 (hexane:ethyl acetate=2:1).

Reference Example 10 p-Carboxy-α-methylcinnamic acid N-ethoxycarbonyl-methyl-N-phenylmethylamide

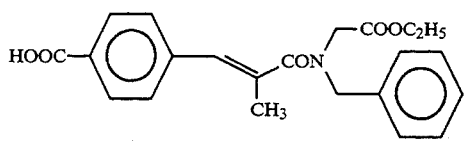

To a solution of the compound prepared in Reference Example 9 (5.7 g) in anisole (60 ml), was added methanesulfonic acid (33 ml) under cooling with ice. The reaction mixture was stirred for two hours at room temperature and evaporated. To the residue were added ice-water and ether, and the mixture was separated into two layers. The organic layer was further extracted with water and a saturated aqueous solution of sodium bicarbonate. All aqueous layers were collected and were acidified by addition of 1N hydrochloric acid under cooling with ice, and then extracted with ethyl acetate. The extract was washed with water and a saturated aqueous solution of sodium chloride, successively, dried over anhydrous magnesium sulfate, and evaporated to give the title compound (3.79 g) having the following physical data:

TLC: Rf 0.18 (hexane:ethyl acetate:acetic acid=12:4:1).

Reference Example 11 p-(p-methoxybenzyloxycarbonyl)cinnamic acid N'-phenylmethylpiperazinylamide

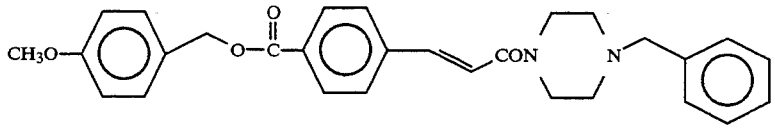

To a solution of the compound prepared in Reference Example 8 (4.22 g) in dimethylformamide (40 ml), were added successively N-benzylpiperazine (2.35 ml) and 1-ethyl-3-[-3-(dimethylamino)propyl]carbodiimide (3.1 g). After the reaction mixture was stirred for two hours at room temperature, ice-water was added thereto. The mixture was extracted with ethyl acetate. The extract was washed with water and a saturated aqueous solution of sodium chloride, successively, dried over anhydrous magnesium sulfate and evaporated. The residue was purified by silica gel column chromatography (hexane:ethyl acetate=2:→1:2) to give the title compound (3.4 g) having the following physical data:

TLC: Rf 0.67 (ethyl acetate).

Reference Example 12 p-Carboxycinnamic acid N'-phenylmethylpiperazinylamide hydrochloride

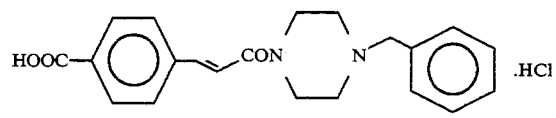

By the same procedure as Reference Example 2, using the compound prepared in Reference Example 11 instead of that prepared in Reference Example 1, the free compound of the title compound was obtained. The free compound was convened into the corresponding hydrochloride salt by a conventional manner to give the title compound having the following physical data:

TLC: Rf 0.21 (ethyl acetate).

Reference Example 13 p-(t-Butoxycarbonyl)cinnamic acid

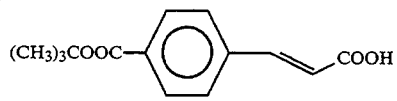

To a solution of p-(t-butoxycarbonyl)benzaldehyde (4.05 g) in pyridine (16 ml), were added successively malomic acid (4.16 g) and piperidine (0.6 ml). The reaction mixture was stirred for four hours at 80° C., and then diluted with ethyl acetate. The mixture was washed with water and a saturated aqueous solution of sodium chloride, successively, dried over anhydrous magnesium sulfate and evaporated. The residue thus obtained was washed with n-hexane and dried to give the title compound (4.65 g) having the following physical data:

TLC: Rf 0.28 (hexane:ethyl acetate:acetic acid=2:1:1 drop).

Reference Example 14

3-(p-(t-butoxycarbonyl)phenyl)propionic acid

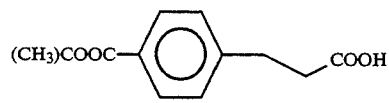

To a solution of the compound prepared in Reference Example 12 (4.65 g) in a mixture of methanol (50 ml) and chloroform (50 ml) was added 10% palladium-carbon (0.5 g). The mixture was stirred overnight at room temperature under an atmosphere of hydrogen. The catalyst was filtered off and the solution was evaporated. To a solution of the residue thus obtained, in dioxane (30 ml) was added 1N aqueous solution of sodium hydroxide (20 ml) and the mixture was stirred for one hour at 50° C. The reaction mixture was concentrated and the residue thus obtained was washed with n-hexane and then dried to give the title compound (3.67 g) having the following physical data:

TLC: Rf 0.14 (hexane:ethyl acetate=2:1).

Example 1 p-(p-Amidinophenoxycarbonyl)-α-methylcinnamic acid N-ethoxycarbonylmethyl-N-phenylmethylamide hydrochloride

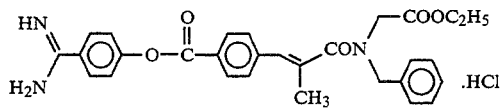

To a solution of the compound prepared in Reference Example 10 (2.67 g) in pyridine (35 ml), were added successively p-amidinophenol hydrochloride (1.21 g) and 1,3-dicyclohexylcarbodiimide (1.73 g). After stirred overnight at room temperature, the reaction mixture was filtered. The filtrate was evaporated. The residue was purified by silica gel column chromatography (chloroform:methanol:acetic acid=30:2:1) to give the title compound (2.29 g) as white powder having the following physical data:

TLC: Rf 0.43 (chloroform:methanol:acetic acid=15:2:1); IR: $\nu$3352, 1741, 1678, 1606, 1480, 1411, 1375, 1267, 1214, 1176, 1067, 1015, 976, 888, 736, 699, 630, 521 cm$^{-1}$; NMR: $\delta$8.10 (2H, d, J=8.0 Hz), 7.95 (2H, d, J=8.0 Hz), 7.55 (4H, brd, J=7.5 Hz), 7.40 (5H, brs), 6.75 (1H, brs), 4.82–4.70 (2H, m), 4.21–4.00 (4H, m), 2.15 (3H, s), 1.35–1.20 (3H, m).

Example 1(a)~(vvv)

By the same procedure as a series of reactions of Reference Example 9→Reference Example 10→Example 1, using, as starting materials, the compound prepared in Reference Example 2, that prepared in Reference Example 4 p-benzyloxycarbonylbenzoic acid or p-methoxycarbonylbenzoic acid, using proper amines instead of N-ethoxycarbonylmethyl-N-phenylmethylamine, and further using P-amidimophenol or its derivatives, the compounds of the present invention shown in Table 3 were given.

TABLE 3

| Ex. No. | Structure | Name | TLC (Rf) | NMR |
|---|---|---|---|---|
| 1(a) | 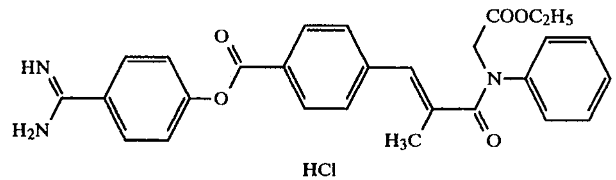 | p-(p-amidino-phenoxycarbonyl)-α-methylcinnamic acid N-ethoxy-carbonylmethyl-N-phenylamide hydrochloride | 0.54 (chloroform:methanol:acetic acid = 15:2:1) | 8.10(2H, d), 7.90(2H, d), 7.50(2H, d), 7.45–7.30(5H, m), 7.25(2H, d), 6.68(1H, brs), 4.55(2H, s), 4.22(2H, q), 1.90 (3H, d), 1.30(3H, t,). |
| 1(b) | 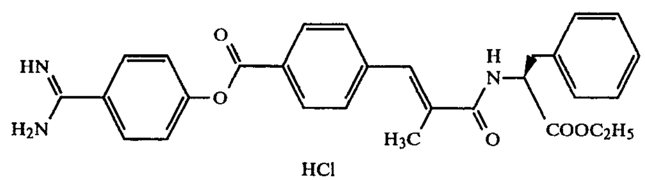 | p-(p-amidino-phenoxycarbonyl)-α-methylcinnamic acid N-((1-(S)-ethoxycarbonyl-2-phenyl)ethyl)amide hydrochloride | 0.43 (chloroform:methanol:acetic acid = 15:2:1) | 8.10(2H, d), 7.95(2H, d), 7.58 (2H, d), 7.57(2H, d), 7.30 (5H, brs), 7.18(1H, brs), 4.75 (1H, dd), 4.20(2H, q), 3.25 (1H, dd), 3.10(1H, dd), 2.04 (3H, brs), 1.22(3H, t). |
| 1(c) | 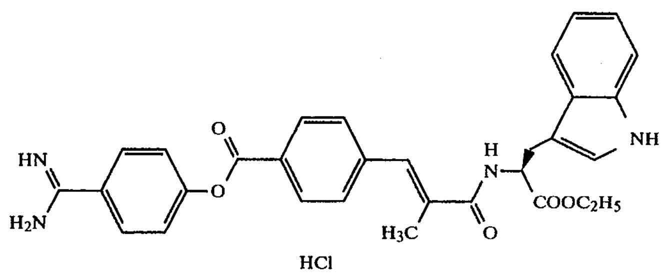 | p-(p-amidino-phenoxycarbonyl)-α-methylcinnamic acid N-[1-(S)-ethoxycarbonyl-2-(3-indolyl)ethyl]-amide acetate | 0.26 (chloroform:methanol:acetic acid = 10:1:1) | (CDCl₃ + CD₃OD + d6-DMSO) 8.18(2H, d), 7.92(2H, d), 7.60(1H, d), 7.55–7.35(5H, m), 7.21(1H, s), 7.19–7.00(3H, m), 4.85(1H, t), 4.18(2H, q), 3.50–3.30(2H, m), 2.05(3H, s), 1.95(3H, s), 1.26(3H, t). |
| 1(d) | 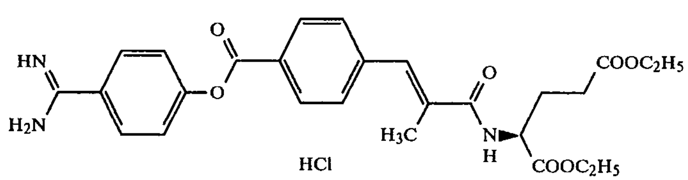 | p-(p-amidino-phenoxycarbonyl)-α-methylcinnamic acid N-[1-(S),3-bis(ethoxycarbonyl)]-propylamide hydrochloride | 0.45 (chloroform:methanol:acetic acid = 15:2:1) | 8.22(2H, d), 7.95(2H, d), 7.60 (2H, d), 7.56(2H, d), 7.38(1H, s), 4.55(1H, dd), 4.21(2H, q), 4.15(2H, q), 2.58–2.42(2H, m), 2.40–1.98(2H, m), 2.17(3H, s), 1.28(3H, t), 1.23(3H, t). |

TABLE 3-continued

| Ex. No. | Structure | Name | TLC (Rf) | NMR |
|---|---|---|---|---|
| 1(e) | (structure with benzylpiperazinyl group, 2CH₃SO₃H) | p-(p-amidino-phenoxycarbonyl)-α-methylcinnamic acid N'-(phenyl-methyl)piperazinyl-amide dimethane sufonate | 0.5 (chloroform:methanol = 8:2) | 8.21(2H, d), 7.92(2H, d), 7.63–7.45(9H, m), 6.77(1H, brs), 4.60–4.32(2H, m), 4.41(2H, s), 3.60–3.10(6H, m), 2.70(6H, s), 2.15(3H, brs). |
| 1(f) | (structure with phenyl-COOC₂H₅ group, CH₃SO₃H) | p-(p-amidino-phenoxycarbonyl)-α-methylcinnamic acid N-(1-(R)-phenyl-1-ethoxycarbonyl)methyl-amide methanesulfonate | 0.4 (chloroform:methanol:acetic acid = 15:2:1) | 8.20(2H, d), 7.92(2H, d), 7.60 (2H, d), 7.53(2H, d), 7.55–7.38 (5H, m), 7.33(1H, brs), 5.60 (1H, s), 4.20(2H, dt), 2.70(3H, s), 2.12(3H, brs), 1.21(3H, t). |
| 1(g) | (structure with 4-fluorophenyl-COOC₂H₅, CH₃SO₃H) | p-(p-amidino-phenoxycarbonyl)-α-methylcinnamic acid N-(p-fluoro-phenyl)-N-ethoxycarbonylmethyl-amide methanesulfoate | 0.26 (chloroform:methanol:acetic acid = 10:1:1) | 8.13(2H, d), 7.91(2H, d), 7.51(2H, d), 7.47–7.40(2H, m), 7.29(2H, d), 7.15(2H, t), 6.70(1H, s), 4.52(2H, s), 4.24(2H, q), 2.72(3H, s), 1.91(3H, s), 1.30(3H, t). |
| 1(h) | (structure with 4-methylphenyl-COOC₂H₅, CH₃SO₃H) | p-(p-amidino-phenoxycarbonyl)-α-methylcinnamic acid N-(p-methyl-phenyl)-N-ethoxycarbonylmethyl-amide methanesulfonate | 0.31 (chloroform:methanol:acetic acid = 10:1:1) | 8.11(2H, d), 7.92(2H, d), 7.51(2H, d), 7.26(2H, d), 7.25(4H, s), 6.70(1H, s), 4.50(2H, s), 4.23(2H, q), 2.72(3H, s), 2.33(3H, s), 1.89(3H, s), 1.30(3H, t). |

| Ex. No. | Structure | Name | TLC (Rf) | NMR |
|---|---|---|---|---|
| 1(i) | [structure with allyl group, CH₃COOH] | p-(p-amidino-phenoxycarbonyl)-α-methylcinnamic acid N-allyl-N-ethoxycarbonyl methylamide acetate | 0.55 (chloroform:methanol:acetic acid = 10:2:1) | 8.22(2H, d), 7.94(2H, d), 7.57–7.49(4H, m), 6.74(1H, br), 5.90(1H, br), 5.33 and 5.27 (2H, br), 4.26–4.14(6H, m), 2.15(3H, s), 1.30(3H, t). |
| 1(j) | [structure with propargyl group, CH₃COOH] | p-(p-amidino-phenoxycarbonyl)-α-methylcinnamic acid N-propargyl-N-ethoxycarbonyl methylamide acetate | 0.55 (chloroform:methanol:acetic acid = 10:2:1) | 8.22(2H, d), 7.94(2H, d), 7.60–7.52(4H, m), 6.89 and 6.70(1H, br), 4.38(4H, s), 4.24(2H, q), 2.89(1H, br), 2.12(3H, s), 1.28(3H, t). |
| 1(k) | [structure with N-phenyl, HCl] | p-(p-amidino-phenoxycarbonyl)-β-methylcinnamic acid N-phenyl-N-ethoxycarbonyl-methylamide hydrochloride | 0.44 (chloroform:methanol:acetic acid = 15:2:1) | 8.10(2H, d), 7.92(2H, d), 7.50 (2H, d), 7.41(5H, s), 7.40(2H, d), 6.10(1H, drs), 4.50(2H, s), 4.22(2H, q), 2.42(3H, s), 1.30(3H, t). |
| 1(l) | [structure with N-benzyl, CH₃SO₃H] | p-(p-amidino-phenoxycarbonyl)-β-methylcinnamic acid N-phenyl-methyl-N-ethoxy-carbonylmethyl-amide methanesulfonate | 0.45 (chloroform:methanol:acetic acid = 15:2:1) | 8.20(0.6H, d), 8.18(1.4H, d), 7.90(2H, d), 7.70(0.6H, d), 7.65 (1.4H, d), 7.52(2H, d), 7.42–7.20 (5H, m), 6.61(0.7H, s), 6.55 (0.3H, s), 4.75(1.4H, s), 4.72 (0.6H, s), 4.24–4.02(4H, m), 2.70 (3H, s), 2.35(2.1H, s), 2.30 (0.9H, s), 1.25(2.1H, t), 1.19 (0.9H, t). |

TABLE 3-continued

| Ex. No. | Structure | Name | TLC (Rf) | NMR |
|---|---|---|---|---|
| 1(m) | [structure: p-amidinophenyl ester with methylcinnamic acid N'-phenylmethylpiperazinyl amide, 2HCl] | p-(p-amidinophenoxycarbonyl)-β-methylcinnamic acid N'-phenylmethylpiperazinylamide dihydrochloride | 0.31 (chloroform:methanol: = 8.2) | 8.20(2H, d), 7.95(2H, d), 7.78 (2H, d), 7.70–7.43(7H, m), 6.60 (1H, d), 4.80–4.60(1H, m), 4.43 (2H, s), 4.40–4.18(1H, m), 3.80–3.40(3H, m), 3.40–3.05 (3H, m), 2.31(3H, s). |
| 1(n) | [structure: p-amidinophenyl benzoate with N-benzyl-N-ethoxycarbonylmethyl amide, HCl] | p-(p-amidinophenoxycarbonyl)-benzoic acid N-phenylmethyl-N-ethoxycarbonylmethylamide hydrochloride | 0.64 (chloroform:methanol:acetic acid = 10:2:1) | (CDCl$_3$ + CD$_3$OD) 8.24(2H, d), 7.90(2H, d), 7.70 (1.4H, d), 7.61(0.6H, d), 7.50–7.25 (5.6H, m), 7.20(1.4H, d), 4.82 (0.3H, s), 4.60(0.7H, s), 4.23 (1.4H, q), 4.18(0.6, q), 4.20 (1.4H, t), 3.82(0.6H, s), 1.30 (2.1H, t), 1.22(0.9H, t). |
| 1(o) | [structure: p-amidinophenyl benzoate with N-phenyl-N-ethoxycarbonylmethyl amide, CH$_3$COOH] | p-(p-amidinophenoxycarbonyl)-benzoic acid N-phenyl-N-ethoxycarbonylmethylamide acetate | 0.49 (chloroform:methanol:acetic acid = 10:2:1) | 8.05(2H, d), 7.90(2H, d), 7.60–7.45(4H, m), 7.35–7.10(5H, m), 4.65(2H, s), 4.25(2H, q), 1.95 (3H, s), 1.35(3H, t). |
| 1(p) | [structure: p-amidino-o-methoxycarbonylphenyl benzoate with N-phenyl-N-ethoxycarbonylmethyl amide, CH$_3$COOH] | p-(p-amidino-o-methoxycarbonylphenoxycarbonyl)-benzoic acid N-phenyl-N-ethoxycarbonylmethylamide acetate | 0.30 (chloroform:methanol:acetic acid = 10:1:1) | 8.46(1H, d), 8.10–8.00(3H, m), 7.55–7.49(3H, m), 7.30–7.20 (5H, m), 4.62(2H, s), 4.26(2H, q), 3.69(3H, s), 1.31(3H, t). |

TABLE 3-continued

| Ex. No. | Structure | Name | TLC (Rf) | NMR |
|---|---|---|---|---|
| 1(q) | [structure: p-amidinophenoxycarbonyl benzoate with N-(1-ethoxycarbonyl-2-(3-indolyl)ethyl)amide, CH₃COOH] | p-(p-amidino-phenoxycarbonyl)-benzoic acid N-[1-ethoxycarbonyl-2-(3-indolyl)]ethyl-amide acetate | 0.33 (chloroform:methanol:acetic acid = 10:2:1) | 8.25(2H, d), 8.00–7.85(4H, m), 7.65–7.50(3H, m), 7.35(1H, d), 7.25–6.95(4H, m), 4.95(1H, m), 4.20(2H, q), 3.45(2H, m), 2.00(3H, s), 1.20(3H, t). |
| 1(r) | [structure: with (S)-pyrrolidine-2-carboxylate ethyl ester, CH₃COOH] | p-(p-amidino-phenoxycarbonyl)-benzoic acid N-(2-(S)-ethoxycarbonyl)pyrrolidinylamide acetate | 0.31 (chloroform:methanol:acetic acid = 10:2:1) | 8.30 and 8.25(2H, d), 7.95(2H, d), 7.75 and 7.60(2H, d), 7.55(2H, d), 4.60 and 4.45(1H, m), 4.25 and 4.00(2H, q), 3.75 and 3.60(2H, m), 2.40 (1H, m), 2.20–1.85(3H, m), 2.00(3H, s), 1.30 and 1.10(3H, t). |
| 1(s) | [structure: with (R)-pyrrolidine-2-carboxylate ethyl ester, CH₃COOH] | p-(p-amidino-phenoxycarbonyl)-benzoic acid N-(2-(R)-ethoxycarbonyl)pyrrolidinylamide acetate | 0.31 (chloroform:methanol:acetic acid = 10:2:1) | 8.30 and 8.25(2H, d), 7.95(2H, d), 7.75 and 7.60(2H, d), 7.55(2H, d), 4.60 and 4.45(1H, m), 4.25 and 4.00(2H, q), 3.75 and 3.60(2H, m), 2.40 (1H, m), 2.20–1.85(3H, m), 2.00 (3H, s), 1.30 and 1.10(3H, t). |
| 1(t) | [structure: with N′-phenylmethyl-piperazinylamide, 2HCl] | p-(p-amidino-phenoxycarbonyl)-benzoic acid N′-phenylmethyl-piperazinylamide dihydrochloride | 0.50 (chloroform:methanol:acetic acid = 10:2:1) | 8.28(2H, d), 7.92(2H, d), 7.60 (2H, d), 7.53(2H, d), 7.33–7.24 (5H, m), 3.80(2H, br), 3.44 (2H, br), 2.59(2H, br), 2.48 (2H, br). |

TABLE 3-continued

| Ex. No. | Structure | Name | TLC (Rf) | NMR |
|---|---|---|---|---|
| 1(u) | [structure: HN=C(NH2)-C6H4-O-C(=O)-C6H4-CH=C(CH3)-C(=O)-NH-C6H3(COOC2H5)2 · HCl] | p-(p-amidinophenoxycarbonyl)-α-methylcinnamic acid N-3,5-bis(ethoxycarbonyl)phenylamide hydrochloride | 0.35 (chloroform:methanol:acetic acid = 10:1:1) | (CDCl3 + CD3OD) 8.59(2H, d, J=1.5Hz), 8.42(1H, d, J=1.5Hz), 8.26(2H, d, J=8.2Hz), 7.93(2H, d, J=8.8Hz), 7.64(2H, d, J=8.2Hz), 7.53(2H, d, J=8.8Hz), 7.47(1H, s), 4.43(4H, q, J=7.0Hz), 2.25(3H, d, J=1.4Hz), 1.44(6H, d, J=7.0Hz). |
| 1(v) | [structure: HN=C(NH2)-C6H4-O-C(=O)-C6H4-CH=C(CH3)-C(=O)-NH-CH(COOC2H5)-CH2-COOC2H5 · HCl] | p-(p-amidinophenoxycarbonyl)-α-methylcinnamic acid N-1-(S),2-bis(ethoxycarbonyl)ethylamide hydrochloride | 0.5 (chloroform:methanol:acetic acid = 15:2:1) | (d6-DMSO + CDCl3) 9.80–9.00(3H, m), 8.20(2H, d, J=8.0Hz), 8.00(2H, d, J=8.0Hz), 7.57(2H, d, J=8.5Hz), 7.45(2H, d, J=8.5Hz), 7.38(1H, brs), 4.82(1H, dd, J=6.0Hz, 13Hz), 4.20, 4.17(2H each, q each, J=8.0Hz, each), 2.98(1H, dd, J=6.0Hz, 15Hz), 2.83(1H, dd, J=6.0Hz, 15Hz), 2.13(3H, s), 1.24, 1.23(3H each, t each, J=8.0Hz each). |
| 1(w) | [structure: HN=C(NH2)-C6H4-O-C(=O)-C6H4-CH=C(CH3)-C(=O)-N(CH2-C6H4-COOC2H5)(CH2-COOC2H5) · CH3COOH] | p-(p-amidinophenoxycarbonyl)-α-methylcinnamic acid N-ethoxycarbonylmethyl-N-(4-ethoxycarbonylphenyl)methylamide acetate | 0.49 (chloroform:methanol:acetic acid = 10:1:1) | 8.18(2H, d, J=8.4Hz), 8.03(2H, d, J=8.0Hz), 7.92(2H, d, J=8.4Hz), 7.51(4H, d, J=8.4Hz), 7.45(2H, d, J=8.0Hz), 6.73(1H, s), 4.82(2H, s), 4.37(2H, q, J=7.2Hz), 4.30–4.10(4H, m), 2.14(3H, s), 1.92(3H, s), 1.38(3H, t, J=7.2Hz), 1.35–1.14(3H, m). |
| 1(x) | [structure: HN=C(NH2)-C6H4-O-C(=O)-C6H4-CH=C(CH3)-C(=O)-NH-CH(COOC2H5)2 · HCl] | p-(p-amidinophenoxycarbonyl)-α-methylcinnamic acid N-bis(ethoxycarbonyl)methylamide hydrochloride | 0.63 (chloroform:methanol:acetic acid = 15:2:1) | (d6-DMSO + CDCl3) 10.0–9.00(3H, m), 8.20(2H, d, J=8.0Hz), 8.00(2H, d, J=8.0Hz), 7.57(2H, d, J=8.5Hz), 7.45(2H, d, J=8.5Hz), 7.43(1H, brs), 5.27(1H, brs), 4.40–4.20(4H, m), 2.18(3H, s), 1.32(6H, brt, J=8.0Hz). |

TABLE 3-continued

| Ex. No. | Structure | Name | TLC (Rf) | NMR |
|---|---|---|---|---|
| 1(y) | 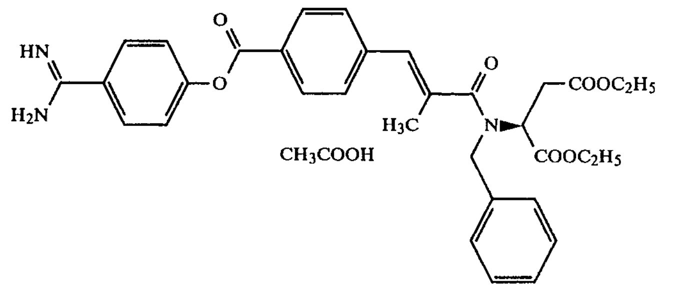 | p-(p-amidino-phenoxycarbonyl)-α-methylcinnamic acid N-1-(S),2-bis(ethoxycarbonyl)ethyl-N-phenyl-methylamide acetate | 0.42 (chloroform:methanol:acetic acid = 10:2:1) | 8.20(2H, d, J=8Hz), 7.90(2H, d, J=8Hz), 7.50(4H, d, J=8Hz), 7.50-7.20(5H, m), 6.80(1H, br), 4.90-4.30(2H, br), 4.20-4.00(4H, br), 3.30(2H, s), 2.80-2.60(1H, m), 2.10(3H, br), 1.95(3H, s), 1.40-1.15(6H, m). |
| 1(z) | 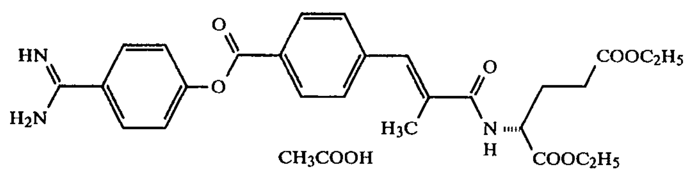 | p-(p-amidino-phenoxycarbonyl)-α-methylcinnamic acid N-1-(R),3-bis(ethoxycarbonyl)propylamide acetate | 0.36 (chloroform:methanol:acetic acid = 10:2:1) | 8.20(2H, d, J=8Hz), 7.90(2H, d, J=8Hz), 7.60(2H, d, J=8Hz), 7.55(2H, d, J=8Hz), 7.35(1H, s), 4.55(1H, dt, J=5, 5Hz), 4.20(2H, q, J=8Hz), 4.15(2H, q, J=8Hz), 2.50(2H, t, J=7Hz), 2.40-2.00(2H, m), 2.15(3H, s), 1.95(3H, s), 1.30(3H, t, J=8Hz), 1.25(3H, t, J=8Hz). |
| 1(aa) | 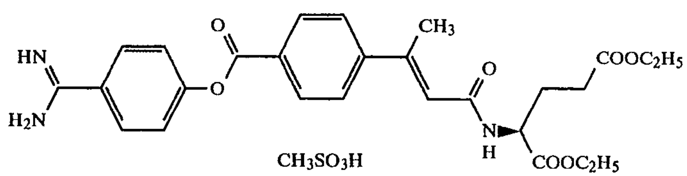 | p-(p-amidino-phenoxycarbonyl)-β-methylcinnamic acid N-1-(S),3-bis(ethoxycarbonyl)propylamide methanesulfonate | 0.46 (chloroform:methanol:acetic acid = 15:2:1) | 8.20(2H, d, J=8.0Hz), 7.93(2H, d, J=8.0Hz), 7.73(2H, d, J=8.0Hz), 7.55(2H, d, J=8.0Hz), 6.20(1H, s), 4.52(1H, dd, J=5.0, 8.0Hz), 4.20(2H, q, J=8.0Hz), 4.15(2H, q, J=8.0Hz), 2.70(3H, s, MeSO3H), 2.55(3H, s), 2.45(2H, brt, J=8.0Hz), 2.30-1.88(2H, m), 1.28(3H, t, J=8.0Hz), 1.22(3H, t, J=8.0Hz). |
| 1(bb) | 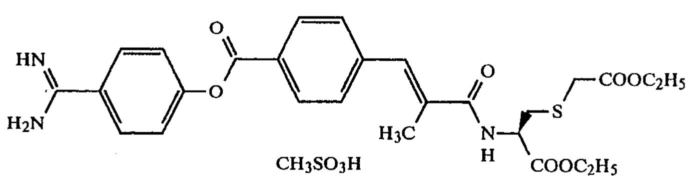 | p-(p-amidino-phenoxycarbonyl)-α-methylcinnamic acid N-((1-S)-ethoxycarbonyl-2-ethoxycarbonyl-methylthio)ethyl)-amide methanesulfonate | 0.47 (chloroform:methanol:acetic acid = 10:1:1) | 8.24(2H, d, J=8.4Hz), 7.94(2H, d, J=8.8Hz), 7.61(2H, d, J=8.4Hz), 7.54(2H, d, J=8.8Hz), 7.39(1H, s), 4.80-4.70(1H, m), 4.24(2H, q, J=7.0Hz), 4.20(2H, q, J=7.2Hz), 3.50-3.30(5H, m), 2.72(3H, s), 2.15(3H, s), 1.31(3H, t, J=7.0Hz), 1.29(3H, t, J=7.2Hz). |

TABLE 3-continued

| Ex. No. | Structure | Name | TLC (Rf) | NMR |
|---|---|---|---|---|
| 1(cc) | [structure with HCl, COOC₂H₅ groups] | p-(p-amidino-phenoxycarbonyl)-α-methylcinnamic acid N-(1,4-bis(ethoxycarbonyl)butyl)amide hydrochloride | 0.47 (chloroform:methanol:acetic acid = 15:2:1) | 8.22(2H, d, J=8.0Hz), 7.92(2H, d, J=8.0Hz), 7.60(2H, d, J=8.0Hz), 7.55(2H, d, J=8.0Hz), 7.34(1H, s), 4.49(1H, dd, J=8.5Hz, 5.0Hz), 4.20(2H, q, J=7.5Hz), 4.12(2H, q, J=7.5Hz), 2.40(2H, t, J=8.0Hz), 2.12(3H, s), 2.10–1.60(4H, m), 1.27(3H, t, J=7.5Hz), 1.23(3H, t, J=7.5Hz). |
| 1(dd) | [structure with HCl, COOC₂H₅ groups] | p-(p-amidino-phenoxycarbonyl)-α-methylcinnamic acid N-(1,5-bis(ethoxycarbonyl)pentyl)amide hydrochloride | 0.49 (chloroform:methanol:acetic acid = 15:2:1) | 8.21(2H, d, J=8.0Hz), 7.92(2H, d, J=8.0Hz), 7.60(2H, d, J=8.0Hz), 7.55(2H, d, J=8.0Hz), 7.34(1H, s), 4.45(1H, dd, J=8.5Hz, 5.0Hz), 4.20(2H, q, J=7.5Hz), 4.10(2H, q, J=7.5Hz), 2.36(2H, t, J=7.5Hz), 2.00–1.80(2H, m), 1.80–1.58(2H, m), 1.58–1.38(2H, m), 1.30(3H, t, J=7.5Hz), 1.22(3H, t, J=7.5Hz). |
| 1(ee) | [structure with CH₃COOH, COOC₂H₅] | p-(p-amidino-phenoxycarbonyl)-α-methylcinnamic acid N-(3-ethoxycarbonylpropyl)amide acetate | 0.31 (chloroform:methanol:acetic acid = 15:2:1) | 8.21(2H, d, J=8.0Hz), 7.95(2H, d, J=8.0Hz), 7.59(2H, d, J=8.0Hz), 7.53(2H, d, J=8.0Hz), 7.31(1H, brs), 4.12(2H, q, J=7.5Hz), 3.35(2H, t, J=8.0Hz), 2.40(2H, t, J=8.0Hz), 2.1(3H, d, J=1.0Hz), 2.00(3H, s), 1.90(2H, tt, J=8.0Hz), 1.22(3H, t, J=7.5Hz). |
| 1(ff) | [structure with CH₃SO₃H, COOC₂H₅] | p-(p-amidino-phenoxycarbonyl)-α-methylcinnamic acid N-ethoxycarbonylmethylamide methane-sulfonate | 0.35 (chloroform:methanol:acetic acid = 15:2:1) | 8.23(2H, d, J=8.5Hz), 7.93(2H, d, J=8.5Hz), 7.60(2H, d, J=8.5Hz), 7.54(2H, d, J=8.5Hz), 7.41(1H, s), 4.21(2H, q, J=7.0Hz), 4.03(2H, s), 2.69(3H, s, MeSO₃H), 2.15(3H, d, J=1.5Hz), 1.30(3H, t, J=7.0Hz). |

TABLE 3-continued

| Ex. No. | Structure | Name | TLC (Rf) | NMR |
|---|---|---|---|---|
| 1(gg) | (structure with HCl salt; p-amidinophenyl ester of cinnamate with bis(ethoxycarbonylmethyl)amide) | p-(p-amidinophenoxycarbonyl)-α-methylcinnamic acid N-(1,1-bis(ethoxycarbonyl-methyl)methyl)amide hydrochloride | 0.41 (chloroform:methanol:acetic acid = 15:2:1) | 8.21(2H, d, J=8.0Hz), 7.95(2H, d, J=8.0Hz), 7.58(2H, d, J=7.5Hz), 7.53(2H, d, J=7.5Hz), 7.22(1H, s), 4.50(1H, dt, J=7.0 Hz), 4.16(4H, q, J=7.5Hz), 2.69(4H, d, J=7.0Hz), 2.09(3H, s), 1.23(6H, t, J=7.5Hz). |
| 1(hh) | (structure; HCl salt) | p-(p-amidinophenoxycarbonyl)-α-methylcinnamic acid N-(1-ethoxycarbonyl-2-(4-ethoxycarbonylphenyl)ethyl)amide hydrochloride | 0.43 (chloroform:methanol:acetic acid = 15:2:1) | 8.20(2H, d, J=8.0Hz), 7.98(2H, d, J=8.0Hz), 7.93(2H, d, J=8.0Hz), 7.60–7.48(4H, m), 7.40(2H, d, J=7.5Hz), 7.18(1H, s), 4.90–4.70(1H, m), 4.35(2H, q, J=8.0Hz), 4.20(2H, q, J=8.0Hz), 3.50–3.30(1H, m), 3.18(1H, dd, J=10.0, 13.0Hz), 2.02(3H, s), 1.39(3H, t, J=8.0Hz), 1.25(3H, t, J=8.0Hz). |
| 1(ii) | (structure; CH3SO3H salt) | p-(p-amidinophenoxycarbonyl)-α-methylcinnamic acid N-(1-ethoxycarbonyl-2-(3-ethoxycarbonylphenyl)ethyl)amide methanesulfonate | 0.44 (chloroform:methanol:acetic acid = 15:2:1) | 9.38(1H, brs), 8.83(1H, brs), 8.22(1H, d, J=7.5Hz), 8.85–8.00(4H, m), 7.61–7.35(6H, m), 7.20(1H, brs), 4.79(1H, dd, J=5.0, 8.0Hz), 4.37(2H, q, J=8.0Hz), 4.21(2H, q, J=8.0Hz), 3.41–3.25(1H, m), 3.19(1H, dd, J=8.0, 13.0Hz), 2.72(3H, s, MeSO3H), 2.07(3H, s), 1.37(3H, t, J=8.0Hz), 1.28(3H, t, J=8.0Hz). |
| 1(jj) | (structure; HCl salt) | p-(p-amidinophenoxycarbonyl)-α-methylcinnamic acid N-(1,1-bis(ethoxycarbonyl)methyl)-N-allylamide hydrochloride | 0.43 (chloroform:methanol:acetic acid = 15:2:1) | (CDCl3 + d6-DMSO) 9.40(3H, brs), 8.18(2H, d, J=8.0Hz), 8.00(2H, d, J=8.0Hz), 7.45(2H, d, J=8.0Hz), 7.40(2H, d, J=8.0Hz), 6.70(1H, s), 5.84(1H, tt, J=5.0, 15.0Hz), 5.48–5.15(2H, m), 4.98(1H, brs), 4.23(4H, q, J=7.0Hz), 4.17(2H, d, J=5.0Hz), 2.17(3H, s), 1.31(3H, t, J=7.0Hz). |

TABLE 3-continued

| Ex. No. | Structure | Name | TLC (Rf) | NMR |
|---|---|---|---|---|
| 1(kk) | 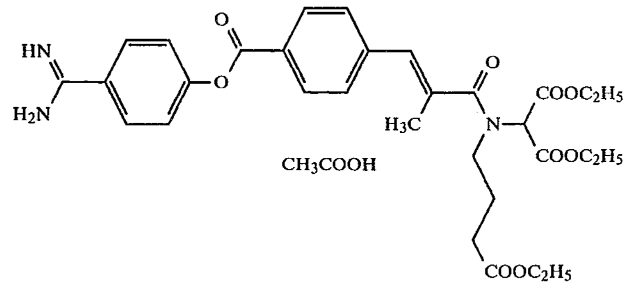 | p-(p-amidino-phenoxycarbonyl)-α-methylcinnamic acid N-3-ethoxycarbonylpropyl-N-(1,1-bis(ethoxycarbonyl)methyl)amide acetate | 0.51 (chloroform:methanol:acetic acid = 10:1:1) | 8.23(2H, d, J=8.4Hz), 7.93(2H, d, J=8.8Hz), 7.60(2H, d, J=8.8Hz), 7.52(2H, d, J=8.4Hz), 6.70(1H, s), 4.29(4H, q, J=7.4Hz), 4.20-4.00(3H, m), 3.60(2H, m), 2.39(2H, t, J=7.0Hz), 2.16(3H, s), 2.05-1.80(2H, m), 1.94(3H, s), 1.40-1.15(9H, m). |
| 1(ll) | 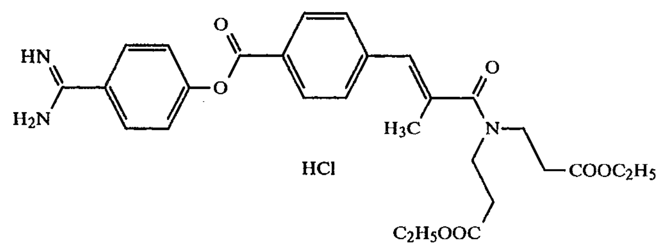 | p-(p-amidino-phenoxycarbonyl)-α-methylcinnamic acid N,N-bis(2-ethoxycarbonyl ethyl)amide hydrochloride | 0.59 (chloroform:methanol:acetic acid = 10:2:1) | 8.20(2H, d, J=8.0Hz), 7.90(2H, d, J=8.0Hz), 7.58(2H, d, J=8.0Hz), 7.55(2H, d, J=8.0Hz), 6.60(1H, s), 4.15(4H, q, J=7.5Hz), 3.81-3.60(4H, m), 2.68(4H, t, J=7.5Hz), 2.14(3H, s), 1.22(6H, t, J=7.5Hz). |
| 1(mm) | 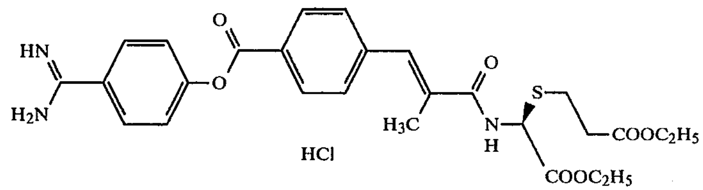 | p-(p-amidino-phenoxycarbonyl)-α-methylcinnamic acid N-(1-(S)-ethoxycarbonyl-1-(2-ethoxycarbonylethylthio)-methyl)amide hydrochloride | 0.48 (chloroform:methanol:acetic acid = 10:2:1) | 8.25(2H, d, J=8Hz), 7.90(2H, d, J=8Hz), 7.60(2H, d, J=8Hz), 7.55(2H, d, J=8Hz), 7.40(1H, br), 4.70(1H, dd, J=7, 5Hz), 4.25(2H, q, J=6.5Hz), 4.15(2H, q, J=8Hz), 3.15(1H, dd, J=15, 7Hz), 3.00(1H, dd, J=15, 7Hz), 2.85(2H, t, J=7Hz), 2.65(2H, t, J=7Hz), 2.20(3H, s), 1.30(3H, t, J=6.5Hz), 1.25(3H, t, J=8Hz). |
| 1(nn) | 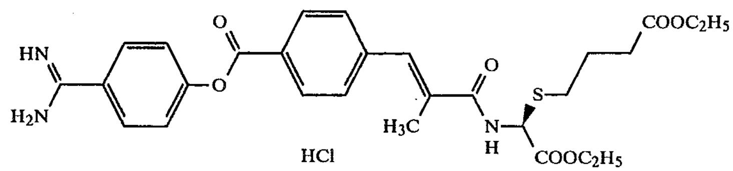 | p-(p-amidino-phenoxycarbonyl)-α-methylcinnamic acid N-(1-(S)-ethoxycarbonyl-1-(3-ethoxycarbonylpropylthio)methyl)amide hydrochloride | 0.48 (chloroform:methanol:acetic acid = 10:2:1) | 8.25(2H, d, J=8Hz), 7.90(2H, d, J=8Hz), 7.60(2H, d, J=8Hz), 7.55(2H, d, J=8Hz), 7.35(1H, br), 4.70(1H, dd, J=7, 5Hz), 4.25(2H, q, J=6.5Hz), 4.15(2H, q, J=8Hz), 3.15(1H, dd, J=15, 5Hz), 3.00(1H, dd, J=15, 7Hz), 2.65(2H, t, J=7.5Hz), 2.45(2H, t, J=7Hz), 2.20(3H, s), 1.90(2H, m), 1.30(3H, t, J=6.5Hz), 1.25(3H, t, J=8Hz). |

TABLE 3-continued

| Ex. No. | Structure | Name | TLC (Rf) | NMR |
|---|---|---|---|---|
| 1(oo) | [structure with COOCH3, COOC2H5, N-allyl, CH3COOH] | p-(p-amidino-o-methoxycarbonyl-phenoxycarbonyl)-α-methylcinnamic acid N-ethoxycarbonylmethyl-N-allylamide acetate | 0.47 (chloroform:methanol:acetic acid = 10:2:1) | 8.49(1H, d, J=2.0Hz), 8.21(2H, d, J=9.0Hz), 8.10(1H, dd, J=9.0Hz, 2.0Hz), 7.58(3H, d, J=9.0Hz), 6.69 and 6.75(1H, m), 5.83–6.00(1H, m), 5.24–5.33(2H, m), 4.20(2H, q, J=7.0Hz), 4.10(4H, br), 3.78(3H, s), 2.14(3H, s), 1.29(3H, t, J=7.0Hz). |
| 1(pp) | [structure with COOC2H5, COOC2H5, HCl] | p-(p-amidino-o-ethoxycarbonyl-phenoxycarbonyl)-α-methylcinnamic acid N-(1-(S),3-bis(ethoxycarbonyl)propyl)amide hydrochloride | 0.53 (chloroform:methanol:acetic acid = 10:2:1) | (CDCl3 + CD3OD) 8.51(1H, d, J=2.5Hz), 8.22(2H, d, J=8.0Hz), 8.08(1H, dd, J=2.5, 9.0Hz), 7.57(2H, d, J=8.0Hz), 7.53(1H, d, J=9.0Hz), 7.41(1H, s), 4.61(1H, dd, J=3.0, 8.0Hz), 4.24, 4.22, 4.18(2H each, q each, J=7.5Hz each), 2.51(2H, t, J=7.5Hz), 2.40–2.00(2H, m), 2.17(3H, s), 1.32, 1.27, 1.14(3H each, t each, J=7.5Hz each). |
| 1(qq) | [structure with COOC2H5, COOC2H5, N-allyl, HCl] | p-(p-amidino-o-ethoxycarbonyl-phenoxycarbonyl)-α-methylcinnamic acid N-ethoxycarbonylmethyl-N-allylamide hydrochloride | 0.57 (chloroform:methanol:acetic acid = 10:2:1) | (CDCl3 + CD3OD) 8.48(1H, d, J=2.5Hz), 8.21(2H, d, J=8.0Hz), 8.08(1H, dd, J=2.5, 9.0Hz), 7.51(1H, d, J=9.0 Hz), 7.47(2H, d, J=8.0Hz), 6.73(1H, brs), 6.00–5.75(1H, m), 5.40–5.20(2H, m), 4.38–4.20(4H, m), 4.20–4.05(4H, m), 2.18(3H, brs), 1.31(3H, t, J=7.5Hz), 1.13(3H, t, J=7.5Hz). |
| 1(rr) | [structure with COOC2H5, COOC2H5, COOC2H5, CH3COOH] | p-(p-amidino-phenoxycarbonyl)-α-methylcinnamic acid N-(1,1-bis(ethoxycarbonyl)methyl)-N-ethoxycarbonylmethylamide acetate | 0.47 (chloroform:methanol:acetic acid = 10:2:1) | 8.25(2H, d, J=8Hz), 7.90(2H, d, J=7Hz), 7.65–7.50(4H, m), 6.75(1H, br.s), 4.45–4.10(9H, m), 2.20(3H, br.s), 1.40–1.20(9H, m). |

TABLE 3-continued

| Ex. No. | Structure | Name | TLC (Rf) | NMR |
|---|---|---|---|---|
| 1(ss) | *[structure: p-amidinophenyl 4-{(E)-2-methyl-2-[N-(1-(S)-bis(ethoxycarbonyl)methyl)-N-ethoxycarbonylmethylcarbamoyl]vinyl}benzoate · CH₃COOH]* | p-(p-amidino-phenoxycarbonyl)-α-methylcinnamic acid N-(1-(S),2-bis(ethoxycarbonyl)ethyl)-N-ethoxy-carbonylmethyl-amide acetate | 0.41 (chloroform:methanol:acetic acid = 10:2:1) | 8.21(2H, d, J=9.0Hz), 7.92 (2H, d, J=9.0Hz), 7.52(4H, d, J=9.0Hz), 6.78 and 6.68(1H, m), 5.39 and 4.80(1H, m), 4.55–3.93(2H, m), 4.20(6H, q, J=7.0Hz), 3.33–2.90(2H, m), 2.18 and 2.09(3H, m), 1.28(9H, t, J=7.0Hz). |
| 1(tt) | *[structure]* | p-(p-amidino-phenoxycarbonyl)-α-methylcinnamic acid N-(1,1-bis(ethoxycarbonyl)methyl)-N-(2-ethoxycarbonyl)ethyl)amide acetate | 0.56 (chloroform:methanol:acetic acid = 10:2:1) | 8.25(2H, d, J=8Hz), 7.95(2H, d, J=9Hz), 7.60(2H, d, J=8 Hz), 7.55(2H, d, J=9Hz), 6.70(1H, m), 4.25(4H, q, J=7Hz), 4.15(2H, q, J=7Hz), 4.15(1H, br.), 3.85(2H, br.), 2.75(2H, t, J=6.5Hz), 2.20(3H, s), 1.95(3H, s, CH₃COOH), 1.40–1.20 (9H, m). |
| 1(uu) | *[structure]* | p-(p-amidino-phenoxycarbonyl)-α-methylcinnamic acid N-allyl-N-(1-(S)-ethoxycarbonyl)ethyl)amide acetate | 0.43 (chloroform:methanol:acetic acid = 10:2:1) | 8.20(2H, d, J=8Hz), 7.95(2H, d, J=9Hz), 7.60–7.50(4H, m), 6.65(1H, s), 5.95(1H, m), 5.50–5.20(2H, m), 4.30–4.10(5H, m), 2.10(3H, s), 1.95(3H, s, CH₃COOH), 1.50(3H, d, J=7 Hz), 1.30(3H, t, J=7Hz). |
| 1(vv) | *[structure]* | p-(p-amidino-phenoxycarbonyl)-α-methylcinnamic acid N-allyl-N-(1-(R),2-bis(ethoxycarbonyl)ethyl)amide acetate | 0.44 (chloroform:methanol:acetic acid = 10:2:1) | 8.20(2H, d, J=8Hz), 7.95(2H, d, J=9Hz), 7.60–7.55(4H, m), 6.70(1H, br.s), 6.00(1H, m), 5.50–5.20(2H, m), 4.50(1H, m), 4.30–4.10(6H, m), 3.25 and 2.90 (2H, m), 2.15(3H, br.s), 2.00(3H, s, CH₃COOH), 1.25(6H, t, J=6.5Hz). |

TABLE 3-continued

| Ex. No. | Structure | Name | TLC (Rf) | NMR |
|---|---|---|---|---|
| 1(ww) | (structure with p-amidinophenoxycarbonyl cinnamic acid ester with bis(ethoxycarbonyl) group and COOC₂H₅ substituents; HCl salt) | p-(p-amidino-phenoxycarbonyl)-α-methylcinnamic acid N-(1-(R),2-bis(ethoxycarbonyl)ethyl)-N-ethoxycarbonyl-methylamide hydrochloride | 0.49 (chloroform:methanol:acetic acid = 10:2:1) | 8.20(2H, d, J=8Hz), 7.95(2H, d, J=9Hz), 7.65–7.50(4H, m), 6.75(1H, m), 5.40 and 4.40(1H, m), 4.30–4.00(8H, m), 3.30–2.90 (2H, m), 2.15(3H, m), 1.35–1.15 (9H, m). |
| 1(xx) | (structure with N-benzyl group, COOC₂H₅; CH₃COOH) | p-(p-amidino-phenoxycarbonyl)-α-methylcinnamic acid N-benzyl-N-(2-ethoxycarbonyl-ethyl)amide acetate | 0.38 (chloroform:methanol:acetic acid = 10:2:1) | 8.19(2H, d, J=9.0Hz), 7.92(2H, d, J=9.0Hz), 7.52(2H, d, J=9.0Hz), 7.35(2H, d, J=9.0Hz), 7.50–7.28(5H, m), 6.67(1H, s), 4.73(2H, s), 4.11(2H, q, J=7.0 Hz), 3.69(2H, t, J=7.0Hz), 2.63 (2H, t, J=7.0Hz), 2.10(3H, br-s), 1.22(3H, t, J=7.0Hz). |
| 1(yy) | (structure with bis(ethoxycarbonyl)ethyl and 2-ethoxycarbonylethyl groups; CH₃COOH) | p-(p-amidino-phenoxycarbonyl)-α-methylcinnamic acid N-(1-(R),2-bis(ethoxycarbonyl)ethyl)-N-(2-ethoxycarbonylethyl)amide acetate | 0.39 (chloroform:methanol:acetic acid = 10:2:1) | 8.21(2H, d, J=9.0Hz), 7.92(2H, d, J=9.0Hz), 7.58(2H, d, J=9.0Hz), 7.52(2H, d, J=9.0Hz), 6.65(1H, br-s), 4.52(1H, br), 4.20 and 4.13(6H, q, J=7.0Hz), 3.97–3.83(2H, m), 3.22(1H, br), 2.94(1H, dd, J=16.0Hz, 7.0Hz), 2.76(2H, br), 2.12(3H, s), 1.28 and 1.22(9H, t, J=7.0Hz). |
| 1(zz) | (structure with COOC₂H₅, CH₃, COOC₂H₅ groups; CH₃COOH) | p-(p-amidino-phenoxycarbonyl)-α-methylcinnamic acid N-(1-(S)-ethoxycarbonylethyl)-N-ethoxycarbonylmethyl-amide acetate | 0.54 (chloroform:methanol:acetic acid = 10:2:1) | 8.21(2H, d, J=9.0Hz), 7.92(2H, d, J=9.0Hz), 7.57(2H, d, J=9.0Hz), 7.51(2H, d, J=9.0Hz), 6.69(1H, s), 4.85–4.69(1H, m), 4.34(1.2H, s), 4.20(4H, q, J=7.0Hz), 3.92(0.8H, d, J=18.0Hz), 2.15 and 2.10(3H, eachS), 1.50 (3H, d, J=7.0Hz), 1.26(6H, t, J=7.0Hz). |

TABLE 3-continued

| Ex. No. | Structure | TLC (Rf) | Name | NMR |
|---|---|---|---|---|
| 1(aaa) | (structure) | 0.55 (chloroform:methanol:acetic acid = 10:2:1) | p-(p-amidinophenoxycarbonyl)-α-methylcinnamic acid N-(1-(S)-ethoxycarbonylethyl)-N-(2-ethoxycarbonylethyl)amide acetate | 8.20(2H, d, J=9.0Hz), 7.92(2H, d, J=9.0Hz), 7.56(2H, d, J=9.0Hz), 7.50(2H, d, J=9.0Hz), 6.62(1H, s), 4.23-4.15(1H, m), 4.12(4H, q, J=7.0Hz), 3.82(2H, br), 2.74(2H, t-like), 2.12(3H, s), 1.51(3H, d, J=7.0Hz), 1.26(6H, t, J=7.0Hz). |
| 1(bbb) | (structure) | 0.44 (chloroform:methanol = 8:2) | p-(p-amidinophenoxycarbonyl)-α-methylcinnamic acid N-(1-(S)-2-bis(ethoxycarbonyl)ethyl)-N-(3-ethoxycarbonylpropyl)amide acetate | 8.22(2H, d, J=8Hz), 7.93(2H, d, J=8Hz), 7.59(2H, d, J=8Hz), 7.54(2H, d, J=8Hz), 6.64(1H, bs), 4.30-3.95(6H, m), 3.80-3.10(4H, m), 3.01-2.85(1H, m), 2.46-2.31(2H, m), 2.13(3H, s), 1.91(3H, s), 1.34-1.09(9H, m). |
| 1(ccc) | (structure) | 0.48 (chloroform:methanol:acetic acid = 10:2:1) | p-(p-amidinophenoxycarbonyl)-α-methylcinnamic acid N-allyl-N-((1-(R)-ethoxycarbonyl-2-ethoxycarbonylmethylthio)ethyl)-amide hydrochloride | 8.25(2H, d, J=8Hz), 7.95(2H, d, J=9Hz), 7.65-7.50(4H, m), 6.80(1H, br.s), 6.00(1H, br.), 5.45-5.15(2H, m), 4.40-4.00(7H, m), 3.50-3.10(4H, m), 2.15(3H, br.s), 1.40-1.20(6H, m). |
| 1(ddd) | (structure) | 0.39 (chloroform:methanol:acetic acid = 10:2:1) | p-(p-amidinophenoxycarbonyl)-α-methylcinnamic acid N-((1-(R)-ethoxycarbonyl-2-ethoxycarbonylmethylthio)ethyl)-N-(3-ethoxycarbonylpropyl)-amide hydrochloride | 8.25(2H, d, J=8Hz), 7.95(2H, d, J=9Hz), 7.65-7.50(4H, m), 6.70(1H, br.), 4.50-4.00(7H, m), 3.80-3.20(6H, m), 2.40(2H, m), 2.20(3H, br.s), 2.05(2H, m), 1.40-1.10(9H, m). |

TABLE 3-continued

| Ex. No. | Structure | Name | TLC (Rf) | NMR |
|---|---|---|---|---|
| 1(eee) | (structure with p-amidinophenoxy group, cinnamic acid, diethyl ester substituents, methyl ester chain, CH₃COOH) | p-(p-amidino-phenoxycarbonyl)-α-methylcinnamic acid N-(1,1-bis(ethoxycarbonyl)methyl-N-(3-methoxycarbonyl-propyl)amide acetate | 0.30 (chloroform:methanol:acetic acid = 10:2:1) | 8.23(2H, d, J=8Hz), 7.91(2H, d, J=8Hz), 7.60(2H, d, J=8 Hz), 7.53(2H, d, J=8Hz), 6.69 (1H, s), 4.90(1H), 4.27(4H, q, J=7Hz), 4.0–4.1 (1H, m), 3.5–3.7(5H, m), 2.42 (2H, t, J=7Hz), 2.17(3H, s), 1.8–2.0(2H, m), 1.91(3H, s), 1.32(6H, t, J=7Hz). |
| 1(fff) | (structure with p-amidinophenoxy group, cinnamic acid, diethyl ester substituents, propyl chain with COOC₂H₅, CH₃COOH) | p-(p-amidino-phenoxycarbonyl)-α-methylcinnamic acid N-(1(S),3-bis(ethoxycarbonyl)-propyl)-N-(3-ethoxycarbonyl-propyl)amide acetate | 0.30 (chloroform:methanol = 9:1) | 8.22(2H, d, J=8Hz), 7.93(2H, d, J=8Hz), 7.59(2H, d, J=8 Hz), 7.53(2H, d, J=8Hz), 6.66(1H, bs), 4.30–3.90(6H, m), 3.80–3.15(3H, m), 2.60–2.30(4 H, m), 2.30–1.80(4H, m), 2.13(3 H, s), 1.91(3H, s), 1.35–1.05 (9H, s). |
| 1(ggg) | (structure with p-amidinophenoxy group, cinnamic acid, diethyl ester substituents, isopentyl chain, CH₃COOH) | p-(p-amidino-phenoxycarbonyl)-α-methylcinnamic acid N-(1,1-bis(ethoxycarbonyl)methyl)-N-isopentylamide acetate | 0.41 (chloroform:methanol = 8:2) | 8.24(2H, d, J=8Hz), 7.93(2H, d, J=8Hz), 7.59(2H, d, J=8 Hz), 7.54(2H, d, J=8Hz), 6.71(1H, bs), 4.27(4H, q, J=7 Hz), 3.63–3.35(2H, m), 2.16(3H, s), 1.91(3H, s), 1.67–1.45(3H, m), 1.30(6H, t, J=7Hz), 0.89(6 H, d, J=6Hz). |

TABLE 3-continued

| Ex. No. | Structure | Name | TLC (Rf) | NMR |
|---|---|---|---|---|
| 1(hhh) | (structure) CH₃COOH | p-(p-amidino-phenoxycarbonyl)-α-methylcinnamic acid N-(1,1-bis(ethoxycarbonyl)methyl)-N-5-ethoxycarbonyl-pentyl)amide acetate | 0.41 (chloroform:methanol:acetic acid = 10:2:1) | 8.24(2H, m), 7.92 and 6.94(2H, d, J=10Hz), 7.72–7.35(4H, m), 6.71 and 6.59(1H, br), 4.38–3.99 (6H, m), 3.60–3.37(2H, br), 2.30 (2H, t, J=7Hz), 2.16 and 2.02 (3H, s), 1.92(3H, s), 1.80–1.50 (4H, br), 1.48–1.17(11H, m). |
| 1(iii) | (structure) CH₃COOH | p-(p-amidino-phenoxycarbonyl)-α-methylcinnamic acid N-(1-(R)-ethoxycarbonyl-2-phenylethyl)-N-(3-ethoxycarbonyl-propyl)amide acetate | 0.27 (chloroform:methanol:acetic acid = 10:2:1) | 8.19(2H, d, J=8Hz), 7.92(2H, d, J=8Hz), 7.52(4H, d, J=8 Hz), 7.2–7.3(5H, br), 6.41 and 6.07(1H, s), 4.1–4.4(3H, m), 3.9–4.1(2H, m), 3.3–3.5(2H, m), 2.2–2.9(2H, br), 2.0–2.2(5H, m), 1.93(3H, s), 1.5–1.8(2H, m), 1.30(3H, t, J=7Hz), 1.17(3H, t, J=7Hz). |
| 1(jjj) | (structure) HCl | p-(p-amidino-phenoxycarbonyl)-α-methylcinnamic acid N-(1-(S)-ethoxycarbonyl-3-methylbutyl)-N-(3-ethoxycarbonyl-propyl)amide hydrochloride | 0.70 (chloroform:methanol:acetic acid = 10:2:1) | 8.20(2H, d, J=8Hz), 7.95(2H, d, J=9Hz), 7.65–7.50(4H, m), 6.65 (1H, br.), 4.50–4.00(5H, m), 3.80–3.30(2H, m), 2.40(2H, t, J=7Hz), 2.15(3H, s), 2.10–1.60(5H, m), 1.35–1.10(6H, m), 1.00(6H, m). |
| 1(kkk) | (structure) CH₃COOH | p-(p-amidino-phenoxycarbonyl)-α-methylcinnamic acid N-(1,1-bis(ethoxycarbonyl)methyl)-N-(3-methylbutyl)amide acetate | 0.36 (chloroform:methanol:acetic acid = 10:2:1) | 8.21(2H, d, J=8Hz), 7.93(2H, d, J=8Hz), 7.57(2H, d, J=8Hz), 7.53 (2H, d, J=8Hz), 6.63(1H, bs), 4.25–4.00(5H, m), 3.50–3.20(2H, m), 3.10–2.60(4H, m), 2.13(3H, s), 1.91(3H, s), 1.70–1.42(3H, m), 1.36–1.07(6H, m), 1.07–0.80(6H, m). |

TABLE 3-continued

| Ex. No. | Structure | Name | TLC (Rf) | NMR |
|---|---|---|---|---|
| 1(lll) | (structure) | p-(p-amidino-phenoxycarbonyl)-α-methylcinnamic acid N-(1,1-bis(ethoxycarbonyl-methyl)methyl)-N-propylamide acetate | 0.32 (chloroform:methanol:acetic acid = 20:2:1) | 8.23(2H, d, J=8Hz), 7.93(2H, d, J=8Hz), 7.58(2H, d, J=8Hz), 7.54(2H, d, J=8Hz), 6.64 (1H, bs), 4.24-4.04(4H, m), 3.45-3.20(2H, m), 3.10-2.60 (4H, m), 2.13(3H, s), 1.91(3H, s), 1.75-1.53(2H, m), 1.40-1.15 (6H, m), 1.05-0.83(3H, m). |
| 1(mmm) | (structure) | p-(p-amidino-phenoxycarbonyl)-α-methylcinnamic acid N-(1,1-bis(ethoxycarbonyl-methyl)methyl)-N-cyclohexylamide acetate | 0.36 (chloroform:methanol:acetic acid = 20:2:1) | 8.22(2H, d, J=8Hz), 7.92(2H, d, J=8Hz), 7.56(2H, d, J=8Hz), 7.53(2H, d, J=8Hz), 6.60(1H, brs), 4.23-4.00(5H, m), 3.80-3.55(1H, m), 3.20-2.65(4H, m), 2.12(3H, s), 1.92(3H, s), 1.95-1.50(7H, m), 1.50-1.10(9H, m). |
| 1(nnn) | (structure) | p-(p-amidino-phenoxycarbonyl)-α-methylcinnamic acid N-ethoxycarbonylmethyl-N-hexylamide acetate | 0.35 (chloroform:methanol:acetic acid = 10:2:1) | 8.22(2H, d, J=8Hz), 7.92(2H, d, J=8Hz), 7.56(4H, t, J=8Hz), 6.70 and 6.61(1H, s), 4.22(2H, q, J=7Hz), 4.15(2H, s), 3.49 (2H, t, J=7Hz), 2.14 and 2.09(3H, s), 1.93(3H, s), 1.80-1.50(2H, m), 1.50-1.20(9H, m), 0.8-1.0(3H, br). |
| 1(ooo) | (structure) | p-(p-amidino-phenoxycarbonyl)-α-methylcinnamic acid N-ethoxycarbonylmethyl-N-1-propylbutylamide acetate | 0.35 (chloroform:methanol:acetic acid = 10:2:1) | 8.23(2H, d, J=8Hz), 7.91(2H, d, J=8Hz), 7.56(4H, t, J=8Hz), 6.62 and 6.67(1H, s), 4.30-4.10(3H, m), 3.98(2H, s), 2.14 and 2.08 (3H, s), 1.90(3H, s), 1.60-1.10 (11H, m), 0.92(6H, t, J=7Hz). |

TABLE 3-continued

| Ex. No. | Structure | Name | TLC (Rf) | NMR |
|---|---|---|---|---|
| 1(ppp) | (structure with N-methyl amide, CH₃COOH) | p-(p-amidino-phenoxycarbonyl)-α-methylcinnamic acid N-ethoxy-carbonylmethyl-N-methylamide acetate | 0.36 (chloroform:methanol:acetic acid = 10:2:1) | 8.20(2H, d, J=7Hz), 7.96(2H, d, J=7Hz), 7.65-7.50(4H, m), 6.65(1H, m), 4.30-4.10(4H, m), 2.80(3H, br), 2.15(3H, m), 1.95(3H, s), 1.25(3H, m). |
| 1(qqq) | (structure with N-ethyl amide, CH₃COOH) | p-(p-amidino-phenoxycarbonyl)-α-methylcinnamic acid N-ethoxy-carbonylmethyl-N-ethylamide acetate | 0.45 (chloroform:methanol:acetic acid = 10:2:1) | 8.20(2H, d, J=8Hz), 7.90(2H, d, J=9Hz), 7.60-7.50(4H, m), 6.65(1H, m), 4.30-4.10(4H, m), 3.45(2H, m), 2.15(3H, m), 1.95(3H, s), 1.25(3H, m), 0.95(3H, m). |
| 1(rrr) | (structure with N-butyl amide, CH₃COOH) | p-(p-amidino-phenoxycarbonyl)-α-methylcinnamic acid N-ethoxy-carbonylmethyl-N-butylamide acetate | 0.50 (chloroform:methanol:acetic acid = 10:2:1) | 8.22(2H, d, J=8Hz), 7.92(2H, d, J=8Hz), 7.56(4H, t, J=8Hz), 6.70-6.60(1H, m), 4.22(2H, q, J=7Hz), 4.15(2H, s), 3.49(2H, t, J=7Hz), 2.10(3H, s), 1.93(3H, s), 1.80-1.50(2H, m), 1.5-1.2(5H, m), 0.93(3H, brt, J=7Hz). |
| 1(sss) | (structure with N-cyclobutyl amide, CH₃COOH) | p-(p-amidino-phenoxycarbonyl)-α-methylcinnamic acid N-ethoxy-carbonylmethyl-N-cyclobutylamide acetate | 0.53 (chloroform:methanol:acetic acid = 10:2:1) | 8.25(2H, d, J=9.5Hz), 7.90(2H, d, J=8Hz), 7.60-7.50(4H, m), 6.65(1H, brs), 4.25-4.05(5H, m), 2.15(3H, brs), 1.95(3H, s), 2.00-1.05(9H, m). |
| 1(ttt) | (structure with N-cyclopentyl amide, CH₃COOH) | p-(p-amidino-phenoxycarbonyl)-α-methylcinnamic acid N-ethoxy-carbonylmethyl-N-cyclopentylamide acetate | 0.53 (chloroform:methanol:acetic acid = 10:2:1) | 8.25(2H, d, J=9.5Hz), 7.90(2H, d, J=8Hz), 7.60-7.50(4H, m), 6.65(1H, brs), 4.25-4.05(4H, m), 3.80(1H, m), 2.15(3H, m), 2.00-1.80(4H, m), 1.95(3H, s), 1.75-1.05(7H, m). |

TABLE 3-continued

| Ex. No. | Structure | Name | TLC (Rf) | NMR |
|---|---|---|---|---|
| 1(uuu) | (structure) | p-(p-amidino-phenoxycarbonyl)-α-methylcinnamic acid N-2-ethoxycarbonylethyl-N-methylamide acetate | 0.37 (chloroform:methanol:acetic acid = 10:2:1) | 8.20(2H, d, J=7Hz), 7.96(2H, d, J=7Hz), 7.65–7.49(4H, m), 6.65(1H, m), 4.30–4.10(2H, m), 3.80(2H, m), 2.80(3H, br), 2.75(2H, m), 2.15(3H, m), 1.95(3H, s), 1.25(3H, m). |
| 1(vvv) | (structure) | p-(p-amidino-phenoxycarbonyl)-α-methylcinnamic acid N-2-ethoxycarbonylethyl-N-ethylamide acetate | 0.45 (chloroform:methanol:acetic acid = 10:2:1) | 8.20(2H, d, J=8Hz), 7.90(2H, d, J=9Hz), 7.60–7.50(4H, m), 6.65(1H, m), 4.20(2H, m), 3.80(2H, m), 3.45(2H, m), 2.75(2H, m), 2.15(3H, m), 1.95(3H, s), 1.25(3H, m), 0.95(3H, m). |

Example 2 p-(p-Amidinophenoxycarbonyl)cinnamic acid N'-phenylmethyl piperazinylamide bishydrochloride

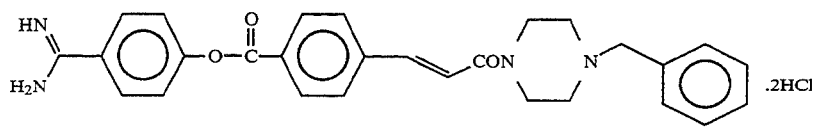

By the same procedure as Example 1, using the compound prepared in Reference Example 12 instead of that prepared in Reference Example 10, the title compound having the following physical data was given.

TLC: Rf 0.24 (chloroform:methanol=8:2); IR: $\nu$3402, 1741, 1678, 1644, 1606, 1479, 1415, 1263, 1216, 1174, 1123, 1070, 1016, 951, 872, 844, 765, 753, 703, 538 cm$^{-1}$; NMR (CD$_3$OD+d$_6$-DMSO): $\delta$8.10 (2H, d), 7.95 (2H, d), 7.86 (2H, d), 7.70 (1H, d), 7.62-7.45 (7H, m), 7.40 (1H, d), 4.80-4.50 (2H, m), 3.80-3.40 (3H, m), 3.50-3.00 (3H, m).

Example 2(a)~2(II)

By the same procedure as a series of reactions of Reference Example 11→Reference Example 12→Example 2, using, as starting materials, the compound prepared in Reference Example 7, that prepared in Reference Example 8, that prepared in Reference Example 14 or p-t-butoxycarbonylbenzoic acid, and further using proper amines instead of N-benzylpiperazine, the compounds of the present invention shown in Table 4 were given.

TABLE 4

| Ex. No. | Structure | Name | TLC (Rf) | NMR |
|---|---|---|---|---|
| 2(a) | [structure: p-amidinophenyl ester of cinnamate with N-phenyl-N-ethoxycarbonylmethyl amide; HCl salt] | p-(p-amidino phenoxycarbonyl) cinnamic acid-N-phenyl-N-ethoxy carbonylmethyl amide hydrochloride | 0.59 (chloroform:methanol:acetic acid = 10:2:1) | 8.15(2H, d), 7.90(2H, d), 7.69(1H, d), 7.60–7.40(9H, m), 6.58(1H, d), 4.52(2H, s), 4.20 (2H, q), 1.25(3H, t). |
| 2(b) | [structure with (2S)-pyrrolidine, C₂H₅OOC; CH₃COOH] | p-(p-amidino phenoxycarbonyl) cinnamic acid-N-(2-(S)-ethoxy carbonyl) pyrrolidinylamide acetic acid | 0.31 (chloroform:methanol:acetic acid = 10:2:1) | 8.20(2H, d), 8.00–7.50(7H, m), 7.15 and 6.95(1H, d), 4.55(1H, m), 4.20(2H, q), 3.90(2H, m), 2.30 (1H, m), 2.20–2.00(3H, m), 2.00 (3H, s), 1.30(3H, t). |
| 2(c) | [structure with (2R)-pyrrolidine, C₂H₅OOC; CH₃COOH] | p-(p-amidino phenoxycarbonyl) cinnamic acid-N-(2-(R)-ethoxy carbonyl) pyrrolidinylamide acetic acid | 0.31 (chloroform:methanol:acetic acid = 10:2:1) | 8.20(2H, d), 8.00–7.50(7H, m), 7.15 and 6.95(1H, d), 4.55(1H, m), 4.20(2H, q), 3.90(2H, m), 2.30(1H, m), 2.20–2.00(3H, m), 2.00(3H, s), 1.30(3H, t). |
| 2(d) | [structure with N-benzyl-N-ethoxycarbonylmethyl amide; CH₃COOH] | p-(p-amidino phenoxycarbonyl) cinnamic acid-N-phenylmethyl-N-ethoxycarbonyl methyl amide acetic acid | 0.48 (chloroform:methanol:acetic acid = 10:2:1) | 8.20(2H, m), 7.90(2H, d), 7.85–7.70(3H, m), 7.55(2H, d), 7.40–7.20(6H, m), 4.95 and 4.75(2H, s), 4.40 and 4.20 (2H, s), 4.20(2H, m), 2.00 (3H, s), 1.25(3H, m). |

TABLE 4-continued

| Ex. No. | Structure | Name | TLC (Rf) | NMR |
|---|---|---|---|---|
| 2(e) | (structure shown) CH₃COOH | p-(p-amidino henoxycarbonyl)-α-methyl-cinnamic acid-N-(2-(S)-benzyloxycarbonyl) pyrrolidinylamide acetic acid | 0.26 (chloroform:methanol:acetic acid = 10:1:1) | 8.21(1.4H, d), 8.13(0.6H, d), 7.92(2H, d), 7.53(3H, m), 7.45-7.20 (5H, m), 6.77(0.7H, s), 6.62(0.3H, s), 5.20(2H, m), 4.61-4.54(1H, m), 3.73(2H, m), 2.11(3H, s), 2.01(3H, m), 1.93 (3H, s) |
| 2(f) | (structure shown) CH₃COOH | p-(p-amidino phenoxycarbonyl) benzoic acid-N-(2-(R)-benzyloxy carbonyl) pyrrolidinyl amide acetic acid | 0.36 (chloroform:methanol:acetic acid = 10:2:1) | 8.30 and 8.10(2H, d), 7.95 (2H, d), 7.70 and 7.45(2H, d), 7.55(2H, d), 7.45-7.25(5H, m), 5.30 and 5.10(1H, d), 5.20 and 4.95(1H, d), 4.70 and 4.50 (1H, m), 3.75 and 3.60(2H, m), 2.40(1H, m), 2.20-1.80 (3H, m), 2.00(3H, s). |
| 2(g) | (structure shown) HCl | p-(p-amidino phenoxycarbonyl) cinnamic acid-N-1-(S),3-bis (ethoxy carbonyl)propyl amide hydrochloride | 0.39 (chloroform:methanol:acetic acid = 15:2:1) | 8.20(2H, d, J = 8.0Hz), 7.93(2H, d, J = 8.0Hz), 7.80(2H, d, J = 8.5Hz), 7.62(1H, d, J = 15Hz), 7.55(2H, d, J = 8.5Hz), 6.83(1H, d, J = 1 5Hz), 4.58(1H, dd, J = 5.0, 8.0Hz), 4.20 (2H, q, J = 8.0Hz), 4.25(2H, q, J = 8.0Hz) 2.45(2H, t, J = 8.0Hz), 2.56-1.95(2H, m), 1.28(3H, t, J = 8.0Hz), 1.23(3H, t, J = 8.0Hz). |

TABLE 4-continued

| Ex. No. | Structure | Name | TLC (Rf) | NMR |
|---|---|---|---|---|
| 2(h) | [structure with p-amidinophenyl, cinnamoyl, COOC₂H₅, benzyloxy groups] · CH₃COOH | p-(p-amidino phenoxycarbonyl)-α-methyl-cinnamic acid-N-(1-(S)-benzyloxycarbonyl-3-ethoxycarbonyl) propyl amide acetic acid | 0.68 (chloroform:methanol:acetic acid = 10:2:1) | 8.20(2H, d, J=8Hz), 7.95 (2H, d, J=8Hz), 7.60–7.50 (4H, m), 7.40–7.30(5H, m), 5.25(1H, d, J=11 Hz), 5.20 (1H, d, J=11Hz), 4.60(1H, m), 4.15(2H, q, J=7Hz), 2.50 (2H, t, J=7.5Hz), 2.40–2.00 (2H, m), 2.15(3H, s), 1.95 (3H, s), 1.25(3H, t, J=7Hz). |
| 2(i) | [structure] · CH₃COOH | p-(p-amidino phenoxycarbonyl) α-methyl-cinnamic acid-N-(1-(S)-ethoxycarbonyl-3-benzyloxycarbonyl) propyl amide acetic acid | 0.70 (chloroform:methanol:acetic acid = 10:2:1) | 8.20(2H, d, J=8Hz), 7.95(2H, d, J=8Hz), 7.60–7.50(4H, m), 7.40–7.30(5H, m), 5.15(2H, m), 4.5–5.5(1H, m), 4.20(2H, q, J=7Hz), 2.60(2H, t, J=7.5Hz), 2.40–2.00(2H, m), 2.15(3H, s), 1.95(3H, s), 1.30(3H, t, J=7Hz). |
| 2(j) | [structure] · HCl | p-(p-amidino phenoxycarbonyl)-(α-methyl-cinnamic acid)-N-(1-(S)-benzyloxycarbonyl-2-ethoxycarbonyl) ethyl amide hydrochloride | 0.48 (chloroform:methanol:acetic acid = 10:2:1) | 8.22(2H, d, J=9.0Hz), 7.94(2H, d, J=9.0Hz), 7.55(2H, d, J=9.0Hz), 7.52(2H, d, J=9.0Hz), 7.35(5H, s), 7.31(1H, s), 4.95 (1H, t, J=6.0Hz), 4.14(2H, q, J=7.0Hz), 2.86–3.08(2H, m), 2.13 (3H, s), 1.22(3H, t, J=7.0Hz). |
| 2(k) | [structure] · CH₃COOH | p-(p-amidino phenoxycarbonyl)-α-methyl-cinnamic acid-N-(1-(S)-benzyloxycarbonyl-2-isobutyloxy carbonyl)ethyl amide acetic acid | 0.49 (chloroform:methanol:acetic acid = 10:2:1) | 8.10(2H, d, J=9.0Hz), 7.79(2H, d, J=9.0Hz), 7.40(2H, d, J=9.0Hz), 7.36(2H, d, J=9.0Hz), 7.23(6H, s), 5.12(2H, s), 4.88(1H, t, J=6.0Hz), 3.76(2H, d, J=7.0Hz), 2.92(2H, t, J=6.0Hz), 2.02(3H, d, J=1.0Hz), 1.78(1H, sep, J=7.0Hz), 0.90(6H, d, J=7.0Hz). |

TABLE 4-continued

| Ex. No. | Structure | Name | TLC (Rf) | NMR |
|---|---|---|---|---|
| 2(l) | [structure with benzyloxycarbonyl group, CH₃COOH] | p-(p-amidino phenoxycarbonyl)-α-methyl-cinnamic acid-N-(1-(S)-ethoxycarbonyl-2-benzyloxycarionyl) ethyl amide acetic acid | 0.46 (chloroform:methanol:acetic acid = 10:2:1) | 8.22(2H, d, J=9.0Hz), 7.93(2H, d, J=9.0Hz), 7.57–7.48(4H, m), 7.36(6H, s), 5.18(2H, s), 4.95(1H, t, J=6.0Hz), 4.22(2H, q, J=7.0Hz), 3.04(2H, d, J=6.0Hz), 2.11(3H, s), 1.26(3H, t, J=7.0Hz). |
| 2(m) | [structure with N-allyl group, CH₃COOH] | p-(p-amidino phenoxycarbonyl)-α-methyl-cinnamic acid-N-(2-ethoxy carbonyl)ethenyl-N-allyl amide acetic acid | 0.37 (chloroform:methanol:acetic acid = 10:1:1) | 8.21(2H, d, J=8.4Hz), 7.93(2H, d, J=8.8Hz), 7.57(2H, d, J=8.4Hz), 7.53(2H, d, J=8.8Hz), 6.92(1H, dt, J=15.8, 5.2Hz), 6.70(1H, s), 5.96(1H, d, J=15.8Hz), 6.00–5.80(1H, m), 5.35–5.20(2H, m), 4.20(2H, q, J=7.2Hz), 4.23(2H, d, J=5.2Hz), 4.11(2H, d, J=5.2Hz), 2.15(3H, s), 1.93(3H, s), 1.29(3H, t, J=7.2Hz). |
| 2(n) | [structure with 4-ethoxycarbonylphenylmethylthio group, CH₃SO₃H] | p-(p-amidino phenoxycarbonyl)-α-methyl-cinnamic acid-N-(1-(S)-ethoxycarbonyl-2-(4-ethoxycarbonyl phenylmethylthio) ethyl amide methane sulfonic acid | 0.69 (chloroform:methanol:acetic acid = 10:2:1) | 8.22(2H, d, J=9.0Hz), 7.99(2H, d, J=9.0Hz), 7.94(2H, d, J=9.0Hz), 7.56(2H, d, J=9.0Hz), 7.50(2H, d, J=9.0Hz), 7.45(2H, d, J=9.0Hz), 7.38(1H, s), 4.70–4.80(1H, m), 4.36(2H, q, J=7.0Hz), 4.22(2H, q, J=7.0Hz), 3.83(2H, s), 3.00(1H, dd, J=14.0, 5.0Hz), 2.85(1H, dd, J=14.0, 9.0Hz), 2.17(3H, s), 1.39(3H, t, J=7.0Hz), 1.30(3H, t, J=7.0Hz). |

TABLE 4-continued

| Ex. No. | Structure | Name | TLC (Rf) | NMR |
|---|---|---|---|---|
| 2(o) | [structure with COOC2H5, CH3SO3H] | p-(p-amidino phenoxycarbonyl)-α-methyl-cinnamic acid-N-(1-(S)-ethoxycarbonyl-2-(3-ethoxycarbonyl phenylmethylthio)) ethyl amide methane sulfonic acid | 0.69 (chloroform:methanol:acetic acid = 10:2:1) | 8.23(2H, d, J=9.0Hz), 8.02(1H, s), 7.91(3H, d, J=9.0Hz), 7.57 (2H, d, J=9.0Hz), 7.52(2H, d, J=9.0Hz), 7.42–7.58(2H, m), 7.39 (1H, s), 4.78–4.70(1H, m), 4.38 (2H, q, J=7.0Hz), 4.21(2H, q, J=7.0Hz), 3.86(2H, s), 3.01(1H, dd, J=14.0, 5.0Hz), 2.88(1H, dd, J=14.0, 9.0Hz), 2.16(3H, d, J=2.0Hz), 1.40(3H, t, J=7.0Hz), 1.28(3H, t, J=7.0Hz). |
| 2(p) | [structure with COOC2H5, CH3SO3H] | p-(p-amidino phenoxycarbonyl)-α-methyl-cinnamic acid-N-(1-(S)-ethoxycarbonyl-2-(3-ethoxy-carbonyl) 2-(2-propenylthio)) ethyl amide methane sulfonic acid | 0.69 (chloroform:methanol:acetic acid = 10:2:1) | 8.22(2H, d, J=9Hz), 7.92(2H, d, J= 9Hz), 7.60(2H, d, J=9 Hz), 7.52 (2H, d, J=9Hz), 7.37(1H, s), 6.88(1H, ddd, J=15.0, 7.5, 7.5Hz), 5.98(1H, d, J=15.0Hz), 4.66(1H, dd, J=9.0,5.0Hz), 4.22 (2H, q, J=7.0Hz), 4.18(2H, q, J=7Hz), 3.36(2H, d, J=7.5Hz), 3.08(1H, dd, J=14.0,5Hz), 2.88 (1H, dd, J=14.0, 9Hz), 2.15(3H, d, J=2.0Hz), 1.31(3H, t, J=7Hz), 1.27(3H, t, J=7Hz). |
| 2(q) | [structure with COOC2H5, CH3SO3H] | p-(p-amidino phenoxycarbonyl)-α-methyl-cinnamic acid-N-(1-(S)-ethoxycarbonyl-2-(2-ethoxycarbonyl phenylthio)) ethyl amide methane sulfonic acid | 0.41 (chloroform:methanol:acetic acid = 10:2:1) | 8.21(2H, d, J=9.0Hz), 7.92(2H, d, J=9.0Hz), 7.84–7.90(1H, m), 7.58–7.49(6H, m), 7.29–7.20 (2H, m), 4.78(1H, dd, J=8.0, 5.0Hz), 4.37(2H, q, J=7.0Hz), 4.21(2H, q, J=7.0Hz), 3.61(1H, dd, J=15.0,5.0Hz), 3.42(1H, dd, J=15.0, 8.0Hz), 2.09(3H, d, J= 2.0Hz), 1.39(3H, t, J=7.0Hz), 1.30(3H, t, J=7.0Hz). |
| 2(r) | [structure with COOC2H5, HCl] | p-(p-amidino phenoxycarbonyl)-α-methyl-cinnamic acid-N-ethoxy carbonylmethyl-N-3-methyl-2-butenyl amide hydrochloride | 0.59 (chloroform:methanol:acetic acid = 10:2:1) | 8.20(2H, d, J=8Hz), 7.90 (2H, d, J=8Hz), 7.60–7.50 (4H, m), 6.70(1H, br), 5.25 (1H, br), 4.30–4.00(6H, m), 2.15(3H, brs), 1.80(3H, brs), 1.65(3H, s), 1.30(3H, t, J=7.5Hz). |

TABLE 4-continued

| Ex. No. | Structure | Name | TLC (Rf) | NMR |
|---|---|---|---|---|
| 2(s) | [structure with 2-ethoxycarbonylphenyl group, CH₃COOH] | p-(p-amidino phenoxycarbonyl)-α-methyl-cinnamic acid-N-(2-ethoxy carbonylphenyl) methyl-N-allyl amide acetic acid | 0.58 (chloroform:methanol:acetic acid = 10:2:1) | 8.18(2H, br), 7.99(1H, d, J=7.5Hz), 7.92(2H, d, J=9.0Hz), 7.48(2H, d, J=9.0Hz), 7.60–7.37 (5H, m), 6.72–6.60(1H, m), 5.98–5.78(1H, m, ddd, J=22.0, 11.0, 5.0Hz), 5.28–5.15(2H, m), 5.08 (2H, s), 4.34(2H, q, J=7.0Hz), 4.08(2H, d, J=6.0Hz), 2.17(3H, br), 1.38(3H, t, J=7.0Hz). |
| 2(t) | [structure with 3-ethoxycarbonylphenyl group, HCl] | p-(p-amidino phenoxycarbonyl)-(α-methyl-cinnamic acid-N-(3-ethoxy carbonylphenyl) methyl-N-allyl amide hydrochloride | 0.30 (chloroform:methanol:acetic acid = 10:1:1) | 8.20(2H, d, J=8.0Hz), 7.93(4H, d, J=8.8Hz), 7.60–7.45(6H, m), 6.71(1H, s), 6.00–5.80(1H, m), 5.35–5.20(2H, m), 4.75(2H, s), 4.37(2H, q, J=7.0Hz), 4.08(2H, d, J=5.6Hz), 2.16(3H, s), 1.39 (3H, t, J=7.0Hz). |
| 2(u) | [structure with 4-ethoxycarbonylphenyl group, CH₃SO₃H] | p-(p-amidino phenoxycarbonyl)-α-methyl-cinnamic acid-N-(4-ethoxy carbonylphenyl) methyl-N-allyl amide methane sulfonic acid | 0.39 (chloroform:methanol:acetic acid = 10:1:1) | 8.20(2H, d, J=8.0Hz), 8.03(2H, d, J=8.4Hz), 7.93(2H, d, J=8.5Hz), 7.53(4H, d, J=8.4Hz), 7.42(2H, d, J=8.4Hz), 6.71(1H, s), 6.00–5.80(1H, m), 5.38–5.15 (2H, m), 4.76(2H, s), 4.37(2H, q, J=7.2Hz), 4.08(2H, d, J=5.4Hz), 2.72(3H, s), 2.16(3H, s), 1.39(3H, t, J=7.2Hz). |
| 2(v) | [structure with 3-ethoxycarbonyl-2-propenyl group, CH₃COOH] | p-(p-amidino phenoxycarbonyl)-α-methyl-cinnamic acid-N-(3-ethoxy carbonyl-2-propenyl)-N-ethoxy carbonylmethyl amide acetic acid | 0.48 (chloroform:methanol:acetic acid = 10:1:1) | 8.21(2H, d, J=8.2Hz), 7.93 (2H, d, J=8.8Hz), 7.56(2H, d, J=8.2Hz), 7.53(2H, d, J=8.8Hz), 7.05–6.85(1H, m), 6.72 (1H, s), 6.20–5.90(1H, m), 4.40–4.00(8H, m), 2.14(3H, s), 1.93(3H, s), 1.35–1.10(6H, m). |

TABLE 4-continued

| Ex. No. | Structure | Name | TLC (Rf) | NMR |
|---|---|---|---|---|
| 2(w) | [structure with COOC$_2$H$_5$, H$_3$C, allyl-N, amidino phenyl ester; CH$_3$COOH] | p-(p-amidino phenoxycarbonyl)-(α-methyl-cinnamic acid-N-3-ethoxy carbonylpropyl-N-allyl amide acetic acid | 0.47 (chloroform:methanol:acetic acid = 10:1:1) | 8.22(2H, d, J=8.4Hz), 7.92(2H, d, J=8.8Hz), 7.56(2H, d, J=8.8Hz), 7.52(2H, d, J=8.4Hz), 6.64(1H, s), 6.00–5.80(1H, m), 5.35 14 5.20(2H, m), 4.10(4H, m), 3.48(2H, t, J=7.0Hz), 2.38(2H, brt), 2.13(3H, s), 2.00–1.85(2H, m), 1.94(3H, s), 1.24(3H, brt). |
| 2(x) | [structure with CH$_3$, hexadienyl-N-ethyl ester, amidino phenyl ester; HCl] | p-(p-amidino phenoxycarbonyl)-(α-methyl-cinnamic acid-N-ethoxy carbonylmethyl-N-2,4-hexadienyl amide hydrochloride | 0.56 (chloroform:methanol:acetic acid = 10:2:1) | 8.20(2H, d, J=8.5Hz), 7.94(2H, d, J=8.5Hz), 7.55(2H, d, J=8.0Hz), 7.51(2H, d, J=8.0Hz), 6.70(1H, brs), 6.20(1H, dd, J=5.0, 15.0Hz), 6.07(1H, t, J=15.0Hz), 5.75(1H, ddd, J=7.5, 15.0Hz), 5.62–5.40(1H, m), 4.20 (2H, q, J=7.5Hz), 4.15(2H, d, J=7.5Hz), 2.18(3H, s), 1.78(3H, d, J=5.0Hz), 1.28(3H, t, J=7.5Hz). |
| 2(y) | [structure with two COOC$_2$H$_5$, allyl-N, H$_3$C, amidino phenyl ester; HCl] | p-(p-amidino α-methyl-cinnamic acid-N-1-(S), 2-bis (ethoxycarbonyl) ethyl-N-anyl amide hydrochloride | 0.45 (chloroform:methanol:acetic acid = 10:2:1) | 8.21(2H, d, J=8.0Hz), 7.57(2H, d, J=7.5Hz), 6.71(1H, brs), 6.10–5.80(1H, m), 5.50–5.10 (2H, m), 4.60–4.40(1H, m), 4.40–4.00(2H, m), 4.16(4H, q, J=7.5Hz), 3.40–3.15(1H, m), 2.89 (1H, dd, J=5.0, 15.0Hz), 2.17(3H, s), 1.28(6H, t, J=7.5Hz). |
| 2(z) | [structure with two COOC$_2$H$_5$, H, H$_3$C, amidino phenyl ester with COOCH$_3$; CH$_3$COOH] | p-(p-amidino-o-methoxycarbonyl) phenoxycarbonyl)-α-methyl-cinnamic acid-N-1-(S), 3-bis (ethoxycarbonyl) propyl amide acetic acid | 0.54 (chloroform:methanol:acetic acid = 10:2:1) | 8.49(1H, d, J=2.0Hz), 8.22(2H, d, J=9.0Hz), 8.10(1H, dd, J=9.0, 2.0Hz), 7.62(2H, d, J=9.0Hz), 7.58(1H, d, J=9.0Hz), 7.35(1H, s), 4.54(1H, dd, J=9.5, 5.0Hz), 4.21(2H, q, J=7.0Hz), 4.14(2H, q, J=7.0Hz), 3.79(3H, s), 2.49(2H, t, J=7.0Hz), 2.02–2.37(2H, m), 2.15(3H, s), 1.29(3H, t, J=7.0Hz), 1.25(3H, t, J=7.0Hz). |

TABLE 4-continued

| Ex. No. | Structure | Name | TLC (Rf) | NMR |
|---|---|---|---|---|
| 2(aa) | [structure: p-amidinophenyl 4-{(E)-2-methyl-3-[N-(1-ethoxycarbonyl-2-methylpropyl)-N-ethoxycarbonylmethyl)amino]-3-oxo-1-propenyl}benzoate · CH₃COOH] | p-(p-amidino phenoxycarbonyl)-α-methyl-cinnamic acid-N-ethoxy carbonylmethyl-N-isopropyl amide acetic acid | 0.38 (chloroform:methanol:acetic acid = 10:2:1) | 8.21(2H, d, J=9.0Hz), 7.94(2H, d, J=9.0Hz), 7.58(2H, d, J=9.0Hz), 7.53(2H, d, J=9.0Hz), 6.68(1H, s), 4.33(1H, m), 4.20(2H, q, J=7.0Hz), 4.06(2H, s), 2.15(3H, s), 1.29(3H, t, J=7.0Hz), 1.22(6H, d, J=7.0Hz) |
| 2(bb) | [structure with isobutyl and COOC₂H₅ · HCl] | p-(p-amidino phenoxycarbonyl)-(α-methyl-cinnamic acid-N-(1-(S)-ethoxycarbonyl-3-methyl)butyl amide hydrochloride | 0.40 (chloroform:methanol:acetic acid = 10:1:1) | 9.38(1H, brs), 8.83(1H, brs), 8.21(2H, d, J=8.0Hz), 7.95(2H, d, J=8.0Hz), 7.60(2H, d, J=8.0Hz), 7.56(2H, d, J=8.0Hz), 7.73(1H, s), 4.60-4.48(1H, m), 4.20(2H, q, J=7.5Hz), 2.13(3H, s), 1.90-1.60(3H, m), 1.25(3H, t, J=7.5Hz), 1.00(3H, d, J=7.5Hz), 0.97(3H, d, J=7.5Hz) |
| 2(cc) | [structure with N-allyl, CH₂COOC₂H₅ · CH₃COOH] | p-(p-amidino phenoxycarbonyl)phenylpropionic acid-N-ethoxy carbonylmethyl-N-allyl amide acetic acid | 0.37 (chloroform:methanol:acetic acid = 10:1:1) | 8.11(2H, d, J=8.4Hz), 7.91(2H, d, J=8.8Hz), 7.51(2H, d, J=8.8Hz), 7.46(2H, d, J=8.4Hz), 6.00-5.70(1H, m), 5.22-5.11(2H, m), 4.18(2H, q, J=7.0Hz), 4.06(4H, brs), 3.06(2H, t, J=7.0Hz), 2.81(2H, m), 1.92(3H, s), 1.26(3H, t, J=7.0Hz) |
| 2(dd) | [structure with two COOC₂H₅ groups · HCl] | p-(p-amidino phenoxycarbonyl)-α-methyl-cinnamic acid-N-1-(S), 2-bis (ethoxycarbonyl) ethyl-N-2-ethoxy carbonyl ethyl amide hydrochloride | 0.49 (chloroform:methanol:acetic acid = 10:1:1) | 8.21(2H, d, J=8.0Hz), 7.95(2H, d, J=8.0Hz), 7.59(2H, d, J=7.5Hz), 7.56(2H, d, J=7.5Hz), 6.65(1H, s), 4.6-4.40(1H, m), 4.30-4.02(6H, m), 4.05-3.60(2H, m), 3.30-3.15(1H, m), 2.96(1H, dd, J=7.5, 17.0Hz), 2.82-2.60(2H, m), 2.15(3H, s), 1.28(6H, t, J=7.5Hz), 1.22(3H, t, J=7.5Hz). |

| Ex. No. | Structure | Name | TLC (Rf) | NMR |
|---|---|---|---|---|
| 2(ee) | (structure) · CH₃COOH | p-(p-amidino phenoxycarbonyl)-α-methyl-cinnamic acid-N-ethoxy carbonylmethyl-N-propyl amide acetic acid | 0.46 (chloroform:methanol:acetic acid = 10:2:1) | 8.20(2H, d, J=8Hz), 7.90(2H, d, J=9Hz), 7.60–7.50(4H, m), 6.65 (1H, m), 4.30–4.10 (4H, m), 3.45 (2H, m), 2.15(3H, m), 1.70(2H, m), 1.25(3H, m), 0.95(3H, m). |
| 2(ff) | (structure) · CH₃COOH | p-(p-amidino phenoxycarbonyl)-α-methyl-cinnamic acid-N-1-(S)-ethoxy carbonyl-2-methyl) propyl amide acetic acid | 0.46 (chloroform:methanol:acetic acid = 10:2:1) | 8.20(2H, d, J=8.5Hz), 7.90(2H, d, J=9Hz), 7.60(2H, d, J=8.5Hz), 7.55(2H, d, J=9Hz), 7.30(1H, brs), 4.40(1H, d, J=6.5Hz), 4.20 (2H, q, J=7Hz), 2.20(1H, m), 2.15 (3H, s), 1.95(3H, s), 1.30(3H, t, J=7Hz), 1.00(6H, m). |
| 2(gg) | (structure) · CH₃COOH | m-(p-amidino phenoxycarbonyl)-α-methyl-cinnamic acid-N-ethoxy carbonylmethyl-N-allyl amide acetic acid | 0.41 (chloroform:methanol:acetic acid = 10:2:1) | 8.15(2H, m), 7.95(2H, d, J=8Hz), 7.80–7.60(2H, m), 7.55 (2H, d, J=8Hz), 6.75(1H, m), 5.90(1H, m), 5.40–5.20(2H, m), 4.30–4.10(6H, m), 2.15 (3H, br), 1.30(3H, m). |

TABLE 4-continued

| Ex. No. | Structure | Name | TLC (Rf) | NMR |
|---|---|---|---|---|
| 2(hh) | *(structure with COOC$_2$H$_5$ groups, amide, α-methylcinnamic acid moiety, p-amidinophenyl ester; HCl)* | m-(p-amidino phenoxycarbonyl)-α-methyl-cinnamic acid-N-1-(S), 3-bis (ethoxycarbonyl) propyl amide hydrochloride | 0.41 (chloroform:methanol:acetic acid = 10:2:1) | 8.25–8.15(2H, m), 7.95(2H, d, J=8Hz), 7.80–7.60(4H, m), 7.55(2H, d, J=8Hz), 7.35(1H, br), 4.55(1H, dd, J=8.5, 6Hz), 4.20(2H, q, J=7.5Hz), 4.15(2H, q, J=7.5Hz), 2.50(2H, t, J=7Hz), 2.40–2.00(2H, m), 2.15(3H, s), 1.30(3H, t, J=7.5Hz), 1.25(3H, t, J=7.5Hz). |
| 2(ii) | *(structure with COOC$_2$H$_5$ groups, amide, phenylpropionic acid moiety, p-amidinophenyl ester; CH$_3$COOH)* | p-(p-amidino phenoxycarbonyl) phenylpropionic acid-N-1-(S) (ethoxycarbonyl) propyl amide acetic acid | 0.35 (chloroform:methanol:acetic acid = 10:1:1) | 8.11(2H, d, J=8.4Hz), 7.92(2H, d, J=8.8Hz), 7.52(2H, d, J=8.8Hz), 7.45(2H, d, J=8.4Hz), 4.20(1H, m), 4.16(2H, q, J=7.2Hz), 4.10(2H, q, J=7.2Hz), 3.05(2H, t, J=7.2Hz), 2.62(2H, t, J=7.2Hz), 2.23(2H, m), 2.20–1.80 (2H, m), 1.93(3H, s), 1.25(3H, t, J=7.2Hz), 1.23(3H, t, J=7.2Hz). |
| 2(jj) | *(structure with COOC$_2$H$_5$, N-isopropyl amide, α-methylcinnamic acid moiety, p-amidinophenyl ester; CH$_3$COOH)* | p-(p-amidino-phenoxycarbonyl)-α-methylcinnamic acid N-(2-ethoxycarbonylethyl)-N-isopropylamide acetate | 0.40 (chloroform:methanol:acetic acid = 10:2:1) | 8.20(2H, d, J=9.0Hz), 7.92(2H, d, J=9.0Hz), 7.57(2H, d, J=9.0Hz), 7.53(2H, d, J=9.0Hz), 6.60(1H, s), 4.29(1H, m), 4.25(2H, q, J=7.0Hz), 3.60(2H, t, J=7.0Hz), 2.69(2H, t, J=7.0Hz), 2.14(3H, s), 1.27(6H, d, J=7.0Hz). |

TABLE 4-continued

| Ex. No. | Structure | Name | TLC (Rf) | NMR |
|---|---|---|---|---|
| 2(kk) | [structure with p-amidinophenoxycarbonyl group, α-methylcinnamic acid derivative, CH$_3$COOH] | p-(p-amidino-phenoxycarbonyl)-α-methylcinnamic acid N-(1,2-bis(ethoxycarbonyl)ethyl)-N-3-ethoxy-carbonyl-2-propenylamide acetate | 0.47 (chloroform:methanol = 8:2) | 8.23(2H, d, J = 8Hz), 7.93(2H, d, J = 8Hz), 7.65–7.50(4H, m), 7.13–6.80(2H, m), 6.30–6.10(1H, m), 4.60–4.00 (3H, m), 4.27–4.10 (6H, m), 3.01–2.84 2 H, m), 2.13(3 H, bs), 1.35–1.13(9H, m). |
| 2(ll) | [structure with p-amidinophenoxycarbonyl group, methylcinnamic acid derivative, CH$_3$COOH] | p-(p-amidino-phenoxycarbonyl)-α-methylcinnamic acid N-(1-(S),3-bis(ethoxycarbonyl)propyl)-N-allyl amide acetate | 0.38 (chloroform:methanol:acetic acid = 20:2:1) | 8.22(2H, d, J = 8.5Hz), 7.93(2H, d, J = 8.5Hz), 7.58(2H, d, J = 8.5Hz), 7.53(2H, d, J = 8.5Hz), 6.69(1H, s), 6.10–5.80(1H, m), 5.50–5.10 (2H, m), 4.20(4H, q, J = 7.5Hz), 4.30–3.80(3H, m), 2.60–2.35(4H, m), 2.13(3H, s), 1.92(3H, s), 1.30 (6H, t, J = 7.5Hz). |

Reference Example 15 p-Methoxycarbonyl-α-methylcinnamic acid t-butyl ester

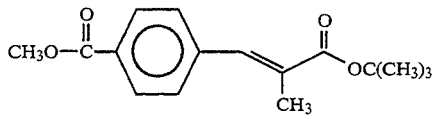

By the same procedure as Reference Example 1, using p-methoxycarbonylbenzaldehyde instead of p-benzyloxycarbonylbenzaldehyde, the title compound having the following physical data was given:

TLC: Rf 0.67 (hexane:ethyl acetate=4:1).

Reference Example 16 p-Carboxy-α-methylcinnamic acid t-butyl ester

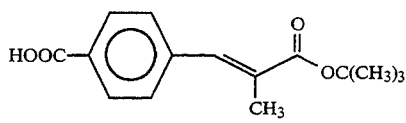

By the same procedure as Reference Example 7, using the compound prepared in Reference Example 15, the title compound having the following physical data was given:

TLC: Rf 0.42 (ethyl acetate).

Reference Example 17 p-(p-Amidinophenoxycarbonyl)-α-methylcinnamic acid t-butyl ester

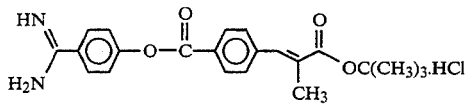

By the same procedure as Example 1, using the compound prepared in Reference Example 16, the title compound having the following physical data was given.:

TLC: Rf 0.41 (chloroform:methanol:acetic acid=10:2:1).

Reference Example 18 p-(p-Amidinophenoxycarbonyl)-α-methylcinnamic acid hydrochloride

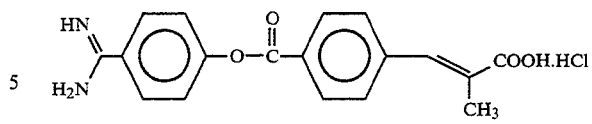

To a solution of the compound prepared in Reference Example 17 (4.79 g) in chloroform (100 ml), were added successively a solution of 4N hydrochloric acid in ethyl acetate (50 ml) and dioxane (10 ml). The mixture was stirred for two hours at room temperature and evaporated. The residue thus obtained was washed with ether, filtered and then dried to give the title compound (4.15 g) having the following physical data:

TLC: Rf 0.38 (chloroform:methanol:acetic acid=10:2:1); NMR: δ5 8.21 (2H, d, J=8.0 Hz), 7.95 (2H, d, J=8.0 Hz), 7.75 (1H, s), 7.60 (2H, d, J=8.0 Hz), 7.54 (2H, d, J=8.0 Hz), 2.12 (3H, s).

Example 3 p-(p-Amidinophenoxycarbonyl)-α-methylcinnamic acid N-t-butoxycarbonylmethyl-N-allylamide acetate

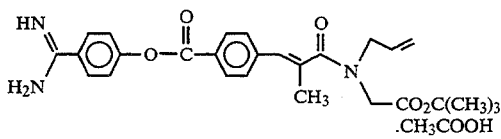

To a suspension of the compound prepared in Reference Example 18 (3.2 g) in a mixture of pyridine (50 ml) and dimethylformamide (5 ml), were added successively a solution of N-t-butoxycarbonylmethyl-N-allylamine (1.52 g) in pyridine (5 ml) and a solution of 1.3-dicyclohexylcarbodiimide (2.20 g) in pyridine (5 ml). The mixture was stirred overnight at room temperature and evaporated. The residue thus obtained was purified by silica gel column chromatography (chloroform:methanol:acetic acid=50:2:1→40:2:1→30:2:1→10:2:1) to give the title compound (683 mg) having the following physical data:

TLC: Rf 0.36 (chloroform:methanol:acetic acid=10:2:1).

Example 3(a)~3(g)

By the same procedure as Example 3, using, as a starting material, the compound prepared in Reference Example 18, and further using a corresponding amine instead of N-t-butoxycarbonylmethyl-N-allylamine, the compounds of the present invention shown in Table 5 were given.

TABLE 5

| Ex. No. | Structure | Name | TLC (Rf) | NMR |
|---|---|---|---|---|
| 3(a) | (structure with N-isobutyl, COOC₂H₅ group; p-amidinophenyl ester; CH₃COOH) | p-(p-amidino-phenoxycarbonyl)-α-methylcinnamic acid N-ethoxy-carbonylmethyl-N-isobutylamide acetate | 0.405 (chloroform:methanol:acetic acid = 10:2:1) | 8.20(2H, d, J=7Hz), 7.95(2H, d, J=7Hz), 7.65–7.50(4H, m), 6.65(1H, m), 4.40–4.15(4H, m), 3.35(2H, m), 2.15(3H, m), 2.00(1H, m), 1.90(3H, s), 1.30(3H, m), 1.00(6H, d, J=7Hz). |
| 3(b) | (structure with N-isopentyl, COOC₂H₅; p-amidinophenyl ester; CH₃COOH) | p-(p-amidino-phenoxycarbonyl)-α-methylcinnamic acid N-ethoxy-carbonylmethyl-N-isopentylamide acetate | 0.378 (chloroform:methanol:acetic acid = 10:2:1) | 8.20(2H, d, J=7Hz), 7.95(2H, d, J=7Hz), 7.65–7.50(4H, m), 6.65(1H, m), 4.30–4.10(4H, m), 3.50(2H, s), 2.15(3H, m), 1.95(3H, s), 1.70–1.40(3H, m), 1.25(3H, m), 0.90(6H, m). |
| 3(c) | (structure with N-cyclopropyl, COOC₂H₅; p-amidinophenyl ester; CH₃COOH) | p-(p-amidino-phenoxycarbonyl)-α-methylcinnamic acid N-cyclopropyl-N-ethoxycarbonyl-methylamide acetate | 0.365 (chloroform:methanol:acetic acid = 10:2:1) | 8.20(2H, d, J=7Hz), 7.95(2H, d, J=7Hz), 7.65–7.50(4H, m), 6.85(1H, m), 4.20(2H, q, J=7Hz), 4.20(2H, s), 3.00(1H, br.), 2.20(3H, s), 1.95(3H, s), 1.30(3H, t, J=7Hz), 0.95–0.90(4H, m). |
| 3(d) | (structure with N-allyl, COOC₂H₅; p-amidinophenyl ester; CH₃COOH) | p-(p-amidino-phenoxycarbonyl)-α-methylcinnamic acid N-allyl-N-2-ethoxycarbonyl-ethylamide acetate | 0.556 (chloroform:methanol:acetic acid = 10:2:1) | 8.20(2H, d, J=7.5Hz), 7.90(2H, d, J=7.5Hz), 7.60–7.50(4H, m), 6.65(1H, br.), 5.90(1H, m), 5.40–5.20(2H, m), 4.20–4.05(4H, m), 3.75(2H, m), 2.70(2H, m), 2.10(3H, s), 1.95(3H, s), 1.25(3H, m). |

TABLE 5-continued

| Ex. No. | Structure | Name | TLC (Rf) | NMR |
|---|---|---|---|---|
| 3(e) | [structure: p-amidinophenyl ester of cinnamate with COOC₂H₅ and N-propyl amide, HCl salt] | p-(p-amidino-phenoxycarbonyl)-α-methylcinnamic acid N-2-ethoxy-carbonylethyl-N-propylamide acetate | 0.569 (chloroform:methanol:acetic acid = 10:2:1) | 8.25(2H, d, J=7.5Hz), 7.95(2H, d, J=7.5Hz), 7.60–7.50(4H, m), 6.60(1H, brs), 4.15(2H, q, J=7Hz), 3.75(2H, m), 3.45(2H, m), 2.70(2H, m), 2.15(3H, s), 1.95(3H, s), 1.70(2H, m), 1.25(3H, m), 0.95(3H, m). |
| 3(f) | [structure: similar with N-2-ethoxycarbonylethyl-N-ethoxycarbonylmethyl, CH₃COOH salt] | p-(p-amidino-phenoxycarbonyl)-α-methylcinnamic acid N-2-ethoxycarbonylethyl-N-ethoxycarbonyl-methylamide acetate | 0.50 (chloroform:methanol:acetic acid = 10:2:1) | 8.25(2H, br.d, J=8Hz), 7.95(2H, d, J=8Hz), 7.80–7.40(4H, m), 6.70(1H, m), 4.45–4.05(6H, m), 3.80(2H, m), 2.70(2H, t, J=7.5Hz), 2.20–2.00(3H, m), 1.95(3H, s, CH₃COOH), 1.25(6H, m). |
| 3(g) | [structure: similar with N-cyclohexyl-N-ethoxycarbonylmethyl, CH₃COOH salt] | p-(p-amidino-phenoxycarbonyl)-α-methylcinnamic acid N-cyclohexyl-N-ethoxycarbonyl-methylamide acetate | 0.55 (chloroform:methanol:acetic acid = 10:2:1) | 8.25(2H, d, J=9.5Hz), 7.90(2H, d, J=8Hz), 7.60–7.50(4H, m), 6.65(1H, br.s), 4.25–4.05(4H, m), 3.80(1H, m), 2.15(3H, br.s), 2.00–1.80(4H, m), 1.75–1.05(6H, m). |

Example 4

P-(P-Amidinophenoxycarbonyl)-α-methylcinnamic acid N-carboxymethyl-N-allylamide methanesulfonate

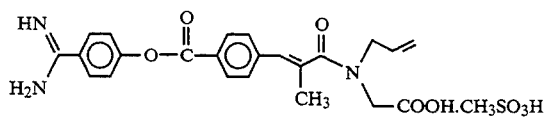

To a solution of the compound prepared in Example 3 (683 mg) in chloroform (10 ml), was added a solution of 4N hydrochloric acid in ethyl acetate (6 ml). The mixture was stirred for one hour at room temperature, and then evaporated. The residue thus obtained was purified by silica gel column chromatography (chloroform:methanol:acetic acid=50:2:1→40:2:1→30:2:1→10:2:1). To the purified compound thus obtained, was added methanesulfonic acid. The mixture was stirred for 10 min. at room temperature and evaporated. The residue was crystallized from a mixture of ether and acetone. The crystals thus obtained was collected by filtration and dried to give he title compound (286 mg) having the following physical data:

TLC: Rf 0.32 (chloroform:methanol:acetic acid=10:2:1); NMR: δ8.20 (2H, d, J=8.0 Hz), 7.95 (2H, d, J=8.0 Hz), 7.58 (2H, d, J=8.0 Hz), 7.52 (2H, d, J=8.0 Hz), 6.80–6.62 (1H, m), 6.78–6.00 (1H, m), 5.40–5.20 (2H, m), 4.20–4.05 (4H, m), 2.70 (6H, s), 2.19–2.05 (3H, m).

Example 4(a)

p-(p-Amidinophenoxycarbonyl)-α-methylcinnamic acid N-3-carboxypropyl-N-allylamide methanesulfonate

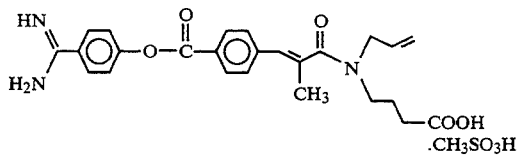

By the same procedure as a series of reactions of Example 3→Example 4, using, as a starting material, the compound prepared in Reference Example 18, and further using a corresponding amine, the title compound having the following physical data was given.

TLC: Rf 0.48 (chloroform:methanol:acetic acid=10:2:1); NMR: δ8.21 (2H, d, J=8.0 Hz), 7.90 (2H, d, J=8.0 Hz), 7.58 (2H, d, J=8.0 Hz), 7.55 (2H, d, J=8.0 Hz), 6.62 (1H, s), 6.02–5.79 (1H, m), 5.38–5.20 (2H, m), 4.10 (2H, d, J=5.0 Hz), 3.50 (2H, t, J=7.5 Hz), 2.75 (3H, s, MeSO$_3$H), 2.48–2.30 (2H, m), 1.98 (2H, tt, J=7.5, 5.0 Hz).

Example 4(b)

p-(p-Amidinophenoxycarbonyl)-α-methylcinnamic acid N-(1-(S)-ethoxycarbonyl-3-carboxy)propylamide hydrochloride

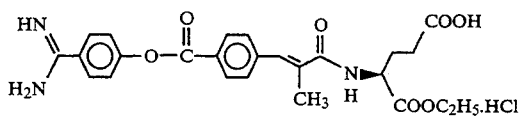

By the same procedure as a series of reactions of Example 3→Example 4, using, as a starting material, the compound prepared in Reference Example 18, and further using a corresponding amine, the title compound having the following physical data was given.

TLC: Rf 0.32 (chloroform:methanol:acetic acid=10:2:1); NMR: δ8.22 (2H, d, J=9.0 Hz), 7.93 (2H, d, J=9.0 Hz), 7.60 (2H, d, J=9.0 Hz), 7.54 (2H, d, J=9.0 HZ), 7.35 (1H, s), 4.52 (1H, dd, J=9.0 Hz, 5.0 Hz), 4.21 (2H, q, J=7.0 Hz), 2.48 (2H, t, J=7.0 Hz), 2.35–1.97 (2H, m), 2.13 (3H, s), 1.28 (3H, t, J=7.0Hz).

Example 5(a)~5(gg)

By the same procedure as a series of reactions of Reference Example 2→Example 3 or Reference Example 9→Reference Example 2 (and then purified by silica gel column chromatography (chloroform:methanol:acetic acid=50:2:1→40:2:1→30:2:1→10:2:1), and further subjected to salt-exchange reaction, if necessary), using, as a starting material, the compound prepared in Reference Example 17, and further using a corresponding amine, the compounds of the present invention shown in Table 6 were given.

TABLE 6

| Ex. No. | Structure | Name | TLC (Rf) | NMR |
|---|---|---|---|---|
| 5(a) | (structure) | p-(p-amidino-phenoxycarbonyl)-α-methylcinnamic acid N-carboxymethyl-N-(2-ethoxycarbonylethyl)amide acetate | 0.33 (chloroform:methanol:acetic acid = 10:2:1) | 8.20(2H, d, J=8Hz), 7.90(2H, d, J=8Hz), 7.65–7.50(4H, m), 6.75(1H, m), 4.20–4.10(4H, m), 3.95–3.70(2H, m), 2.70(2H, t, J=6Hz), 2.20–2.05(3H, m), 1.25(3H, m). |
| 5(b) | (structure) | p-(p-amidino-phenoxycarbonyl)-α-methylcinnamic acid N-ethoxycarbonylmethyl-N-(2-carboxyethyl)amide acetate | 0.46 (chloroform:methanol:acetic acid = 10:2:1) | 8.20(2H, d, J=8Hz), 7.90(2H, d, J=8Hz), 7.65–7.50(4H, m), 6.70(1H, m), 4.60–4.15(4H, m), 3.90–3.60(2H, m), 2.65(2H, m), 2.15(3H, m), 1.25(3H, m). |
| 5(c) | (structure) | p-(p-amidino-phenoxycarbonyl)-α-methylcinnamic acid N-((1-(S)-carboxy-3-ethoxycarbonyl)propyl)amide trifluoroacetate | 0.27 (chloroform:methanol:acetic acid = 10:2:1) | 8.22(2H, d, J=9.0Hz), 7.93(2H, d, J=9.0Hz), 7.60(2H, d, J=9.0Hz), 7.54(2H, d, J=9.0Hz), 7.38(1H, s), 4.53(1H, dd, J=9.0Hz, 5.0Hz), 4.14(2H, q, J=7.0Hz), 2.48(2H, t, J=7.0Hz), 2.38–2.00(2H, m), 2.15(3H, s), 1.25(3H, t, J=7.0Hz). |
| 5(d) | (structure) | p-(p-amidino-phenoxycarbonyl)-α-methylcinnamic acid N-isopropyl-N-carboxymethylamide trifluoroacetate | 0.26 (chloroform:methanol:acetic acid = 10:2:1) | 8.22–8.14(2H, m), 7.95–7.88(2H, m), 7.60–7.50(4H, m), 6.77(1H, s), 4.73–4.60 and 4.38–4.24 (1H, m), 3.91 and 3.88(2H, m), 2.18 and 2.07 (3H, m), 1.23(6H, d, J=7.0Hz). |

| Ex. No. | Structure | Name | TLC (Rf) | NMR |
|---|---|---|---|---|
| 5(e) | (structure with isobutyl-N-carboxymethyl amide; CF₃COOH) | p-(p-amidino-phenoxycarbonyl)-α-methylcinnamic acid N-isobutyl-N-carboxymethyl-amide trifluoroacetate | 0.28 (chloroform:methanol:acetic acid = 10:2:1) | 8.23–8.15(2H, m), 7.94–7.88(2H, m), 7.59–7.49 (4H, m), 6.75 and 6.69(1H, m), 4.02 and 4.01 (2H, m), 3.35(2H, d, J=8.0Hz), 2.15 and 2.10 (3H, m), 2.10–1.95(1H, m), 0.97–0.90(6H, m). |
| 5(f) | (structure with N-propyl-N-carboxymethyl amide; CH₃COOH) | p-(p-amidino-phenoxycarbonyl)-α-methylcinnamic acid N-propyl-N-carboxymethyl-amide acetate | 0.26 (chloroform:methanol:acetic acid = 10:2:1) | 8.20–8.15(2H, m), 7.91(2H, d, J=9.0Hz), 7.60–7.49(4H, m), 6.74(1H, s), 4.00(2H, s), 3.46(2H, t, J=7.0Hz), 2.16 and 2.10(3H, m), 1.73–1.60(2H, m), 0.97(3H, t, J=7.0Hz). |
| 5(g) | (structure with N-((1-(R)-ethoxycarbonyl-3-carboxy)propyl); CH₃COOH) | p-(p-amidino-phenoxycarbonyl)-α-methylcinnamic acid N-((1-(R)-ethoxycarbonyl-3-carboxy)propyl)-amide acetate | 0.34 (chloroform:methanol:acetic acid = 10:2:1) | 8.22(2H, d, J=9.0Hz), 7.93(2H, d, J=9.0Hz), 7.60(2H, d, J=9.0Hz), 7.54(2H, d, J=9.0Hz), 7.37(1H, s), 4.54(1H, dd, J=9.0Hz, 5.0Hz), 4.21(2H, q, J=7.0Hz), 2.45(2H, t, J=7.0Hz), 2.34–2.00(2H, m), 2.15(3H, s), 1.30(3H, t, J=7.0Hz). |
| 5(h) | (structure with N-allyl-N-((1-(S)-ethoxycarbonyl-2-carboxy)ethyl); CH₃COOH) | p-(p-amidino-phenoxycarbonyl)-α-methylcinnamic acid N-allyl-N-((1-(S)-ethoxycarbonyl-2-carboxy)ethyl)-amide acetate | 0.35 (chloroform:methanol:acetic acid = 10:2:1) | 8.20(2H, d, J=9.0Hz), 7.92(2H, d, J=9.0Hz), 7.56(2H, d, J=9.0Hz), 7.53(2H, d, J=9.0Hz), 6.69(1H, br-s), 6.04–5.89(1H, m), 5.45–5.20(2H, m), 4.68(1H, m), 4.22–4.09(4H, m), 3.28–3.10(1H, m), 2.71–2.60(1H, m), 2.14(3H, s), 1.28(3H, t, J=7.0Hz). |

TABLE 6-continued

| Ex. No. | Structure | Name | TLC (Rf) | NMR |
|---|---|---|---|---|
| 5(i) | [structure: p-amidinophenoxycarbonyl α-methylcinnamate ester with N-allyl-N-(1-dicarboxyethyl)amide, CH₃COOH salt] | p-(p-amidino-phenoxycarbonyl)-α-methylcinnamic acid N-allyl-N-(1-(S),2-dicarboxyethyl)-amide acetate | 0.11 (chloroform:methanol:acetic acid = 10:2:1) | 8.10(2H, d, J=9.0Hz), 7.85(2H, d, J=9.0Hz), 7.56(2H, d, J=9.0Hz), 7.50(2H, d, J=9.0Hz), 6.80 and 6.74(1H, m), 6.04–5.90(1H, m), 5.33–5.09(2H, m), 4.65, 4.45, 4.38 and 4.16(2H, m), 3.78–3.65(1H, m), 3.22–3.04(1H, m), 2.80–2.66(1H, m), 2.18(3H, s). |
| 5(j) | [structure with N-carboxymethyl-N-ethoxycarbonylmethyl amide, CH₃COOH salt] | p-(p-amidino-phenoxycarbonyl)-α-methylcinnamic acid N-carboxymethyl-N-ethoxycarbonyl-methylamide acetate | 0.19 (chloroform:methanol:acetic acid = 10:2:1) | 8.20(2H, d, J=8Hz), 7.95(2H, d, J=9Hz), 7.60–7.50(4H, m), 6.75(1H, m), 4.40–4.15(6H, m), 2.15(3H, s), 2.00(3H, s, CH3COOH), 1.20(3H, t, J=7Hz). |
| 5(k) | [structure with N-(2-carboxyethyl)-N-(2-ethoxycarbonylethyl)amide, CH₃SO₃H salt] | p-(p-amidino-phenoxycarbonyl)-α-methylcinnamic acid N-(2-carboxy-ethyl)-N-(2-ethoxycarbonyl-ethyl)amide methanesulfonate | 0.13 (chloroform:methanol:acetic acid = 10:2:1) | 8.20(2H, d, J=8Hz), 7.90(2H, d, J=8Hz), 7.55(2H, d, J=8Hz), 7.50(2H, d, J=8Hz), 6.60(1H, br.), 4.15(2H, q, J=7Hz), 3.85–3.65(4H, m), 2.75–2.60(4H, m), 2.70(3H, s), 2.15(3H, s), 1.25(3H, t, J=7Hz). |
| 5(l) | [structure with N-2,4-hexadienyl-N-carboxymethyl amide, CH₃SO₃H salt] | p-(p-amidino-phenoxycarbonyl)-α-methylcinnamic acid N-2,4-hexadienyl-N-carboxymethyl-amide methanesulfonate | 0.30 (chloroform:methanol:acetic acid = 10:2:1) | 8.20(2H, d, J=8Hz), 7.90(2H, d, J=9Hz), 7.60–7.50(4H, m), 6.75(1H, m), 6.30–6.00(2H, m), 5.8–5.50(2H, m), 4.20–4.10(4H, m), 2.75(3H, s), 2.15(3H, m), 1.80(3H, d, J=8Hz). |

TABLE 6-continued

| Ex. No. | Structure | Name | TLC (Rf) | NMR |
|---|---|---|---|---|
| 5(m) | [structure with CH₃SO₃H] | p-(p-amidino-phenoxycarbonyl)-α-methylcinnamic acid N,N-bis-(2-carboxyethyl)amide methanesulfonate | 0.58 (chloroform:methanol:acetic acid = 3:1:1) | 8.20(2H, d, J=8Hz), 7.90(2H, d, J=8Hz), 7.55(2H, d, J=8Hz), 7.50(2H, d, J=8Hz), 6.60(1H, br.), 3.90–3.65(4H, br.), 2.70(3H, s), 2.70–2.60 (4H, m), 2.15(3H, s). |
| 5(n) | [structure with CH₃COOH] | p-(p-amidino-phenoxycarbonyl)-α-methylcinnamic acid N-(1-(S),3-dicarboxypropyl)-amide acetate | 0.47 (chloroform:methanol:acetic acid = 10:2:1) | 8.21(2H, d, J=9.0Hz), 7.90(2H, d, J=9.0Hz), 7.57(2H, d, J=9.0Hz), 7.50(2H, d, J=9.0Hz), 7.42(1H, s), 4.52(1H, dd, J=7.0Hz, 5.0Hz), 2.53–2.45(2H, m), 2.37–2.08(2H, m), 2.16(3H, s), 2.02(3H, s, CH3COOH). |
| 5(o) | [structure with CH₃COOH] | p-(p-amidino-phenoxycarbonyl)-α-methylcinnamic acid N-allyl-N-(1-(S)-carboxy-2-ethoxycarbonyl-ethyl)amide acetate | 0.23 (chloroform:methanol:acetic acid = 10:2:1) | 8.20(2H, d, J=8Hz), 7.95(2H, d, J=9Hz), 7.60–7.50(4H, m), 6.80(1H, m), 5.95(1H, m), 5.30–5.00(2H, m), 4.60(1H, m), 4.15(2H, m), 3.30–2.70(2H, m), 2.20(3H, m), 2.00(3H, s, CH3COOH), 1.25(3H, m). |
| 5(p) | [structure with CH₃COOH] | p-(p-amidino-phenoxycarbonyl)-α-methylcinnamic acid N-(1-carboxy-1-ethoxycarbonyl-methyl)-N-(3-ethoxycarbonyl-propyl)amide acetate | 0.23 (chloroform:methanol:acetic acid = 10:2:1) | 8.21(2H, d, J=8 Hz), 7.92(2H, d, J=8 Hz), 7.5–7.6(4H, m), 6.61 and 6.76(1H, s, rotamers), 4.95(1H), 4.0–4.3(4H, m), 3.5–3.77(2H, m), 2.35(2H, t, J=7 Hz), 1.9–2.2(5H, m), 1.90(3H, s), 1.1–1.4(6H, m). |

TABLE 6-continued

| Ex. No. | Structure | Name | TLC (Rf) | NMR |
|---|---|---|---|---|
| 5(q) | [structure: p-amidinophenyl ester of cinnamic acid derivative with N-(1,1-bis(ethoxycarbonyl)methyl)-N-(3-carboxypropyl)amide; CH₃COOH] | p-(p-amidinophenoxycarbonyl)-α-methylcinnamic acid N-(1,1-bis(ethoxycarbonyl)methyl)-N-(3-carboxypropyl)-amide acetate | 0.38 (chloroform:methanol:acetic acid = 10:2:1) | (CD3OD + CDCl3) 8.30–7.30(8H, m, aromatic, 2 rotamers), 6.72 and 6.61(1H, s, olefinic, 2 rotamers), 4.40–4.00(4H, m, COOCH2 X 2, 2 rotamers), 3.70–3.40(3H, m, NCH2 and NCHCOO, 2 rotamers), 2.40–1.80(10H, m), 1.44–1.10(6H, m, CH3 x 2, 2 rotamers). |
| 5(r) | [structure: p-amidinophenyl ester with N-benzyl-N-carboxymethyl amide; CH₃COOH] | p-(p-amidinophenoxycarbonyl)-α-methylcinnamic acid N-carboxymethyl-N-phenylmethylamide acetate | 0.36 (chloroform:methanol:acetic acid = 10:2:1) | 8.20(2H, d, J=8Hz), 7.95(2H, d, J=9Hz), 7.60–7.45(4H m), 6.75(1H, m), 4.75(2H, m), 4.10(2H, brs), 2.70(3H, s), 2.15(3H, s). |
| 5(s) | [structure: p-amidinophenyl ester with N-(1-propylbutyl)-N-carboxymethyl amide; CH₃COOH] | p-(p-amidinophenoxycarbonyl)-α-methylcinnamic acid N-carboxymethyl-N-1-propylbutylamide acetate | 0.26 (chloroform:methanol:acetic acid = 10:2:1) | 8.23(2H, d, J=8Hz), 7.91(2H, d, J=8Hz), 7.56(4H, t, J=8Hz), 6.65(1H, m), 4.20(1H, m), 3.98(2H, s), 2.10(3H, m), 1.90(3H, s), 1.60–1.10(8H, m), 0.92(6H, t, J=7Hz). |
| 5(t) | [structure: p-amidinophenyl ester with N-methyl-N-carboxymethyl methylamide; CH₃COOH] | p-(p-amidinophenoxycarbonyl)-α-methylcinnamic acid N-carboxymethyl-N-methyl-N-methylamide acetate | 0.25 (chloroform:methanol:acetic acid = 10:2:1) | 8.20(2.H, d, J=7Hz), 7.96(2H, d, J=7Hz), 7.65–7.50(4H, m), 6.65(1H, m), 4.20(2H, m), 2.80(3H, br), 2.15(3H, s), 1.95(3H, s). |

TABLE 6-continued

| Ex. No. | Structure | Name | TLC (Rf) | NMR |
|---|---|---|---|---|
| 5(u) | (structure) | p-(p-amidino-phenoxycarbonyl)-α-methylcinnamic acid N-carboxy-methyl-N-ethyl-amide acetate | 0.23 (chloroform:methanol:acetic acid = 10:2:1) | 8.20(2H, d, J=8Hz), 7.90(2H, d, J=9Hz), 7.60–7.50(4H, m), 6.65(1H, m), 4.20(2H, m), 3.45(2H, m), 2.15(3H, m), 1.95(3H, s), 0.95(3H, m). |
| 5(v) | (structure) | p-(p-amidino-phenoxycarbonyl)-α-methylcinnamic acid N-carboxy-methyl-N-butyl-amide acetate | 0.29 (chloroform:methanol:acetic acid = 10:2:1) | 8.22(2H, d, J=8Hz), 7.92(2H, d, J=8Hz), 7.56(4H, t, J=8Hz), 6.70–6.60(1H, m), 4.22(2H, q, J=7Hz), 4.15(2H, s), 3.49(2H, t, J=7Hz), 2.10(3H, s), 1.93(3H, s), 1.80–1.50(2H, m), 1.50–1.20(2H, m), 0.93(3H, brt, J=7Hz). |
| 5(w) | (structure) | p-(p-amidino-phenoxycarbonyl)-α-methylcinnamic acid N-carboxy-methyl-N-3-methylbutylamide acetate | 0.26 (chloroform:methanol:acetic acid = 10:2:1) | 8.20(2H, d, J=7Hz), 7.95(2H, d, J=7Hz), 7.65–7.50(4H, m), 6.65(1H, m), 4.20(2H, m), 3.50(2H, m), 2.15(3H, m), 1.95(3H, s), 1.70–1.40(3H, m), 0.90(6H, m). |
| 5(x) | (structure) | p-(p-amidino-phenoxycarbonyl)-α-methylcinnamic acid N-carboxy-methyl-N-hexyl-amide acetate | 0.25 (chloroform:methanol:acetic acid = 10:2:1) | 8.22(2H, d, J=8Hz), 7.92(2H, d, J=8Hz), 7.56(4H, t, J=8Hz), 6.70–6.60(1H, m), 4.15(2H, s), 3.49(2H, t, J=7Hz), 2.10(3H, m), 1.93(3H, s), 1.80–1.50(2H, m), 1.50–1.20(6H, m), 1.00–0.80(3H, br). |

| Ex. No. | Structure | Name | TLC (Rf) | NMR |
|---|---|---|---|---|
| 5(y) | p-(p-amidinophenoxycarbonyl)-α-methylcinnamic acid N-carboxymethyl-N-cyclopropylamide acetate (cyclopropyl structure) | p-(p-amidinophenoxycarbonyl)-α-methylcinnamic acid N-carboxymethyl-N-cyclopropylamide acetate | 0.25 (chloroform:methanol:acetic acid = 10:2:1) | 8.20(2H, d, J=7Hz), 7.95(2H, d, J=7Hz), 7.65–7.50(4H, m), 6.85(1H, m), 4.20(2H, s), 3.00(1H, br), 2.20(3H, s), 1.95(3H, s), 0.95–0.90(4H, m). |
| 5(z) | p-(p-amidinophenoxycarbonyl)-α-methylcinnamic acid N-carboxymethyl-N-cyclobutylamide acetate (cyclobutyl structure) | p-(p-amidinophenoxycarbonyl)-α-methylcinnamic acid N-carboxymethyl-N-cyclobutylamide acetate | 0.22 (chloroform:methanol:acetic acid = 10:2:1) | 8.25(2H, d, J=9.5Hz), 7.90(2H, d, J=8Hz), 7.60–7.50(4H, m), 6.65(1H, brs), 4.25–4.05(3H, m), 2.15(3H, brs), 1.95(3H, s), 2.00–1.05(6H, m). |
| 5(aa) | p-(p-amidinophenoxycarbonyl)-α-methylcinnamic acid N-carboxymethyl-N-cyclopentylamide acetate (cyclopentyl structure) | p-(p-amidinophenoxycarbonyl)-α-methylcinnamic acid N-carboxymethyl-N-cyclopenrylamide acetate | 0.26 (chloroform:methanol:acetic acid = 10:2:1) | 8.25(2H, d, J=9.5Hz), 7.90(2H, d, J=8Hz), 7.60–7.50(4H, m), 6.65(1H, brs), 4.25–4.05(2H, m), 3.80(1H, m), 2.15(3H, brs), 1.95(3H, s), 2.00–1.80(4H, m), 1.75–1.05(4H, m). |
| 5(bb) | p-(p-amidinophenoxycarbonyl)-α-methylcinnamic acid N-carboxymethyl-N-cyclohexylamide acetate (cyclohexyl structure) | p-(p-amidinophenoxycarbonyl)-α-methylcinnamic acid N-carboxymethyl-N-cyclohexylamide acetate | 0.25 (chloroform:methanol:acetic acid = 10:2:1) | 8.15(2H, d, J=9.5Hz), 7.90(2H, 1.75–1.05(4H, m), 7.60–7.50(4H, m), 6.85(1H, m), 4.25–4.05(2H, m), 3.80(1H, m), 2.15(3H, brs), 1.95(3H, s), 2.00–1.80(4H, m), 1.75–1.05(6H, m). |

TABLE 6-continued

| Ex. No. | Structure | Name | TLC (Rf) | NMR |
|---|---|---|---|---|
| 5(cc) | (structure) CH₃COOH | p-(p-amidino-phenoxycarbonyl)-α-methylcinnamic acid N-2-carboxy-ethyl-N-methyl-amide acetate | 0.25 (chloroform:methanol:acetic acid = 10:2:1) | 8.20(2H, d, J=7Hz), 7.95(2H, d, J=7Hz), 7.60–7.50(4H, m), 6.65(1H, m), 3.80(2H, m), 2.80(3H, br), 2.75(2H, m), 2.15(3H, m), 1.95(3H, s). |
| 5(dd) | (structure) CH₃COOH | p-(p-amidino-phenoxycarbonyl)-α-methylcinnamic acid N-2-carboxy-ethyl-N-ethylamide acetate | 0.26 (chloroform:methanol:acetic acid = 10:2:1) | 8.20(2H, d, J=8Hz), 7.90(2H, d, J=9Hz), 7.60–7.50(4H, m), 6.65(1H, m), 3.80(2H, m), 3.45(2H, m), 2.75(2H, m), 2.15(3H, m), 1.95(3H, s), 0.95(3H, m). |
| 5(ee) | (structure) CH₃COOH | p-(p-amidino-phenoxycarbonyl)-α-methylcinnamic acid N-2-carboxy-ethyl-N-propyl-amide acetate | 0.26 (chloroform:methanol:acetic acid = 10:2:1) | 8.25(2H, d, J=7Hz), 7.95(2H, d, J=7Hz), 7.55(4H, m), 6.60(1H, m), 3.75(2H, m), 3.50(2H, m), 2.70(2H, m), 2.15(3H, s), 1.95(3H, s), 1.70(2H, m), 0.95(3H, m). |
| 5(ff) | (structure) CH₃COOH | p-(p-amidino-phenoxycarbonyl)-α-methylcinnamic acid N-2-carboxy-ethyl-N-1-methyl-ethylamide acetate | 0.28 (chloroform:methanol:acetic acid = 10:2:1) | 8.20(2H, d, J=8Hz), 7.95(2H, d, J=8Hz), 7.58(2H, d, J=8Hz), 7.53(2H, d, J=8Hz), 6.62(1H, s), 4.40–4.20(1H, m), 3.60(2H, brt, J=7.5Hz), 2.68(2H, t, J=7.5Hz), 2.15 (3H, s), 1.92(3H, s), 1.28(6H, d, J=6Hz). |

TABLE 6-continued
| Ex. No. | Structure | Name | TLC (Rf) | NMR |
|---|---|---|---|---|
| 5(gg) | 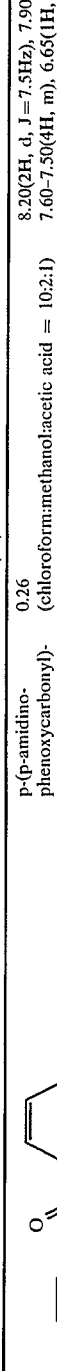 | p-(p-amidino-phenoxycarbonyl)-α-methylcinnamic acid N-2-carboxy-ethyl-N-allyllamide acetate | 0.26 (chloroform:methanol:acetic acid = 10:2:1) | 8.20(2H, d, J=7.5Hz), 7.90(2H, d, J=7.5Hz), 7.60-7.50(4H, m), 6.65(1H, m), 5.90(1H, m), 5.40-5.20(2H, m), 4.20-4.05(2H, m), 3.75 (2H, m), 2.70(2H, m), 2.10(3H, s), 1.95(3H, s). |

Formulation Example

Formulation Example 1

The following components were admixed in conventional manner and punched out to obtain 100 tablets each containing 50 mg of active ingredient.

| | |
|---|---|
| p-(p-Amidinophenoxycarbonyl)-α-methylcinnamic acid N-allyl-N-ethoxycarbonylmethylamide acetate | 5.0 g |
| Carboxymethylcellulose calcium (disintegrating agent) | 0.2 g |
| Magnesium stearate (lubricating agent) | 0.1 g |
| Microcrystalline cellulose | 4.7 g |

Formulation Example 2

The following components were admixed in conventional manner. The solution was sterilized in conventional manner, placed 5 ml portions into ampoules and freeze-dried to obtain 100 ampoules each containing 20 mg of active ingredient.

| | |
|---|---|
| p-(p-Amidinophenoxycarbonyl)-α-methylcinnamic acid N-allyl-N-ethoxycarbonylmethylamide acetate | 2 g |
| Anhydrous citric acid | 200 mg |
| Distilled water | 500 ml |

What we claim is:

1. A compound of the formula (I):

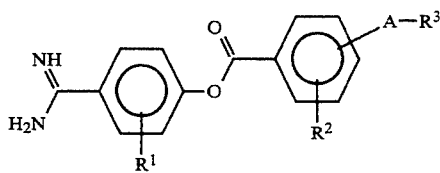

wherein $R^1$ and $R^2$ each, independently, is:

(i) hydrogen, (ii) C1–4 alkyl, (iii) C1–4 alkoxy, (iv) C2–5 acyl, (v) halogen, (vi) nitro, (vii) benzoyl or (viii) $COOR^4$ (in which $R^4$ is C1–3 alkyl);

A is bond, C1–4 alkylene or

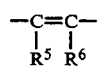

(in which $R^5$ and $R^6$ each independently, is hydrogen or C1–4 alkyl);

$R^3$ is

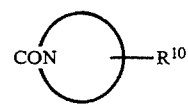

wherein

is 6 membered, mono-cyclic hetero ring containing one or two nitrogen;

$R^{10}$ is (1) hydrogen, (2) C7–10 phenylalkyl or (3) $COOR^{13}$ (in which $R^{13}$ is hydrogen, C1–4 alkyl or C7–10 phenylalkyl));

or an acid-addition salt thereof.

2. A compound according to claim 1, wherein

contains one nitrogen.

3. A compound according to claim 1, wherein

contains two nitrogens.

4. A compound according to claim 1, wherein

is piperazine.

5. A compound according to claim 1, which is selected from the group consisting of p-(p-amidinophenoxycarbonyl)-α-methylcinnamic acid N'-phenylmethylpiperazinylamide and p-amidinophenoxycarbonyl)cinnamic acid N'-phenylmethylpiperazinylamide bishydrochloride.

6. A compound according to claim 1, which is p-(p-amidinophenoxycarbonyl) cinnamic acid N'-phenylmethyl piperazinylamide bishydrochloride.

7. A pharmaceutical composition which comprises, as active ingredient, an effective amount of a compound of the formula (I) depicted in claim 1, or an acid addition salt thereof, with a carrier or coating.

8. A method for the prevention and/or treatment in animals, including man, of inflammatory diseases, allergic diseases, disseminated intravascular coagulation, pancreatitis, severity in pancreatitis or multiple organ failure, which comprises the administration to a patient of an effective amount of a compound of the formula (I) depicted in claim 1, or an acid addition salt thereof.

* * * * *